United States Patent
Xiang et al.

(10) Patent No.: US 7,019,003 B2
(45) Date of Patent: Mar. 28, 2006

(54) PEPTIDE DEFORMYLASE INHIBITORS

(75) Inventors: Jia-Ning Xiang, Palo Alto, CA (US); Siegfried B. Christensen, IV, Collegeville, PA (US); Jinhwa Lee, Collegeville, PA (US); Daniel J. Mercer, Collegeville, PA (US)

(73) Assignee: Smithkline Beecham Corporation, Philadelphia, PA (US)

( * ) Notice: Subject to any disclaimer, the term of this patent is extended or adjusted under 35 U.S.C. 154(b) by 321 days.

(21) Appl. No.: 10/469,433

(22) PCT Filed: Mar. 1, 2002

(86) PCT No.: PCT/US02/06275

§ 371 (c)(1),
(2), (4) Date: Aug. 28, 2003

(87) PCT Pub. No.: WO02/070541

PCT Pub. Date: Sep. 12, 2002

(65) Prior Publication Data

US 2004/0087585 A1 May 6, 2004

Related U.S. Application Data

(60) Provisional application No. 60/272,570, filed on Mar. 1, 2001.

(51) Int. Cl.
*A61K 31/535* (2006.01)
*C07C 271/00* (2006.01)

(52) U.S. Cl. .................. 514/234.8; 514/234.8; 514/237.5; 514/237.8; 514/255.01; 514/258.1; 514/277; 514/311; 514/315; 514/330; 514/351; 514/359; 514/394; 514/411; 514/415; 562/555; 562/621; 544/162; 544/335; 544/355; 544/390; 546/122; 546/146; 546/159; 546/169; 546/245; 546/254; 546/316; 548/261; 548/301.4; 548/304.4; 548/309.4; 548/429; 548/492; 548/507; 549/159; 549/362; 549/365; 549/366; 549/424; 549/469; 549/487

(58) Field of Classification Search .............. 514/234.8, 514/237.5, 237.8, 225.01, 258.1, 277, 311, 514/315, 330, 351, 359, 394, 411, 415; 562/555, 562/621; 544/162, 335, 355, 390; 546/122, 546/146, 159; 548/261, 301.4; 549/159, 362, 549/365

See application file for complete search history.

(56) References Cited

U.S. PATENT DOCUMENTS

| | | |
|---|---|---|
| 4,996,358 A | 2/1991 | Handa et al. |
| 5,691,382 A | 11/1997 | Crimmin et al. |
| 6,013,792 A | 1/2000 | Castelhano et al. |
| 6,028,110 A | 2/2000 | Miller et al. |
| 6,037,472 A | 3/2000 | Castelhan et al. |

*Primary Examiner*—Paul A. Zucker
(74) *Attorney, Agent, or Firm*—Laura K. Madden; Loretta J. Henderson; Mary S. McCarthy

(57) ABSTRACT

Novel PDF inhibitors and novel methods for their use are provided.

10 Claims, 1 Drawing Sheet

PEPTIDE DEFORMYLASE INHIBITORS

This application claims the benefit of U.S. Provisional Application No. 60/272,570, filed Mar. 1, 2001.

FIELD OF THE INVENTION

The present invention relates to the use of novel antibacterial compounds, and pharmaceutical compositions containing these compounds as peptide deformylase inhibitors.

BACKGROUND OF THE INVENTION

Bacterial initiator methionyl tRNA is modified by methionyl tRNA formyltransferase (FMT) to produce formyl-methionyl tRNA. The formyl methionine (f-met) is then incorporated at the N-termini of newly synthesized polypeptides. Polypeptide deformylase (PDF or Def) then deformylates primary translation products to produce N-methionyl polypeptides. Most intracellular proteins are further processed by methionine amino peptidase (MAP) to yield the mature peptide and free methionine, which is recycled. PDF and MAP are both essential for bacterial growth, and PDF is required for MAP activity. This series of reactions is referred to as the methionine cycle (FIG. 1).

To date, polypeptide deformylase homologous genes have been found in bacteria, in chloroplast-containing plants, in mice and in human. The plant proteins are nuclear encoded but appear to carry a chloroplast localisation signal. This is consistent with the observation that chloroplast RNA and protein synthesis processes are highly similar to those of eubacteria. While there is limited information on protein expression of mammalian PDF gene homologs (Bayer Aktiengesellschaft, Pat. WO2001/42431), no functional role for such proteins has been demonstrated to date (Meinnel, T., Parasitology Today 16(4), 165–168, 2000).

Polypeptide deformylase is found in all eubacteria for which high coverage genomic sequence information is available. Sequence diversity among PDF homologs is high, with as little as 20% identity between distantly related sequences. However, conservation around the active site is very high, with several completely conserved residues, including one cysteine and two histidines which are required to coordinate the active site metal (Meinnel, T. et al., J. Mol. Biol. 267, 749–761, 1997).

PDF is recognized to be an attractive antibacterial target, as this enzyme has been demonstrated to be essential for bacterial growth in vitro (Mazel, D. et al., EMBO J. 13 (4), 914–923, 1994), is not believed to be involved in eukaryotic protein synthesis (Rajagopalan et al., J. Am. Chem. Soc. 119, 12418–12419, 1997), and is universally conserved in prokaryotes (Kozak, M., Microbiol. Rev. 47, 1–45, 1983). Therefore PDF inhibitors can potentially serve as broad spectrum antibacterial agents.

SUMMARY OF THE INVENTION

The present invention involves novel anti-bacterial compounds represented by Formula (1) hereinbelow and their use as PDF inhibitors.

DETAILED DESCRIPTION OF THE INVENTION

Figure 1:
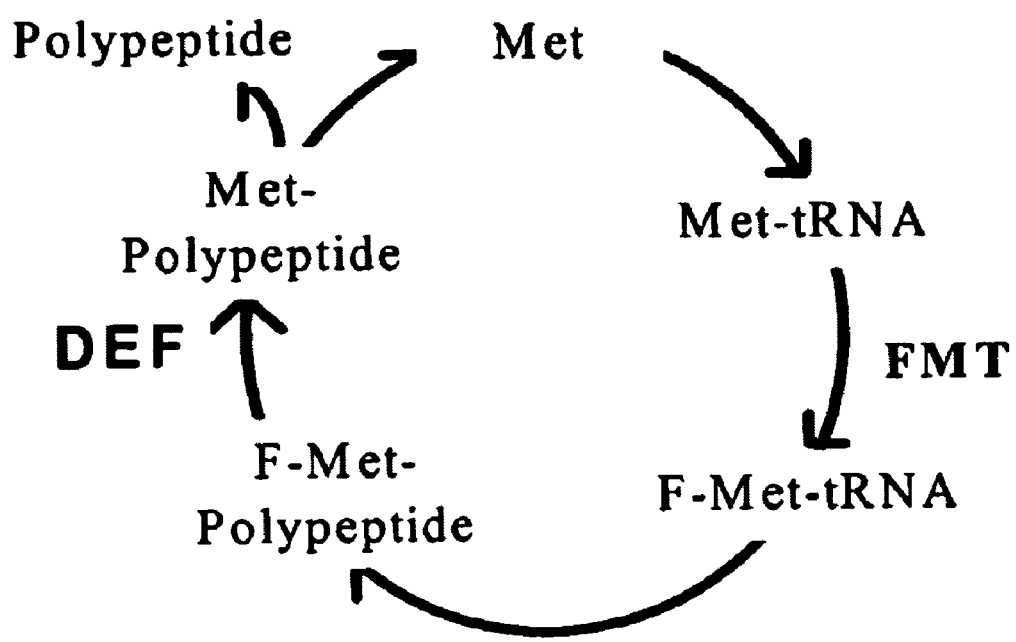
FIG. 1: Provides a graph of th methionine cycle.

In one aspect of the present invention, there is provided a compound of formula (1):

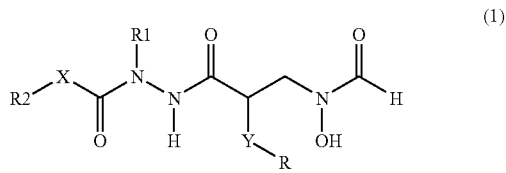

X = O, NR$_3$ or a bond;
Y = O, CH$_2$ or a bond wherein:

R represents:
   $C_{2-6}$ alkyl (optionally substituted by alkoxy, halogen, or $C_{1-3}$ alkylsulfanyl), $C_{2-6}$ alkenyl (optionally substituted by alkoxy, halogen, or $C_{1-3}$ alkylsulfanyl), $C_{2-6}$ alkynyl (optionally substituted by alkoxy, halogen, or $C_{1-3}$ alkylsulfanyl), $(CH_2)_n$—$C_{3-6}$ carbocycle (optionally substituted by alkoxy, halogen, or $C_{1-3}$ alkylsulfanyl), $(CH_2)_n$—$R_4$ {where $R_4$ is phenyl, furan, benzofuran, thiophene, benzothiophene, tetrahydrofuran, tetrahydropyran, dioxane, 1,4-benzodioxane or benzo[1,3]dioxole; $R_4$ is optionally substituted by one or more Cl, Br, I, $C_{1-3}$ alkyl (optionally substituted by one to three F) or $C_{1-2}$ alkoxy (optionally substituted by one to three F)};

R1 represents:
   hydrogen, $C_{1-6}$ alkyl (optionally substituted by hydroxy, halogen, amino, guanidino, phenyl, pyridyl, pyrrolyl, indolyl, imidazolyl, furanyl, benzofuranyl, piperidinyl, morpholinyl, quinolinyl, piperazinyl or dimethylaminophenyl) or $(CH_2)_n$—$C_{3-7}$ carbocycle;

R2 represents:
   hydrogen (provided that X is not O), $C_{1-3}$ substituted alkyl, $C_{2-3}$ substituted alkenyl, $C_{2-3}$ substituted alkynyl, $(CH_2)_n$—$C_{3-6}$ substituted carbocycle, aryl, heteroaryl, heterocyclic, carboxy (provided that X is not NR3 or O) or aminocarbonyl (provided that X is not NR3 or O);

R3 represents:
   hydrogen, $C_{1-3}$ substituted alkyl, phenyl, or may be taken together with R2 and the nitrogen atom to which they are attached to form an optionally substituted heterocyclic ring which is optionally fused to an aryl, a heteroaryl, or a second heterocyclic ring;

X represents O, NR3 or a covalent bond;

Y represents O, CH$_2$ or a covalent bond;

n=0–2;

or a salt, solvate, or physiologically functional derivative thereof.

In this invention the most preferred RI group is hydrogen. Furthermore, in this invention the most preferred absolute configuration of compounds of the formula (1) is indicated below:

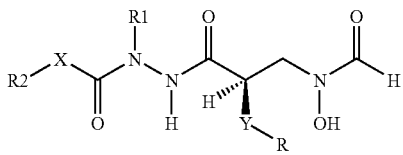

X = O, NR₃ or a bond;
Y = O, CH₂ or a bond

In a second aspect of the present invention, there is provided a compound of Formula (1) wherein X=O, and R, R1, R2, R3, R4, Y and n are as defined above; or a salt, solvate, or physiologically functional derivative thereof.

In a third aspect of the present invention, there is provided a compound of Formula (1) wherein X=NR3, and R, R1, R2, R3, R4, Y and n are as defined above; or a salt, solvate, or physiologically functional derivative thereof.

In a fourth aspect of the present invention, there is provided a compound of Formula (1) wherein X is a covalent bond, and R, R1, R2, R3, R4, Y and n are as defined above; or a salt, solvate, or physiologically functional derivative thereof.

As used herein, the term "alkyl" refers to a straight or branched chain saturated hydrocarbon radical. Examples of "alkyl" as used herein include, but are not limited to, methyl, ethyl, n-propyl, isopropyl, n-butyl, isobutyl, t-butyl, n-pentyl, isopentyl, hexyl and the like.

As used herein, the term "substituted alkyl" refers to a straight or branched chain saturated hydrocarbon radical, optionally substituted with substituents selected from the group that includes $C_{1-3}$ alkyl (optionally substituted by one to three fluorines), $C_{2-3}$ alkenyl, $C_{2-3}$ alkynyl, $C_{1-2}$ alkoxy (optionally substituted by one to three fluorines), sulfanyl, sulfinyl, sulfonyl, oxo, hydroxy, mercapto, amino, guanidino, carboxy, aminocarbonyl, aryl, aryloxy, heteroaryl, heteroaryloxy, heterocyclic, aminosulfonyl, sulfonylamino, carboxyamide, ureido, nitro, cyano and halogen, multiple degrees of substitution being allowed.

As used herein, the term "alkenyl" refers to a straight or branched chain hydrocarbon radical having at least one carbon-carbon double bond. Examples of "alkenyl" as used herein include, but are not limited to, ethenyl and propenyl.

As used herein, the term "substituted alkenyl" refers to a straight or branched chain hydrocarbon radical having at least one carbon-carbon double bond, optionally substituted with substituents selected from the group which includes $C_{1-3}$ alkyl (optionally substituted by one to three F), amino, aryl, cyano and halogen, multiple degrees of substitution being allowed.

As used herein, the term "alkynyl" refers to a straight or branched chain hydrocarbon radical having at least one carbon-carbon triple bond. Examples of "alkynyl" as used herein include, but are not limited to, acetylenyl and 1-propynyl.

As used herein, the term "substituted alkynyl" refers to a straight or branched chain hydrocarbon radical having at least one carbon-carbon triple bond, optionally substituted with substituents selected from the group which includes $C_{1-3}$ alkyl (optionally substituted by one to three F), amino, aryl and halogen, multiple degrees of substitution being allowed.

As used herein, the term "halogen" refers to fluorine (F), chlorine (Cl), bromine (Br), or iodine (I), and "halo" refers to the halogen radicals fluoro, chloro, bromo and iodo.

As used herein, the term "carbocycle" refers to a non-aromatic cyclic hydrocarbon radical having from three to seven carbon atoms. For carbocycles with five- to seven-membered rings, a ring double bond is allowed. Exemplary "carbocycle" groups include, but are not limited to, cyclopropyl, cyclobutyl, cyclopentyl, cyclopentenyl, cyclohexyl, and cycloheptyl.

As used herein, the term "substituted carbocycle" refers to a non-aromatic cyclic hydrocarbon radical having from three to seven carbon atoms, and which is optionally substituted with substituents selected from the group which includes $C_{1-3}$ alkyl (optionally substituted by one to three F), $C_{2-3}$ alkenyl, $C_{2-3}$ alkynyl, $C_{1-2}$ alkoxy (optionally substituted by one to three F), sulfanyl, sulfinyl, sulfonyl, oxo, hydroxy, mercapto, amino, guanidino, carboxy, aminocarbonyl, aryl, aryloxy, heteroaryl, heterocyclic, aminosulfonyl, sulfonylamino, carboxyamide, nitro, ureido, cyano and halogen, multiple degrees of substitution being allowed. For carbocycles with five- to seven-membered rings, a ring double bond is allowed.

As used herein, the term "aryl" refers to an optionally substituted benzene ring or to an optionally substituted benzene ring fused to one or more optionally substituted benzene rings to form a ring system. Exemplary optional substituents include $C_{1-3}$ substituted alkyl, $C_{2-3}$ substituted alkenyl, $C_{2-3}$ substituted alkynyl, heteroaryl, heterocyclic, aryl, $C_{1-3}$ alkoxy (optionally substituted by one to three F), aryloxy, aralkoxy, acyl, aroyl, heteroaroyl, acyloxy, aroyloxy, heteroaroyloxy, sulfanyl, sulfinyl, sulfonyl, aminosulfonyl, sulfonylamino, carboxyamide, aminocarbonyl, carboxy, oxo, hydroxy, mercapto, amino, nitro, cyano, halogen, or ureido, multiple degrees of substitution being allowed. Such a ring or ring system may be optionally fused to one or more optionally substituted aryl rings (including benzene rings), carbocycle rings or heterocyclic rings. Examples of "aryl" groups include, but are not limited to, phenyl, naphthyl, tetrahydronaphthyl, biphenyl, indanyl, anthracyl or phenanthryl, as well as substituted derivatives thereof.

As used herein, the term "heteroaryl" refers to an optionally substituted monocyclic five to six membered aromatic ring containing one or more heteroatomic substitutions selected from S, SO, $SO_2$, O, N, or N-oxide, or to such an aromatic ring fused to one or more optionally substituted rings, such as heteroaryl rings, aryl rings, heterocyclic rings, or carbocycle rings (e.g., a bicyclic or tricyclic ring system). Examples of optional substituents are selected from the group which includes $C_{1-3}$ substituted alkyl, $C_{2-3}$ substituted alkenyl, $C_{2-3}$ substituted alkynyl, heteroaryl, heterocyclic, aryl, $C_{1-3}$ alkoxy (optionally substituted by one to three F), aryloxy, aralkoxy, acyl, aroyl, heteroaroyl, acyloxy, aroyloxy, heteroaroyloxy, sulfanyl, sulfinyl, sulfonyl, aminosulfonyl, sulfonylamino, carboxyamide, aminocarbonyl, carboxy, oxo, hydroxy, mercapto, amino, nitro, cyano, halogen or ureido, multiple degrees of substitution being allowed. Examples of "heteroaryl" groups used herein include, but are not limited to, benzoimidazolyl, benzothiazolyl, benzoisothiazolyl, benzothiophenyl, benzopyrazinyl, benzotriazolyl, benzo[1,4]dioxanyl, benzofuranyl, 9H-a-carbolinyl, cinnolinyl, furanyl, furo[2,3-b]pyridinyl, imidazolyl, imidazolidinyl, imidazopyridinyl, isoxazolyl, isothiazolyl, isoquinolinyl, indolyl, indazolyl, indolizinyl, naphthyridinyl, oxazolyl, oxothiadiazolyl, oxadiazolyl, phthalazinyl, pyridyl, pyrrolyl, purinyl, pteridinyl, phenazinyl, pyrazolyl, pyridyl, pyrazolopyrimidinyl, pyrrolizinyl, pyridazyl, pyrazinyl, pyrimidyl, 4-oxo-1,2-dihydro-4H-pyrrolo[3,2,1-ij]- quinolin-4-yl, quinoxalinyl, quinazolinyl, quinolinyl, quinolizinyl, thiophenyl, triazolyl, triazinyl, tetrazolopyrimidinyl, triazolopyrimidinyl, tetrazolyl,: thiazolyl, thiazolidinyl, and substituted versions thereof.

As used herein, the term "heterocyclic" refers to a three to seven-membered ring containing one or more heteroatomic moieties selected from S, SO, $SO_2$, O, N, or N-oxide, optionally substituted with substituents selected from the group which includes $C_{1-3}$ substituted alkyl, $C_{2-3}$ substituted alkenyl, $C_{2-3}$ substituted alkynyl, heteroaryl, heterocyclic, aryl, $C_{1-3}$ alkoxy (optionally substituted by one to three F), aryloxy, aralkoxy, acyl, aroyl, heteroaroyl, acyloxy, aroyloxy, heteroaroyloxy, sulfanyl, sulfinyl, sulfonyl, aminosulfonyl, sulfonylamino, carboxyamide, aminocarbonyl, carboxy, oxo, hydroxy, mercapto, amino, nitro, cyano, halogen, or ureido, multiple degrees of substitution being allowed. Such a ring can be saturated or have one or more degrees of unsaturation. Such a ring may be optionally fused to one or more other optionally substituted "heterocyclic" ring(s), aryl ring(s), heteroaryl ring(s), or carbocycle ring(s). Examples of "heterocyclic" moieties include, but are not limited to, 1,4-dioxanyl, 1,3-dioxanyl, pyrrolidinyl, pyrrolidin-2-onyl, piperidinyl, imidazolidine-2,4-dionepiperidinyl, piperazinyl, piperazine-2,5-dionyl, morpholinyl, dihydropyranyl, dihydrocinnolinyl, 2,3-dihydrobenzo[1,4]dioxinyl, 3,4-dihydro-2H-benzo[b][1,4] dioxepinyl, tetrahydropyranyl, 2,3-dihydrofuranyl, 2,3-dihydrobenzofuranyl, dihydroisoxazolyl, tetrahydrobenzodiazepinyl, tetrahydroquinolinyl, tetrahydrofuranyl, tetrahydronaphthyridinyl, tetrahydropurinyl, tetrahydrothiopyranyl, tetrahydrothiophenyl, tetrahydroquinoxalinyl, tetrahydropyridinyl, tetrahydrocarbolinyl, 4H-benzo[1,3]-dioxinyl, benzo[1,3]dioxonyl, 2,2-difluorobenzo-[1,3]-dioxonyl, 2,3-dihydro-phthalazine-1,4-dionyl, isoindole-1,3-dionyl, and the like.

As used herein, the term "alkoxy" refers to the group —$OR_a$, where $R_a$ is alkyl as defined above. Exemplary alkoxy groups useful in the present invention include, but are not limited to, methoxy, difluoromethoxy, trifluoromethoxy, ethoxy, n-propoxy, isopropoxy, n-butoxy, and t-butoxy.

As used herein the term "aralkoxy" refers to the group —$OR_aR_b$, where $R_a$ is alkyl and $R_b$ is aryl as defined above.

As used herein the term "aryloxy" refers to the group —$OR_a$, where $R_a$ is aryl as defined above.

As used herein, the term "mercapto" refers to the group —SH.

As used herein, the term "sulfanyl" refers to the group —$SR_a$, where $R_a$ is substituted alkyl, substituted carbocycle, aryl, heteroaryl or heterocyclic, as defined above.

As used herein, the term "sulfinyl" refers to the group —$S(O)R_a$, where $R_a$ is substituted alkyl, substituted carbocycle, aryl, heteroaryl or heterocyclic, as defined above.

As used herein, the term "sulfonyl" refers to the group —$S(O)_2R_a$, where $R_a$ is substituted alkyl, substituted carbocycle, aryl, heteroaryl or heterocyclic, as defined above.

As used herein, the term "oxo" refers to the group =O.

As used herein, the term "hydroxy" refers to the group —OH.

As used herein, the term "amino" refers to the group —$NH_2$. The amino group is optionally substituted by substituted alkyl, substituted carbocycle, aryl, heteroaryl or heterocyclic, as defined above.

As used herein, the term "cyano" refers to the group —CN.

As used herein, the term "aminosulfonyl" refers to the group —$S(O)_2NH_2$. The aminosulfonyl group is optionally substituted by substituted alkyl, substituted carbocycle, aryl, heteroaryl or heterocyclic, as defined above.

As used herein, the term "sulfonylamino" refers to the group —$NHS(O)_2R_a$ where $R_a$ is substituted alkyl, substituted carbocycle, aryl, heteroaryl or heterocyclic, as defined above.

As used herein, the term "carboxyamide" refers to the group —$NHC(O)R_a$ where $R_a$ is substituted alkyl, substituted carbocycle, aryl, heteroaryl or heterocyclic, as defined above.

As used herein, the term "carboxy" refers to the group —C(O)OH. The carboxy group is optionally substituted by substituted alkyl, substituted carbocycle, aryl, heteroaryl or heterocyclic, as defined above.

As used herein, the term "aminocarbonyl" refers to the group —$C(O)NH_2$. The aminocarbonyl group is optionally substituted by substituted alkyl, substituted carbocycle, aryl, heteroaryl or heterocyclic, as defined above.

As used herein, the term "ureido" refers to the group —$NHC(O)NHR_a$ wherein $R_a$ is hydrogen, alkyl, carbocycle or aryl as defined above.

As used herein, the term "guanidino" refers to the group —NHC(=NH)$NH_2$.

As used herein, the term "acyl" refers to the group —$C(O)R_a$, where $R_a$ is alkyl, carbocycle, or heterocyclic as defined herein.

As used herein, the term "aroyl" refers to the group —$C(O)R_a$, where $R_a$ is aryl as defined herein.

As used herein, the term "heteroaroyl" refers to the group —$C(O)R_a$, where $R_a$ is heteroaryl as defined herein.

As used herein, the term "acyloxy" refers to the group —$OC(O)R_a$, where $R_a$ is alkyl, carbocycle, or heterocyclic as defined herein.

As used herein, the term "aroyloxy" refers to the group —$OC(O)R_a$, where $R_a$ is aryl as defined herein.

As used herein, the term "heteroaroyloxy" refers to the group —$OC(O)R_a$, where $R_a$ is heteroaryl as defined herein.

Also included in the present invention are pharmaceutically acceptable salts and complexes, such as the hydrochloride, hydrobromide and trifluoroacetate salts and the sodium, potassium and magnesium salts. The compounds of the present invention may contain one or more asymmetric carbon atoms and may exist in racemic and optically active forms. All of these compounds and diastereomers are contemplated to be within the scope of the present invention.

GENERAL SYNTHETIC SEQUENCE

The compounds and processes of the present invention will be better understood in connection with the following synthetic schemes, which are merely illustrative of the methods by which the compounds of the invention may be prepared and are not intended to limit the scope of the invention as defined in the appended claims.

The present invention provides compounds of Formula (1) that can be prepared from the common racemic intermediate (8), or common chiral intermediates (17) and (25).

Scheme 1.

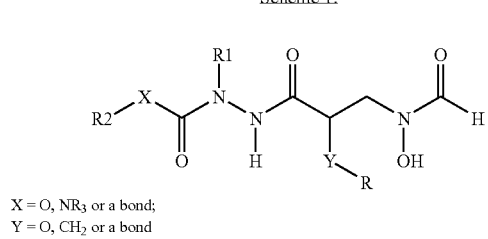

X = O, NR₃ or a bond;
Y = O, CH₂ or a bond

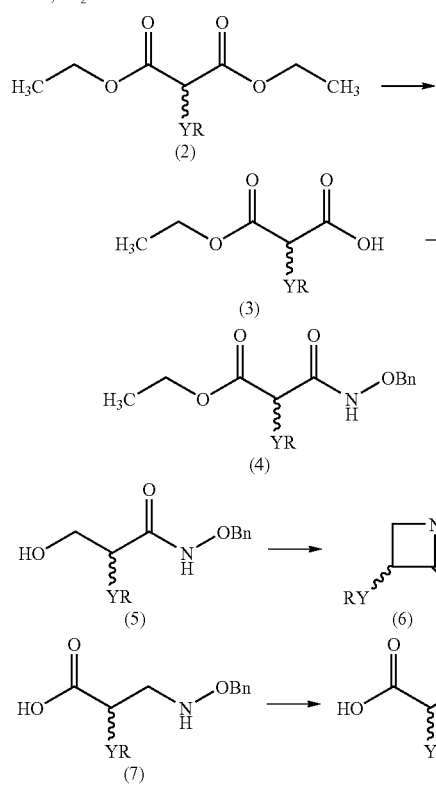

As shown in Scheme 1, intermediate (8) can be prepared by reacting the mono-substituted dialkyl malonate (2) with a base, such as potassium hydroxide, in an appropriate solvent, such as ethanol/water, to afford the mono-acid (3). Coupling of (3) with O-benzylhydroxylamine in the presence of a coupling reagent, such as 1-[3-(dimethylamino) propyl]-3-ethylcarbodiimide hydrochloride (EDCI), and a base, such as 4-dimethylaminopyridine, (DMAP) in an appropriate solvent, such as dichloromethane, gives the amide (4). Reduction of the ester functionality of compound (4) with a reducing agent, such as lithium borohydride, in an appropriate solvent, such as tetrahydrofuran, at room temperature provides the alcohol (5). Treatment of the alcohol (5) under Mitsunobu conditions affords the lactam (6). The same transformation may be achieved by treating (5) with triphenylphosphine, carbon tetrachloride and a base, such as triethylamine, to obtain (6). Hydrolysis of the lactam (6) using, for example, lithium hydroxide in an appropriate solvent mixture; such as THF-H₂O-MeOH, gives acid (7). Formylation of the amine group of (7) its achieved using formic acid and acetic anhydride in a solvent, such as dichloromethane, to provide the formylated compound (8).

Any racemates can be resolved at the level of any intermediate during the synthesis or at the level of the final product using, for example, a chiral chromatography method, to provide compound (8) in each of two enantiomeric forms.

Alternatively, an enantiomer of intermediate (8), such as (17) in Scheme 2 or (25) in Scheme 3, can be prepared by reacting an appropriate acid chloride (9) with a chiral agent, such as Evans' chiral oxazolidinone, in the presence of a base, such as n-butyl lithium, to afford the chiral intermediate (10) in Scheme 2 or (18) in Scheme 3. Treatment of the compound (10) or (18) with a base, such as diisopropylethylamine, in the presence of a chelating agent, such as titanium tetrachloride, in a solvent, such as tetrahydrofuran, followed by addition of an electrophile, such as benzyloxymethylchloride, provides either of two chiral compounds (11) and (19), depending on the selection of chiral auxiliary.

Scheme 2.

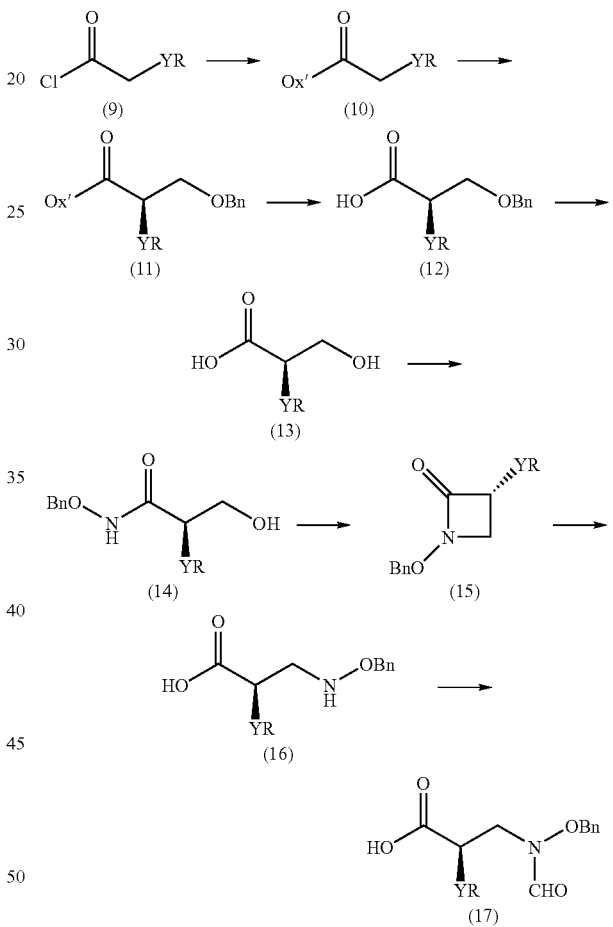

Scheme 3.

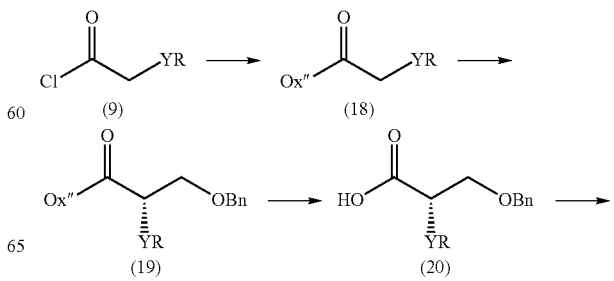

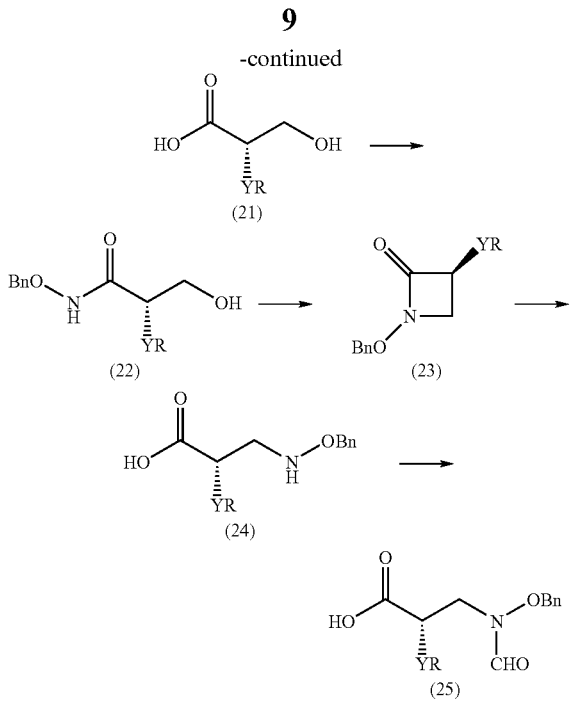

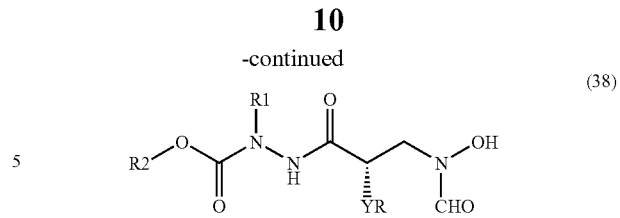

Conversion of compound (11) or (19) to the corresponding hydroxyacid (13) or (21) can be achieved by a sequence comprising oxidative cleavage of the chiral oxazolidinone, using, for example, $H_2O_2$ and lithium hydroxide to the respective intermediates (12) and (20), followed by hydrogenolysis. Coupling of the acid (13) or (21) with benzyloxyamine in the presence of coupling agents, such as EDCI/DMAP, yields the amides (14) and (22). These can be cyclized to the azetidin-2-ones (15) or (23) using either Mitsunobu conditions or a combination of triphenylphosphine/carbon tetrachloride/triethylamine. Hydrolysis of the azetidin-2-one (15) or (23), using for example lithium hydroxide, in an appropriate solvent, gives the corresponding acid (16) or (24). Conversion of compound (16) or (24) to the formate (17) or (25) can be achieved using an appropriate formylating agent, such as formic acid/acetic anhydride or methyl formate, in an appropriate solvent, such as dichloromethane.

SPECIFIC EMBODIMENTS

Second Embodiment

As the second embodiment of the present invention, the compounds of Formula (1) with X=O are disclosed, as in the racemic compound (34) and the chiral compounds (36) and (38). These compounds have preferentially R1=H.

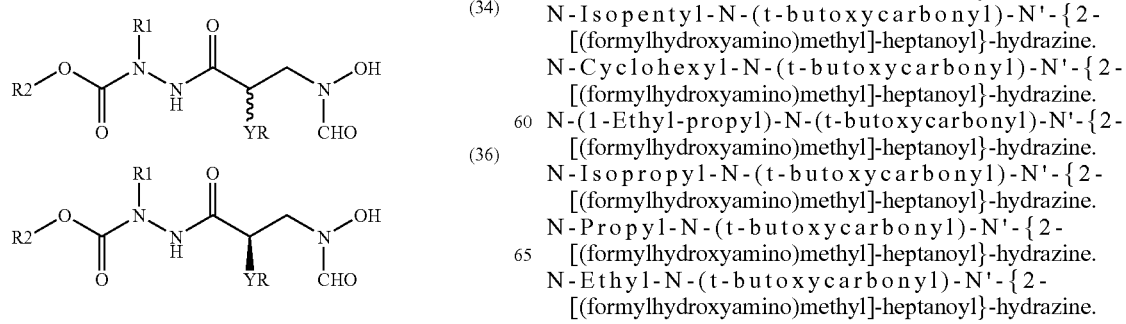

Preferred compounds useful in the present invention are selected from the group consisting of:
N-Butyl-N-(t-butoxycarbonyl)-N'-{(2R)-[(formylhydroxyamino)methyl]-heptanoyl}-hydrazine.
N-Butyl-N-phenoxycarbonyl-N'-{(2R)-[(formylhydroxyamino)methyl]-heptanoyl}-hydrazine.
N-Isobutyl-N-(t-butoxycarbonyl)-N'-{(2R)-[(formylhydroxyamino)methyl]-heptanoyl}-hydrazine.
N-Isobutyl-N-phenoxycarbonyl-N'-{(2R)-[(formylhydroxyamino)methyl]-heptanoyl}-hydrazine.
N-Phenethyl-N-(t-butoxycarbonyl)-N'-{2-[(formylhydroxyamino)methyl]-heptanoyl}-hydrazine.
N-Cyclohexylmethyl-N-(t-butoxycarbonyl)-N'-{2-[(formylhydroxyamino)methyl]-heptanoyl}-hydrazine.
N-Benzyl-N-(t-butoxycarbonyl)-N'-{2-[(formylhydroxyamino)methyl]-heptanoyl}-hydrazine.
N-(3-pyridin-3-yl-propyl)-N-(t-butoxycarbonyl)-N'-{2-[(formylhydroxyamino)methyl]-heptanoyl}-hydrazine.
N-(2-Morpholin-4-yl-ethyl)-N-(t-butoxycarbonyl)-N'{2-[(formylhydroxyamino)methyl]-heptanoyl}-hydrazine.
N-(4-Hydroxy-butyl)-N-(t-butoxycarbonyl)-N'-{2-[(formylhydroxyamino)methyl]-heptanoyl}-hydrazine.
N-(4-Amino-butyl)-N-(t-butoxycarbonyl)-N'{2-[(formylhydroxyamino)methyl]-heptanoyl}-hydrazine.
N-(Tetrahydro-pyran-4-yl)-N-(t-butoxycarbonyl)-N'-{2-[(formylhydroxyamino)methyl]-heptanoyl}-hydrazine.
N-Methyl-N-(t-butoxycarbonyl)-N'-{2-[(formylhydroxyamino)methyl]-heptanoyl}-hydrazine.
N-(3-Aminopropyl)-N-(t-butoxycarbonyl)-N'-{2-[(formylhydroxyamino)methyl]-heptanoyl}-hydrazine.
N-(t-Butoxycarbonyl)-N'-{(2R)-[(formylhydroxyamino)methyl]-heptanoyl}-hydrazine.
N-(3-Hydroxypropyl)-N-(t-butoxycarbonyl)-N'-{2-[(formylhydroxyamino)methyl]-heptanoyl}-hydrazine.
N-Butyl-N-(t-butoxycarbonyl)-N'-{(2S)-[(formylhydroxyamino)methyl]-heptanoyl}-hydrazine.
N-Butyl-N-(phenoxycarbonyl)-N'-{(2S)-[(formylhydroxyamino)methyl]-heptanoyl}-hydrazine.
N-[2-(4-Dimethylaminophenyl)ethyl]-N-(t-butoxycarbonyl)-N'-{2-[(formylhydroxyamino)methyl]-heptanoyl}-hydrazine.
N-(t-Butoxycarbonyl)-N'-{2-[(formylhydroxyamino)methyl]-heptanoyl}-hydrazine.
N-Pentyl-N-(t-butoxycarbonyl)-N'-{2-[(formylhydroxyamino)methyl]-heptanoyl}-hydrazine.
N-[2-(1H-Indol-3-yl)-ethyl]-N-(t-butoxycarbonyl)-N'-{2-[(formylhydroxyamino)methyl]-heptanoyl}-hydrazine.
N-Isopentyl-N-(t-butoxycarbonyl)-N'-{2-[(formylhydroxyamino)methyl]-heptanoyl}-hydrazine.
N-Cyclohexyl-N-(t-butoxycarbonyl)-N'-{2-[(formylhydroxyamino)methyl]-heptanoyl}-hydrazine.
N-(1-Ethyl-propyl)-N-(t-butoxycarbonyl)-N'-{2-[(formylhydroxyamino)methyl]-heptanoyl}-hydrazine.
N-Isopropyl-N-(t-butoxycarbonyl)-N'-{2-[(formylhydroxyamino)methyl]-heptanoyl}-hydrazine.
N-Propyl-N-(t-butoxycarbonyl)-N'-{2-[(formylhydroxyamino)methyl]-heptanoyl}-hydrazine.
N-Ethyl-N-(t-butoxycarbonyl)-N'-{2-[(formylhydroxyamino)methyl]-heptanoyl}-hydrazine.

N-Methoxycarbonyl-N'-{2[(formylhydroxyamino)methyl]-heptanoyl}-hydrazine.

N-{[1-(3,5-Dimethoxyphenyl)-1-methyl-ethoxy]carbonyl}-N'-{2-[(formylhydroxyamino)methyl]-heptanoyl}-hydrazine.

The following synthetic schemes are merely illustrative of the methods by which the compounds of the invention may be prepared and are not intended to limit the scope of the invention as defined in the appended claims.

As shown in Scheme 4, treatment of the alkyl halide R1X (26) with hydrazine in a solvent such as ethanol, at an elevated temperature, gives hydrazine derivative (27). Reacting (27) with the carbonate R2OC(O)OC(O)OR2 or the chloroformate R2OCOCl affords the intermediate (28). Alternatively, (28) can be prepared from the Boc-protected hydrazine (29) by reaction with the aldehyde or ketone R'COR", followed by reduction with hydrogen gas in the presence of palladium, to afford hydrazine derivative (30). Reacting hydrazine (30) with a carbonate R2OC(O)OC(O)OR2 or a chloroformate R2OCOCl, followed by removal of the Boc protecting group with an appropriate acid, such as trifluoroacetic acid, gives the hydrazine derivative (28) wherein R1=CHR'R". Alternatively, the primary amino group of (29) can be protected as the phthalimide (31). Reacting the compound (31) with an alcohol under Mitsunobu conditions gives compound (32), which, upon hydrazinolysis, is readily converted to a hydrazine of Formula (10) where R2=t-butyl.

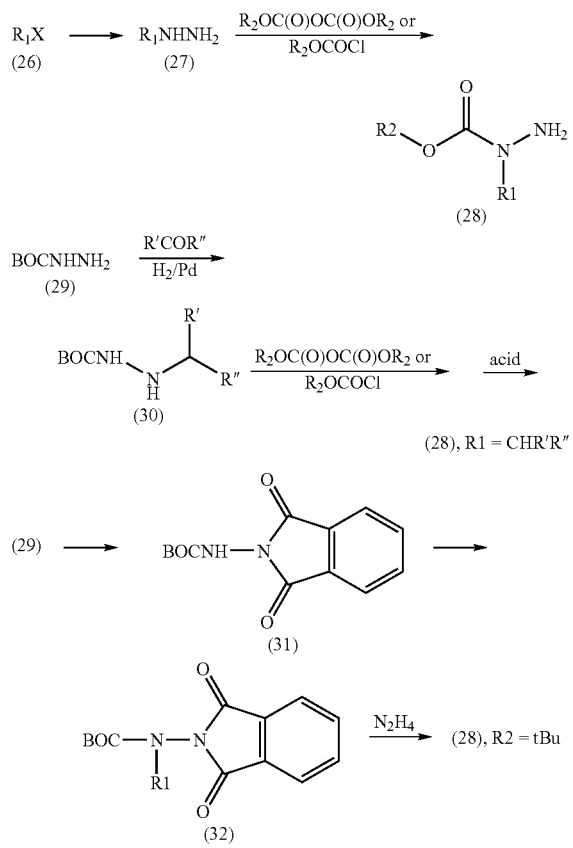

As shown in Scheme 5, coupling of the acid (8) with the hydrazine derivative (28) using conditions such as DMAP/EDCI or EDCI/HOAt/NMM provides the hydrazide (33). Hydrogenolysis to remove the benzyl group using a catalyst, such as 10% Pd/C, in an appropriate solvent, such as ethanol, gives desired compound (34). Similarly, coupling of the chiral acid (17) or (25) with the hydrazine derivative (28) provides the corresponding hydrazide (35) or (37). Hydrogenolysis of the benzyl group gives the final desired compound (36) or (38).

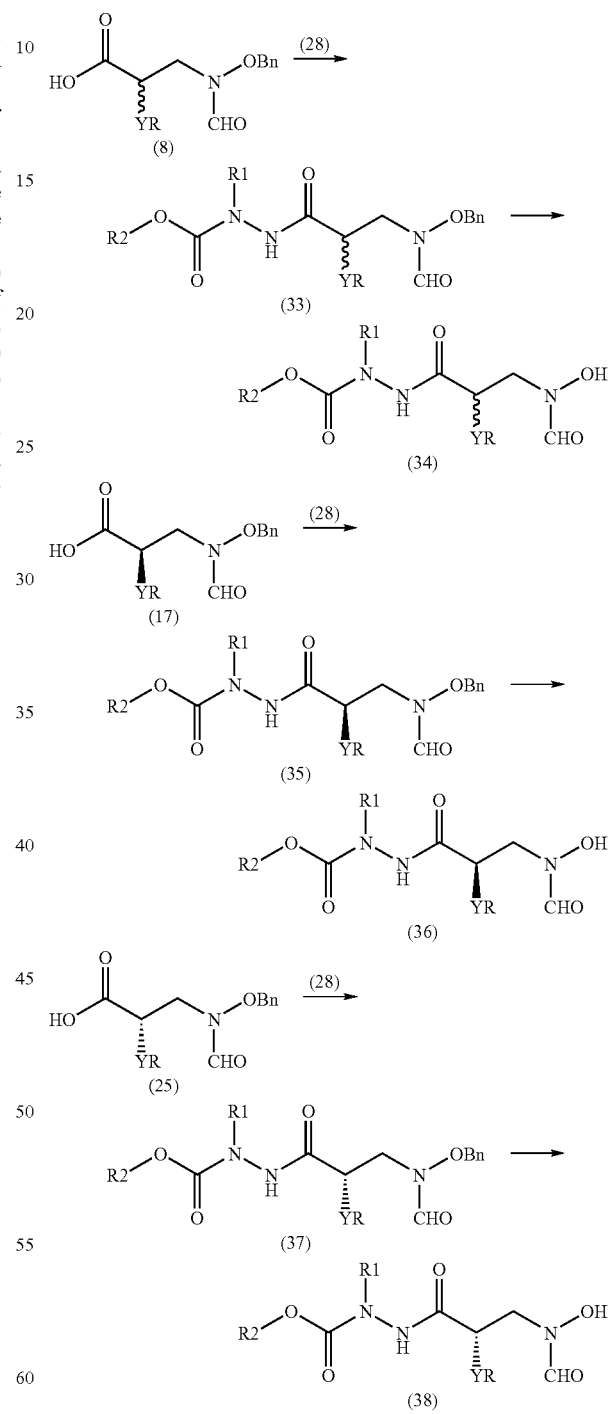

SYNTHETIC EXAMPLES

The invention will now be described by reference to the following examples which are merely illustrative and are not to be construed as a limitation of the scope of the present invention.

As used herein the symbols and conventions used in these processes, schemes and examples are consistent with those used in the contemporary scientific literature, for example, the *Journal of the American Chemical Society or the Journal of Biological Chemistry*. Standard single-letter or three-letter abbreviations are generally used to designate amino acid residues, which are assumed to be in the L-configuration unless otherwise noted. Unless otherwise noted, all starting materials were obtained from commercial suppliers and used without further purification.

Hz (Hertz); TLC (thin layer chromatography);
$T_r$ (retention time); RP (reverse phase);
MeOH (methanol); i-PrOH (isopropanol);
EtOH (ethanol); TEA (triethylamine);
TFA (trifluoroacetic acid); THF (tetrahydrofuran);
DMSO (dimethylsulfoxide); AcOEt or EtOAc (ethyl acetate);
DCM (dichloromethane); DMF (N,N-dimethylformamide);
CDI (1,1-carbonyldiimidazole); HOAc (acetic acid);
HOSu (N-hydroxysuccinimide); Ac (acetyl);
HOBT (1-hydroxybenzotriazole); BOC (tert-butyloxycarbonyl);
mCPBA (meta-chloroperbenzoic acid); FMOC (9-fluorenylmethoxycarbonyl);
DCC (dicyclohexylcarbodiimide); CBZ (benzyloxycarbonyl);
NMM (N-methyl morpholine); HOAt (1-hydroxy-7-azabenzotriazole);
DMAP (4-dimethylaminopyridine); Bn (benzyl);
TBAF (tetra-n-butylammonium fluoride);
HPLC (high pressure liquid chromatography);
BOP (bis(2-oxo-3-oxazolidinyl)phosphinic chloride);
EDCI (1-ethyl-3-[3-dimethylaminopropyl]carbodiimide hydrochloride);
HBTU (O-Benzotriazole-1-yl-N,N,N',N'-tetramethyluronium hexafluorophosphate).

All references to ether are to diethyl ether; brine refers to a saturated aqueous solution of NaCl. Unless otherwise indicated, all temperatures are expressed in ° C. (degrees Centigrade). All reactions are conducted under an inert atmosphere at room temperature unless otherwise noted, and all solvents are highest available purity unless otherwise indicated.

$^1$H NMR (hereinafter also "NMR") spectra were recorded on a Varian VXR-300, a Varian Unity-300, a Varian Unity-400 instrument, a Brucker AVANCE-400, a General Electric QE-300 or a Bruker AM 400 spectrometer. Chemical shifts are expressed in parts per million (ppm, δ units). Coupling constants are in units of hertz (Hz). Splitting patterns describe apparent multiplicities and are designated as s (singlet), d (doublet), t (triplet), q (quartet), quint (quintet), m (multiplet), br (broad).

Mass spectra were run on an open access LC-MS system using electrospray ionization. LC conditions: 4.5% to 90% $CH_3CN$ (0.02% TFA) in 3.2 min with a 0.4 min hold and 1.4 min re-equilibration; detection by MS, UV at 214 nm, and a light scattering detector (ELS). Column: 1×40 mm Aquasil (C18).

For preparative (prep) hplc; ca 50 mg of the final products were injected in 500 uL of DMSO onto a 50×20 mm I. D. YMC CombiPrep ODS-A column at 20 mL/min with a 10 min gradient from 10% $CH_3CN$ (0.1% TFA) to 90% $CH_3CN$ (0.1% TFA) in $H_2O$ (0.1% TFA) and a 2 min hold. Flash chromatography was run over Merck Silica gel 60 (230–400 mesh).

Infrared (IR) spectra were obtained on a Nicolet 510 FT-IR spectrometer using a 1-mm NaCl cell. Most of the reactions were monitored by thin-layer chromatography on 0.25 mm E. Merck silica gel plates (60F-254), visualized with UV light, 5% ethanolic phosphomolybdic acid or p-anisaldehyde solution.

The compounds disclosed in Examples 2 to 30 were prepared following the general procedures described in Example 1.

Preparation 1

(4S)-Benzyl-3-heptanoyl-oxazolidin-2-one

To a solution of (S)-(−)-4-benzyl-2-oxazolidinone (3.3 g, 18.6 mmol) in THF (50 mL) at −78° C. was added dropwise n-BuLi (7.4 mL, 2.5M solution in hexane, 18.6 mmol). After stirring for 30 min at the same temperature, the reaction mixture was then treated with heptanoyl chloride (2.76 g, 18.6 mmol). The reaction mixture was stirred and allowed to warm to 10° C. over 5 h, and then quenched with saturated aqueous $NH_4Cl$ solution (100 mL). The aqueous layer was extracted with EtOAc (100 mL×2). The combined organic layers were washed with brine, and dried over $MgSO_4$. Removal of the solvent under reduced pressure yielded 4.63 g (86%) of the title compound. $^1$H NMR (400 MHz, $CDCl_3$) δ 7.37–7.22 (m, 5H), 4.69 (m, 1H), 4.19 (m, 2H), 3.31 (dd, J=13.4, 3.3 Hz, 1H), 2.95 (m, 2H), 2.79 (dd, J=13.4, 9.7 Hz, 1H), 1.71 (m, 2H), 1.42–1.32 (m, 6H), 0.92 (t, J=6.8 Hz, 3H). MH+290.

Preparation 2

(4S)-Benzyl-3-[(2R)-benzyloxymethylheptanoyl]oxazolidin-2-one

To a solution of (S)-4-benzyl-3-heptanoyloxazolidin-2-one (4.63 g, 16.02 mmol) and titanium(IV) chloride (1.9 mL, 16.82 mmol) in dichloromethane (55 mL) at 0° C. was added dropwise diisopropylethylamine (3.1 mL, 17.62 mmol). After stirring at 0° C. for 1 hour, the resulting titanium enolate was then reacted with benzylchloromethyl ether (TCI-America, 4.9 mL, 32.04 mmol) at 0° C. for 6 h. The reaction mixture was then quenched with water (100 mL). The aqueous layer was extracted with dichloromethane (100 mL×2). The organic extracts were washed with brine, and dried over $MgSO_4$. After removing the solvent under reduced pressure, purification by flash column chromatography using an eluting system of hexane/EtOAc (5:1) yielded 4.39 g (67%) of the title compound. $^1$H NMR (400 MHz, $CDCl_3$) δ 7.38–7.21 (m, 10H), 4.74 (m, 1H), 4.57 (m, 2H), 4.28–4.13 (m, 3H), 3.82 (t, J=8.7 Hz, 1H), 3.68 (dd, J=9.0, 4.9 Hz, 1H), 3.25 (dd, J=13.5, 3.1 Hz, 1H), 2.71 (dd, J=13.5, 9.3 Hz, 1H), 1.74 (m, 1H), 1.54 (m, 1H), 1.31–1.28 (m, 6H), 0.89 (t, J=6.7 Hz, 3H). MH+410.

Preparation 3

(3R)-Benzyloxy-2-pentylpropionic acid

A 0.05 M solution of (S)-4-benzyl-3-[(R)-2-benzyloxymethylheptanoyl]oxazolidin-2-one (2.0 g, 4.89 mmol) in a 3:1 mixture of THF and $H_2O$ was treated with 30% $H_2O_2$ (4.5 mL, 39.12 mmol), followed by LiOH (0.48 g, 9.78 mmol) at 0° C. The resulting mixture was stirred and allowed to warm to room temperature overnight. THF was then removed under vacuum. The residue was washed with dichloromethane (50 mL×2) to remove (S)-4-benzyloxazolidin-2-one. The desired product was isolated by EtOAc extraction of the acidified (pH 1~2) aqueous phase. No further purification was required. Standing under high vacuum yielded 1.16 g (95%) of the title compound. $^1$H NMR (400 MHz, CHCl$_3$) δ 11.1 (br s, 1H), 7.36 (m, 5H), 4.57 (s, 2H), 3.69 (m, 1H), 3.58 (dd, J=9.2, 5.2 Hz, 1H), 2.74 (m, 1H), 1.66 (m, 1H), 1.54 (m, 1H), 1.34–1.30 (m, 6H), 0.90 (t, J=6.7 Hz, 3H). MH+251.

Preparation 4

3-Hydroxy-(2R)-pentylpropionic acid

To a solution of (R)-3-benzyloxy-2-pentyl-propionic acid (1.54 g, 6.16 mmol) in EtOH (100 mL) was added 10% Pd/C (310 mg). The reaction mixture was subjected to hydrogenation overnight at room temperature. After the reaction was completed, the reaction mixture was filtered through a pad of Celite, and washed with EtOH (50 mL×3). Removal of the solvent provided the title compound (0.92 g, 93%). No further purification was required. $^1$H NMR (400 MHz, CHCl$_3$) δ 6.30 (br s, 1H), 3.81 (d, J=5.4 Hz, 2H), 2.64 (m, 1H), 1.69 (m, 1H), 1.56 (m, 1H), 1.41–1.27 (m, 6H), 0.91 (t, J=7.7 Hz, 3H). MH+161.

Preparation 5

N-Benzyloxy-3-hydroxy-(2R)-pentylpropionamide

To a mixture of (R)-3-hydroxy-2-pentylpropionic acid (0.92 g, 5.75 mmol), O-benzyl hydroxylamine hydrochloride (0.92 g, 5.75 mmol) and 4-(dimethylamino)pyridine (1.41 g, 11.50 mmol) in dichloromethane (25 mL) at 0° C. was added 1-[3-(dimethylamino)propyl]-3-ethylcarbodiimide hydrochloride (1.11 g, 5.75 mmol). After stirring at room temperature overnight, the reaction was then quenched with 1N aqueous HCl solution (25 mL) and extracted using dichloromethane (25 mL×2). The organic extracts were washed with water, brine, and dried over MgSO$_4$. Removal of the solvent under reduced pressure yielded the title compound (1.43 g, 94%). $^1$H NMR (400 MHz, CHCl$_3$) δ 9.22 (br s, 1H), 7.41–7.28 (m, 5H), 4.89 (q, J=10.6 Hz, 2H), 3.70–3.37 (m, 3H), 2.17 (m, 1H), 1.54 (br s, 1H), 1.27 (m, 6H), 0.88 (t, J=6.9 Hz, 3H). MH+266.

Preparation 6

1-benzyloxy-(3R)-pentylazetidin-2-one

To a mixture of (R)-N-benzyloxy-3-hydroxy-2-pentylpropionamide (1.41 g, 5.32 mmol) and triphenylphosphine (1.68 g, 6.39 mmol) in THF (53 mL) was added dropwise diethyl azodicarboxylate (1.1 mL, 6.39 mmol) at 0° C. The reaction mixture was stirred and allowed to warm to room temperature overnight. The reaction was then quenched with water (50 mL). The aqueous layer was extracted with EtOAc (50 mL×2). The combined organic layers were washed with brine, and dried over MgSO$_4$. After removing the solvent under vacuum, the residue was purified by flash column chromatography (hex:EtOAc 5/1) to provide the title compound (1.17 g, 89%). $^1$H NMR (400 MHz, CHCl$_3$) δ 7.35–7.25 (m, 5H), 4.87 (s, 2H), 3.28 (t, J=4.85 Hx, 1H), 2.84 (q, J=2.35 Hz, 1H), 2.77 (m, 1H), 1.62 (m, 1H), 1.36 (m, 1H), 1.25–1.16 (m, 6H), 0.88 (t, J=6.9 Hz, 3H). MH+248.

Preparation 7

3-benzyloxyamino-(2R)-pentylpropionic acid

To a mixture of (R)-1-benzyloxy-3-pentylazetidin-2-one (0.96 g, 3.89 mmol) in a mixture of THF-H$_2$O-MeOH (50 mL, 3:1:1 v/v) was added lithium hydroxide monohydrate (1.91 g, 38.9 mmol). After stirring at room temperature overnight, water (25 mL) was added to the mixture. The solution was acidified to pH 5~6 with 3N aqueous HCl solution. It was extracted with EtOAc (50 mL×2). The combined organic layers were dried over MgSO$_4$: Removal of the solvent under vacuum provided the title compound (0.98 g, 95%). $^1$H NMR (400 MHz, CHCl$_3$) δ 9.80 (br s, 1H), 7.37 (m, 5H), 4.75 (m, 2H), 3.14 (m, 2H), 2.74 (m, 1H), 1.70 (m, 1H), 1.53 (m, 1H), 1.38–1.25 (m, 6H), 0.91 (t, J=6.8 Hz, 3H). MH+266.

Preparation 8

(2R)-[(benzyloxyformylamino)methyl]heptanoic acid

To a cold solution of (R)-3-Benzyloxyamino-2-pentylpropionic acid (1.03 g, 3.89 mmol) in HCO$_2$H (19 mL) and dichloromethane (19 mL) at 0° C. was added acetic anhydride (3.9 mL, 41.2 mmol). The mixture was stirred at 0° C. for 3 hours. The volatiles were removed by evaporation under vacuum. Dichloromethane (50 mL) was added to it. It was washed with brine (50 mL×2), and dried over MgSO$_4$. Filtration and evaporation under vacuum provided the title compound (1.08 g, 95%). $^1$H NMR (400 MHz, CHCl$_3$) δ 8.07 (br s, 1H), 7.29 (m, 5H), 4.91–4.71 (m, 2H), 3.76 (m, 2H), 2.67 (m, 1H), 1.54 (m, 1H), 1.41(m, 1H), 1.20 (m, 6H), 0.80 (t, J=7.0 Hz, 3H). MH+294.

Preparation 9

Butylhydrazine

1-Iodobutane (5.1 mL, 45.1 mmol) was added through a condenser for 30 min to a refluxing solution of hydrazine inonohydrate (11.3 g, 225.5 mmol) in EtOH (100 mL). After stirring and refluxing for 18 hours, ethanol was removed by evaporation under vacuum. The residue was extracted with ether (50 mL×2). The combined organic layers were dried (K$_2$CO$_3$), filtered and evaporated to yield 2.6 g (66%) of the title compound. $^1$H NMR (400 MHz, CHCl$_3$) δ 3.15 (br s, 2H), 2.73 (t, J=7.2 Hz, 2H), 1.44 (m, 2H), 1.33 (m, 2H), 0.89 (t, J=7.2 Hz, 3H). MH+89.

Preparation 10

N-Butylhydrazinecarboxylic acid tert-buyl ester

To a solution of butylhydrazine (510 mg, 5.80 mmol) and triethylamine (1.2 mL, 8.69 mmol) in dichloromethane (20 mL) at 0° C. was added di-t-butyl dicarbonate (1.26 g, 5.80 mmol). The reaction mixture was stirred and allowed to warm up to room temperature overnight. Water (20 mL) was then added to the reaction mixture. The aqueous layer was extracted with dichloromethane (20 mL×2). The combined organic layers were dried (MgSO$_4$). Filtration and evaporation under vacuum provided the title compound (820 mg, 75%). $^1$H NMR (400 MHz, CHCl$_3$) δ 3.89 (br s, 2H), 3.29 (t, J=7.1 Hz, 2H), 1.46 (m, 2H), 1.40 (s, 9H), 1.24 (m, 2H), 0.86 (t, J=7.3 Hz, 3H). MH+189.

Preparation 11

N-Butyl-N-(t-butoxycarbonyl)-N'-{(2R)-[(benzyloxyformylamino)methyl]heptanoyl}-hydrazine To a solution of (R)-2-[(benzyloxyformyl-amino)methyl] heptanoic acid (180 mg, 0.614 mmol), N-butylhydrazinecarboxylic acid tert-buyl ester (140 mg, 0.737 mmol) and 4-dimethylaminopyridine (90 mg, 0.737 mmol) in dichloromethane (6.5 mL) at 0° C. was added 1-[3-(dimethylamino)propyl]-3-ethylcarbodiimide hydrochloride (142 mg, 0.737 mmol). After stirring at room temperature overnight, the reaction was then quenched with aqueous 1N HCl and extracted with dichloromethane (15 mL×2). The organic extracts were washed with brine (30 mL), and dried over MgSO$_4$. Evaporation of the solvent under vacuum, followed by purification by flash column chromatography yielded 195 mg (69%) of the title compound. $^1$H NMR (400 MHz, CHCl$_3$) δ 8.09 (br s, 1H), 7.25 (s, 5H), 4.80 (m, 2H), 4.10 (dd, J=14.1, 4.0 Hz, 1H), 3.62 (m, 1H), 3.35 (m, 2H), 2.55 (m, 1H), 1.72 (m, 1H), 1.56 (m, 1H), 1.50 (s, 9H), 1.30 (m, 10H), 0.90 (m, 6H). MH+464.

Example 1

N-Butyl-N-(t-butoxycarbonyl)-N'-{(2R)-[(formylhydroxyamino)methyl]-heptanoyl}-hydrazine To a solution of N'-{(R)-2-[(benzyloxy-formylamino)methyl]heptanoyl}-N-butylhydrazine carboxylic acid tert-buyl ester (195 mg, 0.421 mmol) in EtOH (15 mL) was added 10% Pd/C (60 mg). The reaction mixture was subjected to hydrogenation overnight at room temperature. After the reaction was completed, the reaction mixture was filtered through a pad of Celite, and washed with EtOH (10 mL×2). Removal of the solvent provided the crude product, which was further purified by HPLC to yield the title compound (52 mg, 33%). $^1$H NMR (400 MHz, CHCl$_3$) δ 9.94 (s, 1H), 9.39 (s, 1H), 8.32 (s, 1H), 4.10 (dd, J=14.1, 4.0 Hz, 1H), 3.62 (m, 1H), 3.35 (m, 2H), 2.55 (m, 1H), 1.72 (m, 1H), 1.56 (m, 1H), 1.50 (s, 9H), 1.30 (m, 10H), 0.90 (m, 6H). MH+374.

Preparation 12

N-Butylhydrazinecarboxylic acid phenyl ester

To a solution of butylhydrazine (370 mg, 4.20 mmol) and triethylamine (0.88 mL, 6.30 mmol) in dichloromethane (15 mL) at 0° C. was added phenyl chloroformate (0.53 mL, 4.20 mmol). The reaction mixture was stirred and allowed to warm up to room temperature overnight. Water (20 mL) was then added to the reaction mixture. The aqueous layer was extracted with dichloromethane (20 mL×2). The combined organic layers were dried (MgSO$_4$). Filtration and evaporation under vacuum, followed by purification by flash column chromatography provided the title compound (250 mg, 29%). $^1$H NMR (400 MHz, CHCl$_3$) δ 7.40–7.10 (m, 5H), 4.20 (t, J=7.1 Hz, 2H), 3.60 (br s, 2H), 1.71 (m, 2H), 1.41 (m, 2H), 0.98 (t, J=7.3 Hz, 3H). MH+209.

Example 2

N-Butyl-N-phenoxycarbonyl-N'-{(2R)-[(formylhydroxyamino)methyl]-heptanoyl}-hydrazine Purification by preparative HPLC yielded 49 mg (41%) of the title compound. $^1$H NMR (400 MHz, CHCl$_3$) δ 9.78 (s, 1H), 9.39 (s, 1H), 8.27 (s, 1H), 7.40–7.10 (m, 5H), 4.20–3.30 (m, 4H), 2.70 (m, 1H), 1.80–1.20 (m, 10H), 0.90 (m, 6H). MH+394.

Example 3

N-Isobutyl-N-(t-butoxycarbonyl)-N'-{(2R)-[(formylhydroxyamino)methyl]-heptanoyl}-hydrazine Purification by preparative HPLC yielded 44 mg (22%, 2 steps) of the title compound. $^1$H NMR (400 MHz, CHCl$_3$) δ 9.94 (s, 1H), 9.54 (s, 1H), 8.32 (s, 1H), 4.11 (dd, J=3.9, 14.1 Hz, 1H), 3.46 (m, 1H), 3.35 (m, 1H), 3.12 (dd, J=6.3, 14.1 Hz, 1H), 2.54 (m, 1H), 1.88 (m, 1H), 1.72 (m, 1H), 1.50 (s, 9H), 1.49–1.25 (m, 7H), 0.95–0.88 (m, 9H). MH+374.

Example 4

N-Isobutyl-N-phenoxycarbonyl-N'-{(2R)-[(formylhydroxyamino)methyl]-heptanoyl}-hydrazine Purification by preparative HPLC yielded 44 mg (22%, 2 steps) of the title compound. $^1$H NMR (400 MHz, CHCl$_3$) δ 9.97 (s, 1H), 9.38 (s, 1H), 8.27 (s, 1H), 7.41–7.13 (m, 5H), 4.08 (dd, J=3.9, 14.1 Hz, 1H), 3.37 (m, 2H), 2.65 (m, 1H), 2.02 (m, 1H), 1.74 (m, 1H), 1.32–1.02 (m, 7H), 0.92–0.82 (m, 9H). MH+394.

Example 5

N-Phenethyl-N-(t-butoxycarbonyl)-N'-{2-[(formylhydroxyamino)methyl]-heptanoyl}-hydrazine $^1$H NMR (400 MHz, CDCl$_3$) δ 9.80 (s, 1H), 9.03 (s, 1H), 8.35 (s, 1H), 7.22 (s, 5H), 4.11–3.36 (m, 4H), 2.86 (t, 3H), 2.52 (m, 1H), 2.07 (m, 1H), 1.72 (m, 1H), 1.41–1.34 (m, 15H), 0.92 (t, 3H). MH+422.

Example 6

N-Cyclohexylmethyl-N-(t-butoxycarbonyl)-N'-{2-[(formylhydroxyamino)methyl]-heptanoyl}-hydrazine $^1$H NMR (400 MHz, CDCl$_3$) δ 8.44 (s, 1H), 7.70 (br s, 1H), 4.20–3.05 (m, 4H), 2.50 (m, 1H), 1.74–0.90 (m, 31H). MH+414.

Example 7

N-Benzyl-N-(t-butoxycarbonyl)-N'-{2-[(formylhydroxyamino)methyl]-heptanoyl}-hydrazine $^1$H NMR (400 MHz, CDCl$_3$) δ 9.70 (br s, 1H), 8.77 (br s, 1H), 8.25 (s, 1H), 7.64–7.28 (m, 5H), 5.00 (d, J=14.7 Hz, 1H), 2.40 (m, 1H), 1.66 (m, 1H), 1.56 (m, 1H), 1.52 (s, 9H), 1.48–1.10 (m, 6H), 0.87 (t, J=7.1 Hz, 3H). MH+408.

Example 8

N-(3-pyridin-3-yl-propyl)-N-(t-butoxycarbonyl)-N'-{2-[(formylhydroxyamino)methyl]-heptanoyl}-hydrazine $^1$H NMR (400 MHz, CDCl$_3$) δ 8.79–7.25 (m, 5H), 4.15–3.03 (m, 4H), 2.75 (m, 1H), 2.56 (m, 2H), 2.07–1.72 (m, 4H), 1.49 (s, 9H), 1.46–1.28 (m, 6H), 0.85 (t, J=6.9 Hz, 3H). MH+437.

Example 9

N-(2-Morpholin-4-yl-ethyl)-N-(t-butoxycarbonyl)-N'-{2-[(formylhydroxyamino)methyl]-heptanoyl}-hydrazine $^1$H NMR (400 MHz, CDCl$_3$) δ 8.45 (br s, 1H), 7.88 (br s, 1H), 4.20–3.30 (m, 8H), 2.70 (m, 1H), 2.60–2.45 (m, 6H), 1.72 (m, 1H), 1.50 (s, 9H), 1.39 (m, 1H), 1.29 (m, 6H), 0.89 (t, J=7.1 Hz, 3H). MH+431.

Example 10

N-(4-Hydroxy-butyl)-N-(t-butoxycarbonyl)-N'-{2-[(formylhydroxyamino)methyl]-heptanoyl}-hydrazine $^1$H NMR (400 MHz, CDCl$_3$) δ 9.04 (br s, 1H), 8.37 (br s, 1H), 4.07–3.46 (m, 6H), 2.54 (m, 1H), 1.64–1.30 (m, 12H), 1.47 (s, 9H), 0.89 (t, J=6.9 Hz, 3H). MH+390.

Example 11

N-(4-Amino-butyl)-N-(t-butoxycarbonyl)-N'-{2-[(formylhydroxyamino)methyl]-heptanoyl}-hydrazine $^1$H NMR (400 MHz, CD$_3$OD) δ 7.90 (s, 1H), 7.70 (s, 1H), 4.00 (m, 2H), 3.70–3.40 (m, 4H), 3.0 (m, 2H), 2.50 (m, 1H), 1.70 (m, 1H), 1.50 (m, 1H), 1.49 (s, 9H), 1.48–1.20 (m, 10H), 0.89 (t, J=6.9 Hz, 3H). MH+389.

Example 12

N-(Tetrahydro-pyran-4-yl)-N-(t-butoxycarbonyl)-N'-{2-[(formylhydroxyamino)methyl]-heptanoyl}-hydrazine $^1$H NMR (400 MHz, CDCl$_3$) δ 9.88 (br s, 1H), 8.31 (s, 1H), 4.16–4.00 (m, 4H), 3.44–3.39 (m, 3H), 2.60 (m, 1H), 1.97–1.26 (m, 12H), 0.90 (t, J=6.9 Hz, 3H). MH+402.

Example 13

N-Methyl-N-(t-butoxycarbonyl)-N'-{2-[(formylhydroxyamino)methyl]-heptanoyl}-hydrazine $^1$H NMR (400 MHz, CDCl$_3$) δ 9.74 (br s, 1H), 8.90 (br s, 1H), 8.29 (br s, 1H), 4.06 (m, 1H), 3.24 (m, 1H), 3.10 (s, 3H), 2.43 (m, 1H), 1.64 (m, 1H), 1.42 (s, 9H), 1.31 (m, 1H), 1.19 (m, 6H), 0.79 (t, J=6.9 Hz, 3H). MH+332.

Example 14

N-(3-Amino-propyl)-N-(t-butoxycarbonyl)-N'-{2-[(formylhydroxyamino)methyl]-heptanoyl}-hydrazine $^1$H NMR (400 MHz, CDCl$_3$) δ 8.27 (s, 1H), 7.78 (s, 1H), 3.76–3.32 (m, 4H), 2.84 (m, 2H), 2.68 (m, 1H), 1.80 (m, 1H), 1.74 (m, 1H), 1.48 (s, 9H), 1.35 (m, 8H), 0.93 (t, J=6.8 Hz, 3H). MH+375.

Example 15

N-(t-Butoxycarbonyl)-N'-{(2R)-[(formylhydroxyamino)methyl]-heptanoyl}-hydrazine $^1$H NMR (400 MHz, CDCl$_3$) δ 9.53 (s, 1H), 8.17 (s, 1H), 6.68 (s, 1H), 4.11 (m, 1H), 3.38 (m, 1H), 2.63 (m, 1H), 1.70 (m, 1H), 1.49 (s, 9H), 1.42 (m, 1H), 1.29 (m, 6H), 0.87 (t, J=6.8 Hz, 3H). MH+318.

Example 16

N-(3-Hydroxy-propyl)-N-(t-butoxycarbonyl)-N'-{2-[(formylhydroxyamino)methyl]-heptanoyl}-hydrazine $^1$H NMR (400 MHz, CDCl$_3$) δ 9.34 (s, 1H), 8.33 (s, 1H), 7.83 (s, 1H), 3.83–3.43 (m, 6H), 2.81 (m, 1H), 1.78–1.65 (m, 2H), 1.52–1.29 (m, 8H), 1.45 (s, 9H), 0.87 (m, 9H). MH+376.

Example 17

N-Butyl-N-(t-butoxycarbonyl)-N'-{(2S)-[(formylhydroxyamino)methyl]-heptanoyl}-hydrazine

MH+374.

Example 18

N-Butyl-N-(phenoxycarbonyl)-N'-{(2S)-[(formylhydroxyamino)methyl]-heptanoyl}-hydrazine $^1$H NMR (400 MHz, CDCl$_3$) δ 9.27 (s, 1H), 8.20 (s, 1H), 7.32–7.04 (m, 5H), 3.80–3.31 (m, 4H), 2.55 (s, 1H), 1.66 (s, 1H), 1.59–1.24 (m, 11H), 0.90–0.82 (m, 6H), MH+394.

Example 19

N-[2-(4-Dimethylaminophenyl)ethyl]-N-(t-butoxycarbonyl)-N'-{2-[(formylhydroxyamino)methyl]-heptanoyl}-hydrazine $^1$H NMR (400 MHz, CDCl$_3$) δ 9.81 (s, 1H), 8.89 (s, 1H), 8.33 (s, 1H), 7.06 (d, J=8.5 Hz, 2H), 6.71 (d, J=8.5 Hz, 2H), 4.17–3.33 (m, 4H), 2.93 (s, 6H), 2.80 (m, 2H), 2.48 (m, 1H), 1.71 (m, 1H), 1.41 (s, 9H), 1.32 (m, 7H), 0.91 (t, 3H). MH+465.

Example 20

N-(t-Butoxycarbonyl)-N'-{2-[(formylhydroxyamino)methyl]-heptanoyl}-hydrazine $^1$H NMR (400 MHz, CDCl$_3$) δ 9.81 (s, 1H), 9.54 (s, 1H), 8.46 (s, 1H), 6.78 (s, 1H), 3.85–3.37 (m, 2H), 2.80–2.62 (m, 1H), 1.71 (m, 1H), 1.49 (s, 9H), 1.30–1.25 (m, 7H), 0.89 (t, 3H). MH+318.

Example 21

N-Pentyl-N-(t-butoxycarbonyl)-N'-{2-[(formylhydroxyamino)methyl]-heptanoyl}-hydrazine $^1$H NMR (400 MHz, CDCl$_3$) δ 9.10 (s, 1H), 8.43 (s, 1H), 4.14–3.05 (m, 4H), 2.86–2.48 (m, 1H), 1.61 (m, 1H), 1.41 (m, 9H), 1.25–1.16 (m, 13H), 0.84 (m, 6H). MH+388.

Example 22

N-[2-(1H-Indol-3-yl)-ethyl]-N-(t-butoxycarbonyl)-N'-{2-[(formylhydroxyamino)methyl]-heptanoyl}-hydrazine $^1$H NMR (400 MHz, CDCl$_3$) δ 9.78 (s, 1H), 8.55 (s, 1H), 8.33 (s, 1H), 8.15 (s, 1H), 7.55–7.05 (m, 5H), 4.10–3.92 (m, 2H), 3.71–3.30 (m, 2H), 3.02 (m, 2H), 2.40 (m, 1H), 1.67 (m, 1H), 1.50–1.20 (m, 16H), 0.89 (m, 6H). MH+461.

Example 23

N-Isopentyl-N-(t-butoxycarbonyl)-N'-{2-[(formylhydroxyamino)methyl]-heptanoyl}-hydrazine $^1$H NMR (400 MHz, CDCl$_3$) δ 9.92 (s, 1H), 8.39 (s, 1H), 4.05–3.63 (m, 2H), 3.31 (t, 2H), 2.54 (m, 1H), 1.70 (m, 1H), 1.55 (m, 1H), 1.50–1.18 (m, 18H), 0.88 (m, 9H). MH+388.

Example 24

N-Cyclohexyl-N-(t-butoxycarbonyl)-N'-{2-[(formylhydroxyamino)methyl]-heptanoyl}-hydrazine $^1$H NMR (400 MHz, CDCl$_3$) δ 8.79 (s, 1H), 8.30 (s, 1H), 4.11 (m, 1H), 3.85 (m, 1H), 3.35 (m, 1H), 2.55 (m, 1H), 1.94

(m, 1H), 1.81–1.57 (m, 5H), 1.51–1.18 (m, 18H), 0.89 (m, 3H). MH+400.

Example 25

N-(1-Ethyl-propyl)-N-(t-butoxycarbonyl)-N'-{2-[(formylhydroxyamino)methyl]-heptanoyl}-hydrazine $^1$H NMR (400 MHz, CDCl$_3$) δ 9.81 (s, 1H), 8.41 (s, 1H), 4.11–3.32 (m, 3H), 2.55 (m, 1H), 1.80 (m, 1H), 1.58–1.15 (m, 20H), 1.05 (m, 3H), 0.89 (m, 6H). MH+388.

Example 26

N-Isopropyl-N-(t-butoxycarbonyl)-N'-{2-[(formylhydroxyamino)methyl]-heptanoyl}-hydrazine $^1$H NMR (400 MHz, CDCl$_3$) δ 8.92 (s, 1H), 8.31 (s, 1H), 4.34–4.08 (m, 2H), 3.37 (m, 1H), 2.76 (m, 1H), 1.73 (m, 1H), 1.51 (s, 9H), 1.31 (m, 7H), 1.11 (m, 6H), 0.88 (m, 3H). MH+360.

Example 27

N-Propyl-N-(t-butoxycarbonyl)-N'-{2-[(formylhydroxyamino)methyl]-heptanoyl}-hydrazine $^1$H NMR (400 MHz, CDCl$_3$) δ 9.37 (s, 1H), 8.24 (s, 1H), 4.03–3.17 (m, 4H), 2.42 (m, 1H), 1.61 (m, 1H), 1.52–1.31 (m, 11H), 1.20 (m, 7H), 0.82 (m, 6H). MH+360.

Example 28

N-Ethyl-N-(t-butoxycarbonyl)-N'-{2-[(formylhydroxyamino)methyl]-heptanoyl}-hydrazine $^1$H NMR (400 MHz, CDCl$_3$) δ 9.79 (s, 1H), 8.05 (s, 1H), 4.21–3.25 (m, 4H), 2.48 (m, 1H), 1.51–1.02 (m, 20H), 0.88 (m, 3H). MH+346.

Example 29

N-Methoxycarbonyl-N'-{2-[(formylhydroxyamino)methyl]-heptanoyl}-hydrazine $^1$H NMR (400 MHz, CDCl$_3$) δ 8.35 (s, 1H), 8.05 (s, 1H), 7.64 (s, 1H), 7.50 (s, 1H), 3.68 (m, 3H), 3.37 (d, J=5.5 Hz, 2H), 2.72 (m, 1H), 1.61 (m, 1H), 1.41–1.12 (m, 7H), 0.85 (m, 3H). MH+276.

Example 30

N-{[1-(3,5-Dimethoxyphenyl)-1-methyl-ethoxy]carbonyl}-N'-{2-[(formylhydroxyamino)methyl]-heptanoyl}-hydrazine $^1$H NMR (400 MHz, CDCl$_3$) δ 8.71 (s, 1H), 8.21 (s, 1H), 7.76 (s, 1H), 6.62 (s, 1H), 6.36 (d, J=4.7 Hz, 1H), 3.83–3.69 (m, 7H), 3.38 (m, 1H), 2.70(m, 1H), 1.82–1.55 (m, 7H), 1.43–1.21 (m, 7H), 0.84 (m, 3H). MH+440.

Third Embodiment

As the third embodiment of the present invention, the compounds of Formula (1) with X=NR3 are disclosed, as in the racemic compound (42) and the chiral compounds (44) and (46). These compounds have preferentially R1=H.

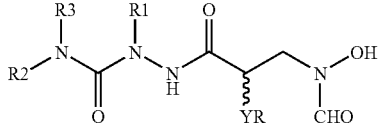

(42)

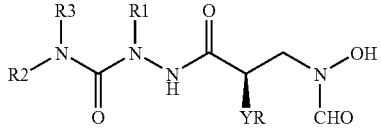

(44)

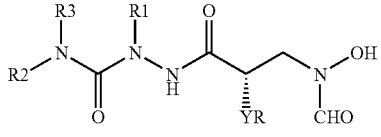

(46)

Preferred compounds useful in the present invention are selected from the group consisting of:
N-Butyl-N-[(4-methylpiperazin-1-yl)carbonyl]-N'-{(2R)-[(formylhydroxyamino)methyl]-heptanoyl}-hydrazine.
N-Butyl-N-diphenylaminocarbonyl-N'-{(2R)-[(formylhydroxyamino)methyl]-heptanoyl}-hydrazine.
N-Butyl-N-(t-butylamino)carbonyl-N'-{2-[(formylhydroxyamino)methyl]-heptanoyl}-hydrazine.
N-Butyl-N-phenylaminocarbonyl-N'-{2-[(formylhydroxyamino)methyl]-heptanoyl}-hydrazine.
N-Butyl-N-[(3,5-dimethyl-4,5-dihydro-isoxazol-4-yl)aminocarbonyl]-N'-{2-[(formylhydroxyamino)methyl]-heptanoyl}-hydrazine.
N-Butyl-N-[(1-morpholin-4-yl)carbonyl]-N'-{2-[(formylhydroxyamino)methyl]-heptanoyl}-hydrazine.
N-Phenylaminocarbonyl-N'-{2-[(formylhydroxyamino)methyl]-4-phenyl-butanoyl}-hydrazine.
N-Phenylaminocarbonyl-N'-{2-[(formylhydroxyamino)methyl]-hexanoyl}-hydrazine.
N-Phenylaminocarbonyl-N'-{2-[(formylhydroxyamino)methyl]-3-phenyl-propanoyl}-hydrazine.
N-Phenylaminocarbonyl-N'-{2-[(formylhydroxyamino)methyl]-3-(3,4-dichlorophenyl)-propanoyl}-hydrazine.
N-Phenylaminocarbonyl-N'-{2-[(formylhydroxyamino)methyl]-heptanoyl}-hydrazine.
N-(3,4-Dichlorophenylaminocarbonyl)-N'-{2-[(formylhydroxyamino)methyl]-heptanoyl}-hydrazine.
N-Phenylaminocarbonyl-N'-{(2R)-[(formylhydroxyamino)methyl]-heptanoyl}-hydrazine.
N-(3,4-Dichlorophenylaminocarbonyl)-N'-{(2R)-[(formylhydroxyamino)methyl]-heptanoyl)}-hydrazine.
N-[(1-Morpholin-4-yl)carbonyl]-N'-{(2R)-[(formylhydroxyamino)methyl]-heptanoyl}-hydrazine.
N-[(2-Methoxyphenyl)aminocarbonyl]-N'-{(2R)-[(formylhydroxyamino)methyl]-heptanoyl}-hydrazine.
N-[(2,4-Dichlorophenyl)aminocarbonyl]-N'-{(2R)-[(formylhydroxyamino)methyl]-heptanoyl}-hydrazine.
N-[(2,6-Dichlorophenyl)aminocarbonyl]-N'-{(2R)-[(formylhydroxyamino)methyl]-heptanoyl}-hydrazine.
N-[(4-Methyl-piperazin-1-yl)carbonyl]-N'-{(2R)-[(formylhydroxyamino)methyl]-heptanoyl}-hydrazine.
N-[(4-Chloro-3-trifluoromethylphenyl)aminocarbonyl]-N'-{(2R)-[(formylhydroxyamino)methyl]-heptanoyl}-hydrazine.
N-[(Methyl-phenyl-amino)carbonyl]-N'-{(2R)-[(formylhydroxyamino)methyl]-heptanoyl}-hydrazine.

The following synthetic schemes are merely illustrative of the methods by which the compounds of the invention may be prepared and are not intended to limit the scope of the invention as defined in the appended claims.

As shown in Scheme 6, treatment of an alkyl halide R1X (26) with hydrazine in a solvent such as ethanol, at an elevated temperature, gives the hydrazine derivative (27). Reacting compound (27) with the carbamyl chloride R2R3NC(O)Cl affords intermediate (39). Alternatively, compound (39) can be prepared from the Boc-protected hydrazine (29) by reaction with the aldehyde or ketone R'COR", followed by reduction with hydrogen gas in the presence of palladium, to afford hydrazine derivative (30). Reacting hydrazine (30) with the carbamyl chloride R2R3NC(O)Cl, followed by removing the Boc protecting group with an appropriate acid, such as trifluoroacetic acid, gives the hydrazine derivative (39) wherein R1=CHR'R".

Alternatively, reacting the isocyanate R2NCO (40) with hydrazine affords compound (39) wherein R1=H and R3=H. Alternatively, reacting the isocyanate R2NCO (40) with Boc-protected hydrazine, followed by acid treatment, affords the salt form of compound (39) wherein R1=H and R3=H. Alternatively, reacting the isocyanate R2NCO (40) with Cbz-protected hydrazine, followed by hydrogenation, affords compound (39) wherein R1=H and R3=H.

Scheme 6.

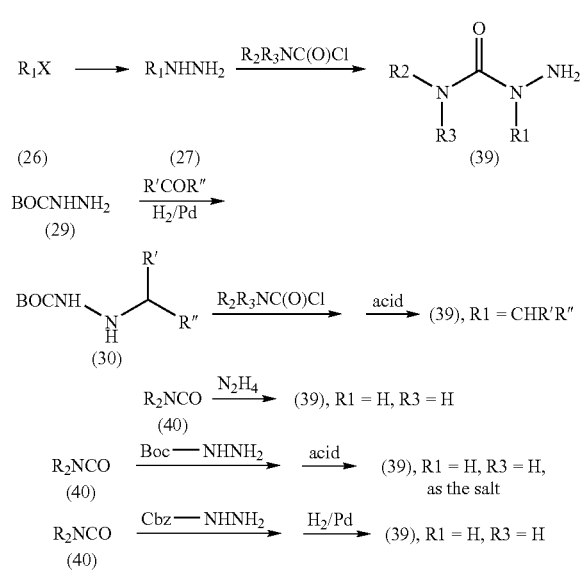

As shown in Scheme 7, coupling of the carboxylic acid (8) with the hydrazine derivative (39) provides hydrazide (41). Hydrogenolysis to remove the benzyl group using a catalyst, such as 10% Pd/C, in an appropriate solvent, such as ethanol, gives compound (42). Similarly, coupling of the chiral acid (17) or (25) with hydrazine derivative (39) provides the corresponding hydrazide (43) or (45). Hydrogenolysis of the benzyl group gives the final compounds (44) or (46).

Scheme 7.

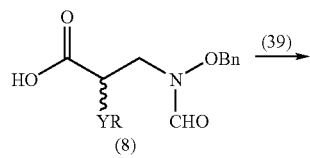

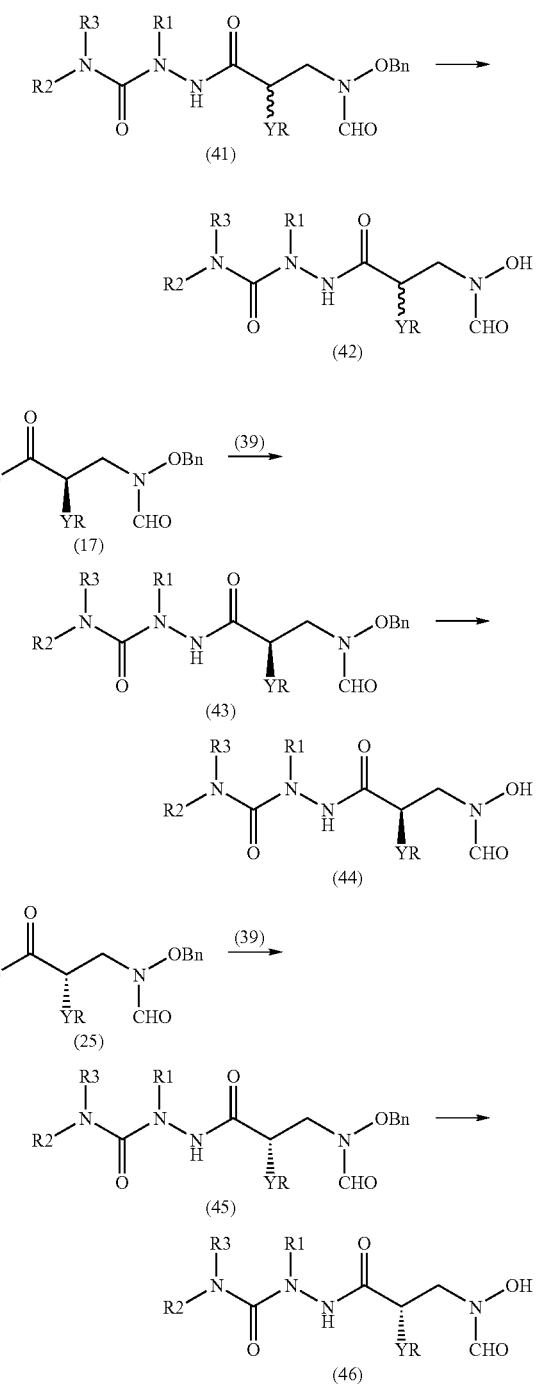

Alternatively, as shown in Scheme 8, the carbamate (34) wherein R2=t-butyl or benzyl can be converted to the hydrazide (47) by acid treatment or hydrogenolysis, respectively. Reaction of (47) with an isocyanate in an appropriate solvent, such as methylene chloride, and in the optional presence of an appropriate base, such as triethylamine, gives compound (42) wherein R3=H. Similarly, appropriate deprotection of the chiral carbamates (36) and (38), followed by reaction with an isocyanate, gives the chiral hydrazide (44) and (46), wherein R3=H.

Scheme 8.

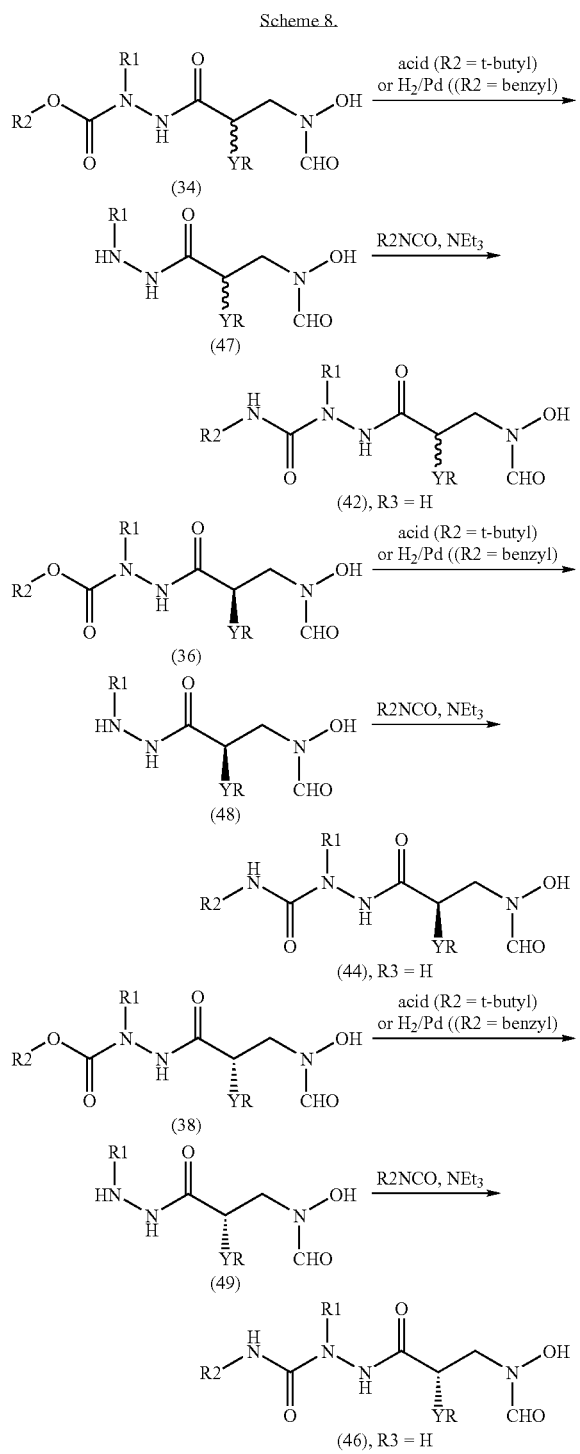

SYNTHETIC EXAMPLES

The invention will now be described by reference to the following examples which are merely illustrative and are not to be construed as a limitation of the scope of the present invention. The same experimental general conditions and conventions described in the Experimental Section of the Second Embodiment are applicable here.

The compounds disclosed in Examples 31 to 51 were prepared following the general procedures described in Example 1.

Preparation 13

N-[(4-Methylpiperazine)carbonyl]-N-butylhydrazine

To a solution of butyl-hydrazine (200 mg, 2.27 mmol) and triethylamine (0.95 mL, 6.81 mmol) in dichloromethane (10 mL) at −78° C. was added 4-methyl-1-piperazine carbonyl chloride hydrochloride (0.45 g, 2.27 mmol). The reaction mixture was stirred and allowed to warm up to room temperature overnight. Saturated aqueous NaHCO$_3$ (20 mL) was then added to the reaction mixture. The aqueous layer was extracted with dichloromethane (20 mL×2). The combined organic layers were dried (MgSO$_4$). Filtration and evaporation under vacuum, followed by purification by flash column chromatography (CH$_2$Cl$_2$:MeOH:Et$_3$N=9:1:0.05) provided the title compound (350 mg, 72%). $^1$H NMR (400 MHz, CHCl$_3$) δ 3.89 (br s, 2H), 3.41 (t, J=4.9Hz, 2H), 3.31 (t, J=4.9 Hz, 2H), 3.14 (t, J=7.6 Hz, 2H), 2.44–2.41 (m, 4H), 2.33 (s, 3H), 1.64 (m, 2H), 1.32 (m, 2H), 0.95 (t, J=7.3 Hz, 3H). MH+215.

Example 31

N-Butyl-N-[(4-methylpiperazin-1-yl)carbonyl]-N'-{(2R)-[(formylhydroxyamino)methyl]-heptanoyl}-hydrazine Purification by preparative HPLC yielded 44 mg (22%, 2 steps) of the title compound. MH+400.

Example 32

N-Butyl-N-diphenylaminocarbonyl-N'-{(2R)-[(formylhydroxyamino)methyl]-heptanoyl}-hydrazine Purification by preparative HPLC yielded 85 mg (16%, 2 steps) of the title compound. $^1$H NMR (400 MHz, CHCl$_3$) δ 9.52 (s, 1H), 8.89 (s, 1H), 8.35 (s, 1H), 7.39–7.07 (m, 10H), 4.03 (m, 1H), 3.51–3.26 (m, 3H), 2.54 (m, 1H), 1.74 (m, 1H), 1.41 (m, 1H), 1.30–1.07 (m, 10H), 0.90 (t, J=7.3 Hz, 3H), 0.76 (t, J=7.3 Hz, 3H). MH+469.

Example 33

N-Butyl-N-(t-butylamino)carbonyl-N'-{2-[(formylhydroxyamino)methyl]-heptanoyl}-hydrazine $^1$H NMR (400 MHz, CDCl$_3$) δ 8.25 (s, 1H), 7.81 (s, 1H), 4.10–3.20 (m, 6H), 3.01 (br s, 1H), 2.42 (m, 1H), 1.55–1.20 (m, 12H), 1.27 (s, 9H), 0.88–0.85 (m, 6H). MH+373.

Example 34

N-Butyl-N-phenylaminocarbonyl-N'-{2-[(formylhydroxyamino)methyl]-heptanoyl}-hydrazine $^1$H NMR (400 MHz, CDCl$_3$) δ 8.26 (s, 1H), 7.81 (s, 1H), 7.25 (br s, 1H), 4.10–3.20 (m, 6H), 3.00 (br s, 1H), 2.42 (m, 1H), 1.60–1.15 (m, 12H), 0.88–0.83 (m, 6H). MH+393.

Example 35

N-Butyl-N-[(3,5-dimethyl-4,5-dihydro-isoxazol-4-yl)aminocarbonyl]-N'-{2-[(formylhydroxyamino)methyl]-heptanoyl}-hydrazine $^1$H NMR (400 MHz, CDCl$_3$) δ 9.30 (s, 1H), 8.10 (s, 1H), 7.75 (s, 1H), 3.90–3.20 (m, 6H), 2.75 (m, 1H), 2.20–1.90 (m, 6H), 1.80–1.32 (m, 12H), 0.97–0.91 (m, 6H). MH+414.

Example 36

N-Butyl-N-[(1-morpholin-4-yl)carbonyl]-N'-{2 [(formylhydroxyamino)methyl]-heptanoyl}-hydrazine $^1$H NMR (400 MHz, CDCl$_3$) δ 8.80 (s, 1H), 7.80 (s, 1H), 3.80–3.20 (m, 12H), 2.75 (m, 1H), 1.80–1.30 (m, 14H), 0.96–0.90 (m, 6H). MH+387.

Example 37

N-Phenylaminocarbonyl-N'-{2-[(formylhydroxyamino)methyl]-4-phenyl-butanoyl}-hydrazine

MH+371.

Example 38

N-Phenylaminocarbonyl-N'-{2-[(formylhydroxyamino)methyl]-hexanoyl}-hydrazine $^1$H NMR (400 MHz, CDCl$_3$) δ 8.80 (br s, 1H), 7.84 (s, 1H), 7.29 (m, 5H), 3.90–3.40 (m, 2H), 2.86 (m, 1H), 1.70 (m, 1H), 1.50–1.15 (m, 5H), 0.89 (m, 3H). MH+323.

Example 39

N-Phenylaminocarbonyl-N'-{2-[(formylhydroxyamino)methyl]-3-phenyl-propanoyl}-hydrazine $^1$H NMR (400 MHz, CDCl$_3$) δ 9.90 (br s, 1H), 8.40 (s, 1H), 7.70 (s, 1H), 7.30–7.00 (m, 10H), 4.15–3.55 (m, 4H), 3.10 (m, 1H), 2.85 (m, 1H), 2.70 (m, 1H). MH+357.

Example 40

N-Phenylaminocarbonyl-N'-{2-[(formylhydroxyamino)methyl]-3-(3,4-dichlorophenyl)-propanoyl}-hydrazine $^1$H NMR (400 MHz, CDCl$_3$) δ 9.90 (br s, 1H), 8.50 (s, 1H), 7.70 (s, 1H), 7.28–7.05 (m, 8H), 4.10–3.45 (m, 2H), 3.10 (m, 1H), 2.95 (m, 1H), 2.70 (m, 1H). MH+425.

Example 41

N-Phenylaminocarbonyl-N'-{2-[(formylhydroxyamino)methyl]-heptanoyl}-hydrazine $^1$H NMR (400 MHz, CDCl$_3$) δ 8.90 (s, 1H), 8.40 (s, 1H), 7.95 (s, 1H), 7.81 (s, 1H), 7.41–6.95 (m, 5H), 3.90–3.40 (m, 2H), 2.83 (m, 1H), 1.61 (m, 1H), 1.42–1.12 (m, 7H), 0.87 (m, 3H). MH+337.

Example 42

N-(3,4-Dichlorophenylaminocarbonyl)-N'-{2-[(formylhydroxyamino)methyl]-heptanoyl}-hydrazine $^1$H NMR (400 MHz, CDCl$_3$) δ 8.29 (s, 1H), 7.75 (s, 1H), 7.52 (s, 1H), 7.22–7.15 (m, 4H), 3.98–3.29 (m, 2H), 2.85–2.43 (m, 1H), 1.59 (m, 1H), 1.41–1.15 (m, 7H), 0.80 (m, 3H). MH+406.

Example 43

N-Phenylaminocarbonyl-N'-{(2R)-[(formylhydroxyamino)methyl]-heptanoyl}-hydrazine $^1$H NMR (400 MHz, CDCl$_3$) δ 8.28 (s, 1H), 7.71 (s, 1H), 7.27–6.81 (m, 5H), 3.81–3.25 (m, 2H) 2.75–2.41 (m, 1H), 1.45 (m, 1H), 1.31–1.01 (m, 7H), 0.72 (m, 3H). MH+337.

Example 44

N-(3,4-Dichlorophenylaminocarbonyl)-N'-{(2R)-[(formylhydroxyamino)methyl]-heptanoyl}-hydrazine $^1$H NMR (400 MHz, CDCl$_3$) δ 10.00 (s, 1H), 8.41 (s, 1H), 8.28 (s, 1H), 8.16 (d, J=7 Hz, 1H), 7.74 (s, 1H), 7.38–6.81 (m, 3H), 3.81–3.38 (m, 2H), 2.81–2.52 (m, 1H), 1.68–1.07 (m, 8H), 0.78 (m, 3H). MH+405.

Example 45

N-[(1-Morpholin-4-yl)carbonyl]-N'-{(2R)-[(formylhydroxyamino)methyl]-heptanoyl}-hydrazine $^1$H NMR (400 MHz, CDCl$_3$) δ 9.29 (s, 1H), 8.25 (s, 1H), 8.15 (s, 1H), 4.08–3.49 (m, 6H), 3.35 (m, 4H), 2.78–2.55 (m, 1H), 1.52 (m, 1H), 1.41–1.08 (m, 7H), 0.79 (m, 3H). MH+331.

Example 46

N-[(2-Methoxyphenyl)aminocarbonyl]-N'-{(2R)-[(formylhydroxyamino)methyl]-heptanoyl}-hydrazine $^1$H NMR (400 MHz, CDCl$_3$) δ 8.33 (s, 1H), 7.99 (s, 1H), 7.05–6.70 (m, 4H) 4.14–3.32 (m, 5H), 2.85–2.59 (m, 1H), 1.60 (m, 1H), 1.42–1.18 (m, 7H), 0.87 (m, 3H). MH+367.

Example 47

N-[(2,4-Dichlorophenyl)aminocarbonyl]-N'-{(2R)-[(formylhydroxyamino)methyl]-heptanoyl}-hydrazine

MH+405.

Example 48

N-[(2,6-Dichlorophenyl)aminocarbonyl]-N'-{(2R)-[(formylhydroxyamino)methyl]-heptanoyl}-hydrazine

MH+405.

Example 49

N-[(4-Methyl-piperazin-1-yl)carbonyl]-N'-{(2R)-[(formylhydroxyamino)methyl]-heptanoyl}-hydrazine

MH+344.

Example 50

N-[(4-Chloro-3-trifluoromethylphenyl)aminocarbonyl]-N'-{(2R)-[(formylhydroxyamino)methyl]-heptanoyl}-hydrazine

MH+439.

Example 51

N-[(Methyl-phenyl-amino)carbonyl]-N'-{(2R)-[(formylhydroxyamino)methyl]-heptanoyl}-hydrazine

MH+351.

Fourth Embodiment

As the fourth embodiment of the present invention, the compounds of Formula (1) where X is a covalent bond are disclosed, as in the racemic compound (55) and the chiral compounds (57) and (59). These compounds have preferentially R1=H.

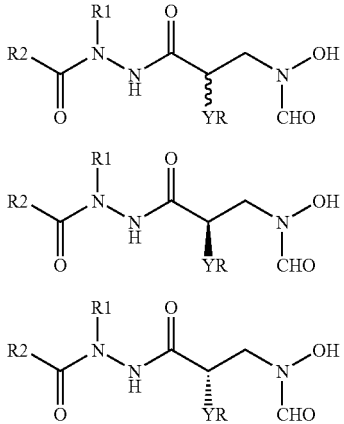

Preferred compounds useful in the present invention are selected from the group consisting of:

N-[(Phenylaminocarbonyl)-carbonyl]-N'-{(2R)-[(formylhydroxyamino)methyl]-heptanoyl}-hydrazine.
N-Butyl-N-{[1-(t-butoxycarbonyl)-piperidin-4-yl]-carbonyl}-N'-{2-[(formylhydroxyamino)methyl]-heptanoyl}-hydrazine.
N-Butyl-N-{[(1-t-butoxycarbonyl)-pyrrolidin-(2S)-yl]carbonyl}-N'-{2-[(formylhydroxyamino)methyl]-heptanoyl}-hydrazine.
N-Butyl-N-{[(1-t-butylaminocarbonyl)piperidin-4-yl]carbonyl}]-N'-{2-[(formylhydroxyamino)methyl]-heptanoyl}-hydrazine.
N-Butyl-N-{[(1-t-butylcarbonyl)piperidin-4-yl]carbonyl}]-N'-{2-[(formylhydroxyamino)methyl]-heptanoyl}-hydrazine.
N-Butyl-N-[(1,2,3,4-tetrahydro-quinoxalin-2-yl)carbonyl]-N'-{2-[(formylhydroxyamino)methyl]-heptanoyl}-hydrazine.
N-(p-Methoxyphenylacetyl)-N'-{(2R)-[(formylhydroxyamino)methyl]-heptanoyl}-hydrazine.
N-Phenoxyacetyl-N'-{(2R)-[(formylhydroxyamino)methyl]-heptanoyl}-hydrazine.
N-[(p-Methoxy-phenoxy)acetyl]-N'-{(2R)-[(formylhydroxyamino)methyl]-heptanoyl}-hydrazine.
N-(2,6-Dichlorophenyl-acetyl)-N'-{(2R)-[(formylhydroxyamino)methyl]-heptanoyl}-hydrazine.
N-(3,4-Dichlorophenylacetyl)-N'-{(2R)-[(formylhydroxyamino)methyl]-heptanoyl}-hydrazine.
N-(Ethoxycarbonyl)carbonyl)-N'-{(2R)-[(formylhydroxyamino)methyl]-heptanoyl}-hydrazine.
N-(2,4-Dichlorophenylacetyl)-N'-{(2R)-[(formylhydroxyamino)methyl]-heptanoyl}-hydrazine.
N-[(Benzofuran-2-yl)carbonyl]-N'-{(2R)-[(formylhydroxyamino)methyl]-heptanoyl}-hydrazine.
N-(2,3-Dichlorophenoxyacetyl)-N'-{(2R)-[(formylhydroxyamino)methyl]-heptanoyl}-hydrazine.
N-(3,4-Dimethoxyphenylacetyl)-N'-{(2R)-[(formylhydroxyamino)methyl]-heptanoyl}-hydrazine.
N-[(1H-Indol-2-yl)carbonyl]-N'-{(2R)-[(formylhydroxyamino)methyl]-heptanoyl}-hydrazine.
N-[(2-Methyl-pyridin-3-yl)carbonyl]-N'-{(2R)-[(formylhydroxyamino)methyl]-heptanoyl}-hydrazine.
N-[(5-Methoxy-benzofuran-2-yl)carbonyl]-N'-{(2R)-[(formylhydroxyamino)methyl]-heptanoyl}-hydrazine.
N-[(2,3-Dihydro-benzo[1,4]dioxin-(2S)-yl)carbonyl]-N'-{(2R)-[(formylhydroxyamino)methyl]-heptanoyl}-hydrazine.
N-[(Quinolin-2-yl)carbonyl]-N'-{(2R)-[(formylhydroxyamino)methyl]-heptanoyl}-hydrazine.
N-[(1,2,3,4-Tetrahydro-quinolin-6-yl)carbonyl]-N'-{(2R)-[(formylhydroxyamino)methyl]-heptanoyl}-hydrazine.
N-[(Tetrahydro-furan-(2S)-yl)carbonyl]-N'-{(2R)-[(formylhydroxyamino)methyl]-heptanoyl}-hydrazine.
N-[(Tetrahydro-furan-(2R)-yl)carbonyl]-N'-{(2R)-[(formylhydroxyamino)methyl]-heptanoyl}-hydrazine.
N-[(3-Methyl-benzofuran-2-yl)carbonyl]-N'-{(2R)-[(formylhydroxyamino)methyl]-heptanoyl}-hydrazine.
N-[(Pyridin-2-yl)acetyl]-N'-{(2R)-[(formylhydroxyamino)methyl]-heptanoyl}-hydrazine.
N-{3-[3-(4-Methoxybenzyl)-1H-benzoimidazol-2-yl]-propanoyl}-N'-{(2R)-[(formylhydroxyamino)methyl]-heptanoyl}-hydrazine.
N-[(Pyrimidin-2-yl)carbonyl]-N'-{(2R)-[(formylhydroxyamino)methyl]-heptanoyl}-hydrazine.
N-[(2-Methyl-5,6,7,8-tetrahydro-[1,8]naphthyridin-3-yl)carbonyl]-N'-{(2R)-[(formylhydroxyamino)methyl]-heptanoyl}-hydrazine.
N-[(Isoquinolin-3-yl)carbonyl]-N'-{(2R)-[(formylhydroxyamino)methyl]-heptanoyl}-hydrazine.
N-[(5,6,7,8-Tetrahydro-[1,8]naphthyridin-2-yl)carbonyl]-N'-{(2R)-[(formylhydroxyamino)methyl]-heptanoyl}-hydrazine.
N-(Phenylacetyl)-N'-{2-[(formylhydroxyamino)methyl]-heptanoyl}-hydrazine.
N-[(3,4-Dihydro-2H-benzo[b][1,4]dioxepin-7-yl)carbonyl]-N'-{(2R)-[(formylhydroxyamino)methyl]-heptanoyl}-hydrazine.
N-[(1-Methyl-2,5-dioxo-imidazolidin-4-yl)acetyl]-N'-{(2R)-[(formylhydroxyamino)methyl]-heptanoyl}-hydrazine.
N-(Phenylacetyl)-N'-{2-[(formylhydroxyamino)methyl]-3-phenyl-propanoyl}-hydrazine.
N-(Phenylacetyl)-N'-{2-[(formylhydroxyamino)methyl]-3-(3,4-dichloro)phenyl-propanoyl}-hydrazine.
N-[(4-Imidazol-1-yl)benzoyl]-N'-{(2R)-[(formylhydroxyamino)methyl]-heptanoyl}-hydrazine.
N-{[1-Methyl-5-oxo-2-S-(pyridin-3-yl)-pyrrolidin-(3S)-yl]carbonyl}-N'-{(2R)-[(formylhydroxyamino)methyl]-heptanoyl}-hydrazine.
N-[(1,2-Dihydro-cinnolin-4-yl)carbonyl]-N'-{(2R)-[(formylhydroxyamino)methyl]-heptanoyl}-hydrazine.
N-[4-(4-Acetylpiperazin-1-yl)phenoxyacetyl]-N'-{(2R)-[(formylhydroxyamino)methyl]-heptanoyl}-hydrazine.
N-Phenylacetyl-N'-{(2R)-[(formylhydroxyamino)methyl]-heptanoyl}-hydrazine.
N-{[1-Benzyl-5-oxo-pyrrolidin-(2S)-yl]-carbonyl}-N'-{(2R)-[(formylhydroxyamino)methyl]-heptanoyl}-hydrazine.
N-{[1-Benzyl-5-oxo-pyrrolidin-(2R)-yl]-carbonyl}-N'-{(2R)-[(formylhydroxyamino)methyl]-heptanoyl}-hydrazine.
N-[(5S)-Benzyl-3,6-dioxo-piperazin-(2S)-yl)acetyl]-N'-{(2R)-[(formylhydroxyamino)methyl]-heptanoyl}-hydrazine.
N-[(Quinolin-4-yl)carbonyl]-N'-{(2R)-[(formylhydroxyamino)methyl]-heptanoyl}-hydrazine.
N-[(Quinolin-8-yl)carbonyl]-N'-{(2R)-[(formylhydroxyamino)methyl]-heptanoyl}-hydrazine.
N-[(1,2,3,4-Tetrahydroquinolin-8-yl)carbonyl]-N'-{(2R)-[(formylhydroxyamino)methyl]-heptanoyl}-hydrazine.
N-(N"-Acetyl-L-tyrosyl)-N'-{(2R)-[(formylhydroxyamino)methyl]-heptanoyl}-hydrazine.

N-[(1-Acetyl-1,2,3,4-tetrahydro-quinolin-6-yl)carbonyl]-N'-{(2R)-[(formylhydroxyamino)methyl]-heptanoyl}-hydrazine.

N-[(1H-Benzoimidazol-2-yl)carbonyl]-N'-{(2R)-[(formylhydroxyamino)methyl]-heptanoyl}-hydrazine.

N-{[1-(2-Hydroxyacetyl)-1,2,3,4-tetrahydro-quinolin-6-yl]carbonyl}-N'-{(2R)-[(formylhydroxyamino)methyl]-heptanoyl}-hydrazine.

N-[(1H-Indol-5-yl)carbonyl]-N'-{(2R)-[(formylhydroxyamino)methyl]-heptanoyl}-hydrazine.

N-{4-[Methyl-(4,6-dimethylpyrimidin-2-yl)-amino]benzoyl}-N'-{(2R)-[(formylhydroxyamino)methyl]-heptanoyl}-hydrazine).

N-[(1-Benzo[1,3]dioxol-5-yl)carbonyl]-N'-{(2R)-[(formylhydroxyamino)methyl]-heptanoyl}-hydrazine.

N-{[4-(3,5-Dimethyl-pyrazol-1-yl)methyl]benzoyl}-N'-{(2R)-[(formylhydroxyamino)methyl]-heptanoyl}-hydrazine.

N-[4-(Morpholin-4-yl)-benzoyl]-N'-{(2R)-[(formylhydroxyamino)methyl]-heptanoyl}-hydrazine.

N-[4-Hydroxy-3-(morpholin-4-yl)methyl-benzoyl]-N'-{(2R)-[(formylhydroxyamino)methyl]-heptanoyl}-hydrazine.

N-(3-Hydroxy-3-methyl-butanoyl)-N'-{(2R)-[(formylhydroxyamino)methyl]-heptanoyl}-hydrazine.

N-(4-Methylamino-benzoyl)-N'-{(2R)-[(formylhydroxyamino)methyl]-heptanoyl}-hydrazine.

N-[(1-Isopropyl-1H-benzotriazol-5-yl)carbonyl]-N'-{(2R)-[(formylhydroxyamino)methyl]-heptanoyl}-hydrazine.

N-[(1,2,3,4-Tetrahydro-isoquinolin-(3S)-yl)carbonyl]-N'-{(2R)-[(formylhydroxyamino)methyl]-heptanoyl}-hydrazine.

N-[(5-Chloro-benzofuran-2-yl)carbonyl]-N'-{(2R)-[(formylhydroxyamino)methyl]-heptanoyl}-hydrazine.

N-{[-(Dimethylaminocarbonylmethyl)-3,4-dihydro-2H-quinolin-6-yl]carbonyl}-N'-{(2R)-[(formylhydroxyamino)methyl]-heptanoyl}-hydrazine.

N-[(2,2-Difluoro-benzo[1,3]dioxol-4-yl)carbonyl]-N'-{(2R)-[(formylhydroxyamino)methyl]-heptanoyl}-hydrazine.

N-[(5-Amino-benzofuran-2-yl)carbonyl]-N'-{(2R)-[(formylhydroxyamino)methyl]-heptanoyl}-hydrazine.

N-[(4-Oxo-1,2-dihydro-4H-pyrrolo[3,2,1-ij]quinolin-5-yl)carbonyl]-N'-{(2R)-[(formylhydroxyamino)methyl]-heptanoyl}-hydrazine.

N-[(7-Hydroxy-benzofuran-2-yl)carbonyl]-N'-{(2R)-[(formylhydroxyamino)methyl]-heptanoyl}-hydrazine.

N-[(6-Methoxy-benzofuran-2-yl)acetyl]-N'-{(2R)-[(formylhydroxyamino)methyl]-heptanoyl}-hydrazine.

N-[(5-Acetamidobenzofuran-2-yl)carbonyl]-N'-{(2R)-[(formylhydroxyamino)methyl]-heptanoyl}-hydrazine.

N-[(2,3-Dihydro-benzo[1,4]dioxin-6-yl)carbonyl]-N'-{(2R)-[(formylhydroxyamino)methyl]-heptanoyl}-hydrazine.

N-[(3-Amino-4,6-dimethyl-furo[2,3-b]pyridin-2-yl)carbonyl]-N'-{(2R)-[(formylhydroxyamino)methyl]-heptanoyl}-hydrazine.

N-[(2-Methyl-5,6,7,8-tetrahydro-[1,6]naphthyridin-3-yl)carbonyl]-N'-{(2R)-[(formylhydroxyamino)methyl]-heptanoyl}-hydrazine.

N-[(6-Fluoro-4H-benzo[1,3]dioxin-8-yl)carbonyl]-N'-{(2R)-[(formylhydroxyamino)methyl]-heptanoyl}-hydrazine.

N-[(7-Amino-1H-indol-2-yl)carbonyl)]-N'-{(2R)-[(formylhydroxyamino)methyl]-heptanoyl}-hydrazine.

N-[(1-Methyl-1,2,3,4-tetrahydro-quinolin-6-yl)carbonyl]-N'-{(2R)-[(formylhydroxyamino)methyl]-heptanoyl}-hydrazine.

N'-[(6,7,9,10,12,13,15,16-Octahydro-5,8,11,14,17-pentaoxa-benzocyclopentadecen-2-yl)carbonyl]-N'-{(2R)-[(formylhydroxyamino)methyl]-heptanoyl}-hydrazine.

N-[(2-Benzo[1,3]dioxol-5-yl)acetyl]-N'-{(2R)-[(formylhydroxyamino)methyl]-heptanoyl}-hydrazine.

N-Pentanoyl-N'-{2-[(formylhydroxyamino)methyl]-heptanoyl}-hydrazine.

N-Benzoyl-N'-{2-[(formylhydroxyamino)methyl]-heptanoyl}-hydrazine.

N-Trifluoroacetamido-N'-{2-[(formylhydroxyamino)methyl]-heptanoyl}-hydrazine.

N-[(3-Hydroxy-naphthalen-2-yl)carbonyl]-N'-{2-[(formylhydroxyamino)methyl]-heptanoyl}-hydrazine.

N-Phenylacetyl-N'-{2-[(formylhydroxyamino)methyl]-heptanoyl}-hydrazine.

N-[(Furan-2-yl)carbonyl]-N'-{(2R)-[(formylhydroxyamino)methyl]-heptanoyl}-hydrazine.

N-(4-Methoxybenzoyl)-N'-{(2R)-[(formylhydroxyamino)methyl]-heptanoyl}-hydrazine.

N-[(1H-Indol-3-yl)acetyl]-N'-{(2R)-[(formylhydroxyamino)methyl]-heptanoyl}-hydrazine.

N-(4-Dimethylaminobenzoyl)-N'-{(2R)-[(formylhydroxyamino)methyl]-heptanoyl}-hydrazine.

N-(2-Hydroxybenzoyl)-N'-{(2R)-[(formylhydroxyamino)methyl]-heptanoyl}-hydrazine.

N-[(Piperidin-4-yl)carbonyl]-N'-{(2R)-[(formylhydroxyamino)methyl]-heptanoyl}-hydrazine.

N-[(1,2,5,6-Tetrahydro-pyridin-3-yl)carbonyl]-N'-{(2R)-[(formylhydroxyamino)methyl]-heptanoyl}-hydrazine.

N-[(7-Methoxy-benzofuran-2-yl)carbonyl-N'-{(2R)-[(formylhydroxyamino)methyl]-heptanoyl}-hydrazine.

N-[(3-Chloro-4-methoxy-phenyl)acetyl]-N'-{(2R)-[(formylhydroxyamino)methyl]-heptanoyl}-hydrazine.

N-[(1H-Pyrrol-2-yl)carbonyl]-N'-{(2R)-[(formylhydroxyamino)methyl]-heptanoyl}-hydrazine.

N-[(Quinolin-7-yl)carbonyl]-N'-{(2R)-[(formylhydroxyamino)methyl]-heptanoyl}-hydrazine.

N-[(Pyridin-2-yl)carbonyl]-N'-{(2R)-[(formylhydroxyamino)methyl]-heptanoyl}-hydrazine.

N-(4-Chloro-3-methoxy-benzoyl)-N'-{(2R)-[(formylhydroxyamino)methyl]-heptanoyl}-hydrazine.

N-(3-Methoxybenzoyl)-N'-{(2R)-[(formylhydroxyamino)methyl]-heptanoyl}-hydrazine.

N-[(Quinolin-3-yl)carbonyl]-N'-{(2R)-[(formylhydroxyamino)methyl]-heptanoyl}-hydrazine.

N-[(5-Methyl-2-phenyl-oxazol-4-yl)carbonyl]-N'-{(2R)-[(formylhydroxyamino)methyl]-heptanoyl}-hydrazine.

N-[(Quinoxalin-2-yl)carbonyl]-N'-{(2R)-[(formylhydroxyamino)methyl]-heptanoyl}-hydrazine.

N-(Phenylacetyl)-N'-{2-[(formylhydroxyamino)methyl]-4-phenylbutanoyl}-hydrazine.

N-[(3-Methoxy-quinoxalin-2-yl)carbonyl]-N'-{(2R)-[(formylhydroxyamino)methyl]-heptanoyl}-hydrazine.

N-[(2,6-Dimethoxypyridin-3-yl)carbonyl]-N'-{(2R)-[(formylhydroxyamino)methyl]-heptanoyl}-hydrazine.

N-[(N"-Methylsulfonyl)-L-tyrosyl]-N'-{(2R)-[(formylhydroxyamino)methyl]-heptanoyl}-hydrazine.

N-{[5-Oxo-pyrrolidin-(2S)-yl]carbonyl}-N'-{(2R)-[(formylhydroxyamino)methyl]-heptanoyl}-hydrazine.

N-[(4-(Pyrrol-1-yl)benzoyl]-N'-{(2R)-[(formylhydroxyamino)methyl]-heptanoyl}-hydrazine.

N-(4-Acetamidobenzoyl)-N'-{(2R)-[(formylhydroxyamino)methyl]-heptanoyl}-hydrazine.

N-[(3-Cyclopentyloxy-4-methoxy)benzoyl]-N'-{(2R)-[(formylhydroxyamino)methyl]-heptanoyl}-hydrazine.

N-(Phenylacetyl)-N'-{2-[(formylhydroxyamino)methyl]-3-cyclopentyl-propanoyl}-hydrazine.

N-[(7-Methoxy-benzofuran-2-yl)carbonyl]-N'-{2-[(formylhydroxyamino)methyl]-3-cyclopentyl-propanoyl}-hydrazine.
N-[3-(Morpholin-4-yl)propanoyl]-N'-{(2R)-[(formylhydroxyamino)methyl]-heptanoyl}-hydrazine.
N-[(2,3-Dihydro-benzofuran-5-yl)carbonyl]-N'-{(2R)-[(formylhydroxyamino)methyl]-heptanoyl}-hydrazine.
N-[(4,6-Dimethoxy-pyrimidin-2-yl)benzoyl]-N'-{(2R)-[(formylhydroxyamino)methyl]-heptanoyl}-hydrazine.
N-[(2-Trifluoromethyl-5,6,7,8-tetrahydro-naphthyridin-2-yl)carbonyl]-N'-{(2R)-[(formylhydroxyamino)methyl]-heptanoyl}-hydrazine.
N-[(9H-beta-Carbolin-3-yl)carbonyl]-N'-{(2R)-[(formylhydroxyamino)methyl]-heptanoyl}-hydrazine.

The following synthetic, schemes are merely illustrative of the methods by which the compounds of the invention may be prepared and are not intended to limit the scope of the invention as defined in the appended claims.

As shown in Scheme 9, treatment of an alkyl halide R1X (26) with hydrazine in a solvent such as ethanol, at an elevated temperature, gives the hydrazine derivative (27). Reacting compound (27) with the acid chloride R2C(O)Cl affords intermediate (50). Alternatively, compound (50) can be prepared from the Boc-protected hydrazine (29) by reaction with the aldehyde or ketone R'COR", followed by reduction with hydrogen gas in the presence of palladium, to afford hydrazine derivative (30). Reacting hydrazine (30) with the acid chloride R2C(O)Cl, followed by removal of the Boc protecting group with an appropriate acid, such as trifluoroacetic acid, gives the hydrazine (50) wherein R1=CHR'R". Alternatively, ester (51) can be submitted to hydrazinolysis to afford (50) wherein R1=H. Alternatively, acid (52) can be reacted with ethyl chloroformate to form the intermediate mixed anhydride (53), which upon hydrazinolysis yields (50) wherein R1∇H.

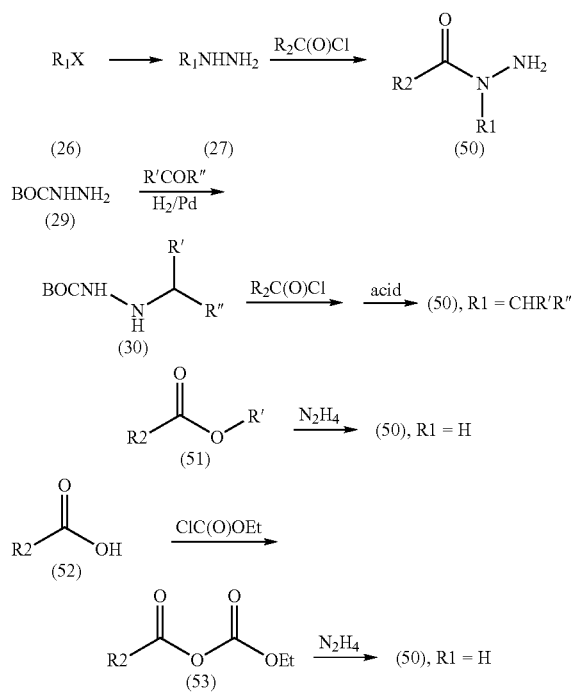

Scheme 9.

As shown in Scheme .10, coupling of the carboxylic acid (8) with the hydrazine derivative (50) provides acylated hydrazide (54). Hydrogenolysis to remove the benzyl group using a catalyst, such as 10% Pd/C, in an appropriate solvent, such as ethanol, gives compound (55). Similarly, coupling of the chiral acid (17) or (25) with hydrazine derivative (50) provides the corresponding hydrazide (56) or (58). Hydrogenolysis of the benzyl group gives the final compounds (57) or (59).

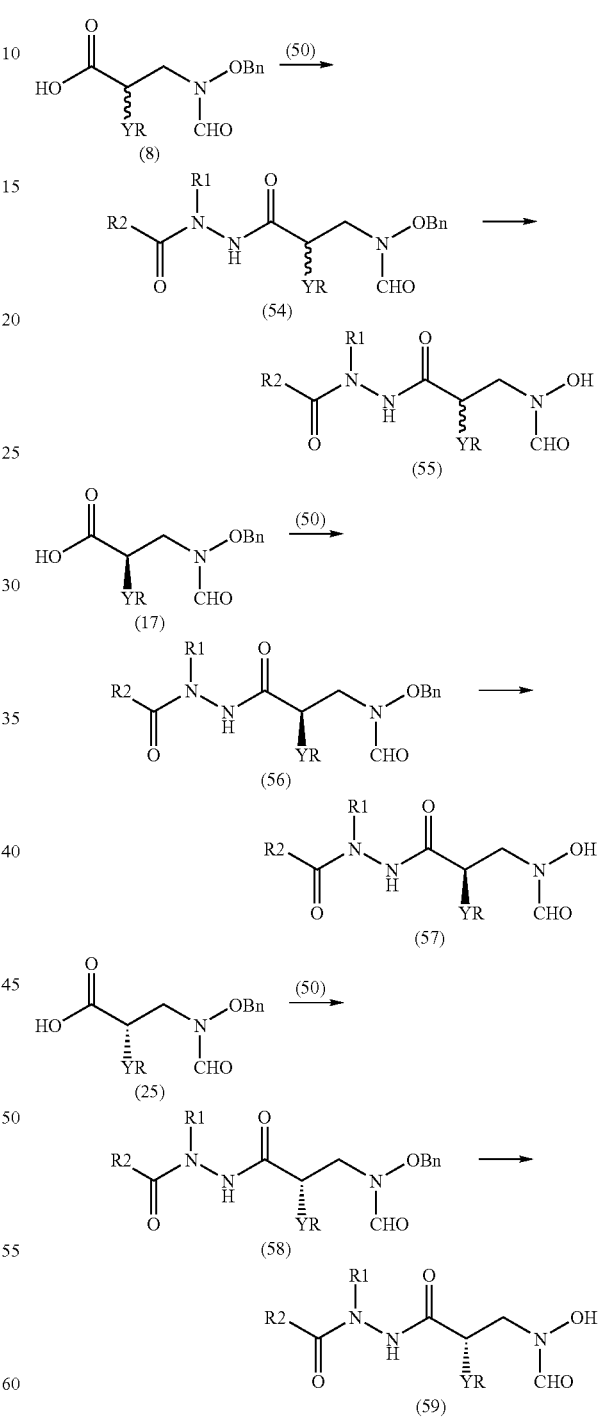

Alternatively, as shown in Scheme 11, the carbamate (34) wherein R2=t-butyl or benzyl can be converted to the hydrazide (47) by acid treatment or hydrogenolysis, respectively. Reaction of (47) with the acyl chloride R2C(O)Cl or the mixed anhydride R2C(O)OC(O)OEt in an appropriate solvent, such as methylene chloride, and in the presence of an optional appropriate base, such as triethylamine, gives compound (55). Similarly, appropriate deprotection of the chiral carbamates (36) and (38), followed by reaction with an acyl chloride or a mixed anhydride, gives the chiral acylated hydrazide (57) or (59).

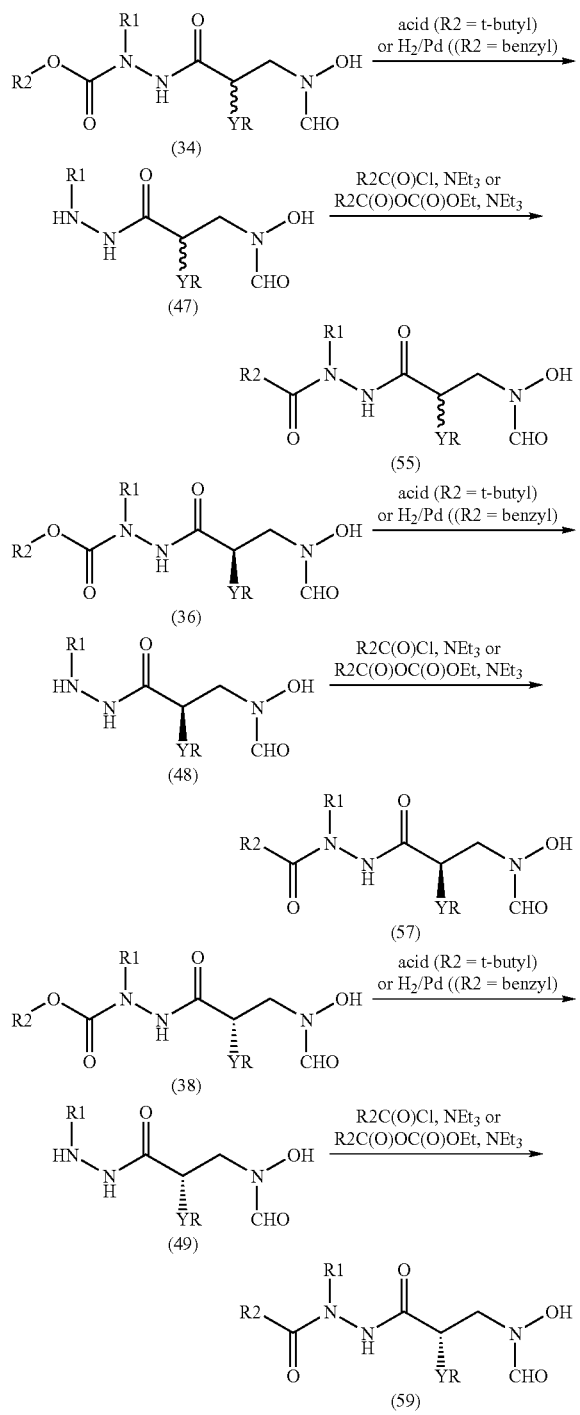

SYNTHETIC EXAMPLES

The invention will now be described by reference to the following examples which are merely illustrative and are not to be construed as a limitation of the scope of the present invention. The same experimental general conditions and conventions described in the Experimental Section of the Second Embodiment are applicable here.

The compounds disclosed in Examples 52 to 165 were prepared following the general procedures described in Example 1.

Example 52

N-[(Phenylaminocarbonyl)-carbonyl]-N'-{(2R)-[(formylhydroxyamino)methyl]-heptanoyl}-hydrazine

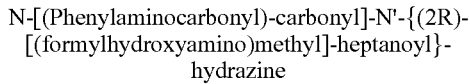

$^1$H NMR (400 MHz, CDCl$_3$) δ 9.50 (s, 1H), 9.20 (s, 1H), 7.85 (s, 1H), 7.70–7.00 (m, 5H), 3.75 (m, 1H), 3.40 (m, 1H), 2.88 (m, 1H), 1.63 (m, 1H), 1.39–1.15 (m, 7H), 0.79 (t, J=6.8 Hz, 3H). MH+365.

Example 53

N-Butyl-N-{[1-(t-butoxycarbonyl)-piperidin-4-yl]-carbonyl}-N'-{2-[(formylhydroxyamino)methyl]-heptanoyl}-hydrazine

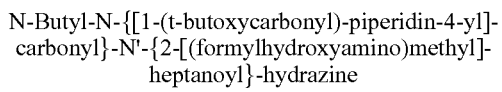

$^1$H NMR (400 MHz, CDCl$_3$): δ 9.14 (br s, 1H), 8.33 (br s, 1H), 7.81 (br s, 1H), 4.30–3.20 (m, 8H), 2.80–2.50 (m, 2H), 1.92–1.22 (m, 14H), 1.47 (s, 9H), 0.97–0.90 (m, 6H). MH+485.

Example 54

N-Butyl-N-([(1-t-butoxycarbonyl)-pyrrolidin-(2S)-yl]carbonyl)-N'-{2-[(formylhydroxyamino)methyl]-heptanoyl}-hydrazine

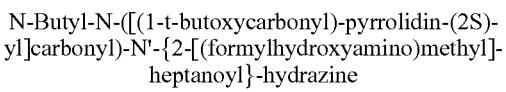

$^1$H NMR (400 MHz, CDCl$_3$) δ 9.70 (br s, 1H), 8.21 (s, 1H), 7.80 (s, 1H), 4.51–3.20 (m, 6H), 2.86 (m, 1H), 2.18–1.41 (m, 6H), 1.38 (s, 9H), 1.38–1.17 (m, 10H), 0.88 (m, 6H). MH+471.

Example 55

N-Butyl-N-{[(1-t-butylaminocarbonyl)piperidin-4-yl]carbonyl}-N'-{2-[(formylhydroxyamino)methyl]-heptanoyl}-hydrazine

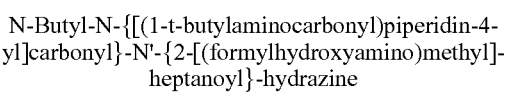

$^1$H NMR (400 MHz, CDCl$_3$): δ 9.67 (br s, 1H), 8.38 (s, 1H), 4.15–3.47 (m, 8H), 2.89 (m, 1H), 2.67 (m, 1H), 1.75–1.26 (m, 16H), 1.37 (s, 9H), 0.99–0.90 (m, 6H). MH+484.

Example 56

N-Butyl-N-{[(1-t-butylcarbonyl)piperidin-4-yl]carbonyl}]-N'-{2-[(formylhydroxyamino)methyl]-heptanoyl}-hydrazine

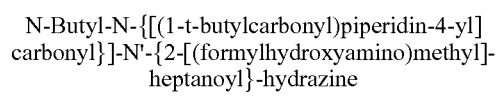

$^1$H NMR (400 MHz, CDCl$_3$): δ 9.30 (s, 1H), 8.25 (s, 1H), 7.80 (s, 1H), 4.39–3.34 (m, 8H), 2.95 (m, 1H), 2.79 (m, 1H), 1.89–1.25 (m, 16H), 1.29 (s, 9H), 0.99–0.90 (m, 6H). MH+469.

Example 57

N-Butyl-N-[(1,2,3,4-tetrahydro-quinoxalin-2-yl)carbonyl]-N'-{2-[(formylhydroxyamino)methyl]-heptanoyl}-hydrazine

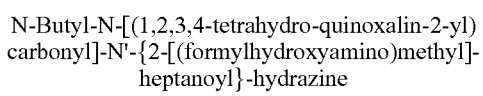

$^1$H NMR (400 MHz, CDCl$_3$): δ 9.28 (s, 1H), 8.20 (s, 1H), 7.80 (s, 1H), 6.70–6.51 (m, 4H), 4.16–3.22 (m, 6H), 2.87 (m, 1H), 2.75 (m, 1H), 1.64–1.26 (m, 12H), 0.97–0.87 (m, 6H). MH+434.

Example 58

N-(p-Methoxyphenylacetyl)-N'-{(2R)-[(formylhydroxyamino)methyl]-heptanoyl}-hydrazine $^1$H NMR (400 MHz, CDCl$_3$): δ 9.20 (s, 1H), 8.30 (s, 1H), 7.50 (s, 1H), 7.24 (d, J=16.3 Hz, 2H), 6.90 (d, J=16.3 Hz, 2H), 3.95–3.38 (m, 4H), 3.77 (s, 3H), 2.83 (m, 1H), 1.64 (m, 1H), 1.34 (m, 1H), 1.29 (m, 6H), 0.86 (t, J=6.3 Hz, 3H). MH+366.

Example 59

N-Phenoxyacetyl-N'-{(2R)-[(formylhydroxyamino)methyl]-heptanoyl}-hydrazine

MH+352.

Example 60

N-[(p-Methoxy-phenoxy)acetyl]-N'-{(2R)-[(formylhydroxyamino)methyl]-heptanoyl}-hydrazine $^1$H NMR (400 MHz, CDCl$_3$): δ 9.39 (s, 1H), 8.53 (s, 1H), 7.48 (s, 1H), 6.79–6.73 (m, 4H), 4.49 (m, 2H), 3.73 (s, 3H), 3.44 (m, 2H), 2.82 (m, 1H), 1.64 (m, 1H), 1.25 (m, 1H), 1.24–1.19 (m, 6H), 0.80 (t, J=6.7 Hz, 3H). MH+382.

Example 61

N-(2,6-Dichlorophenyl-acetyl)-N'-{(2R)-[(formylhydroxyamino)methyl]-heptanoyl}-hydrazine $^1$H NMR (400 MHz, CDCl$_3$): δ 8.35 (s, 1H), 7.80 (s, 1H), 7.30–7.10 (m, 3H), 4.09 (s, 2H), 3.85–3.50 (m, 2H), 2.90 (m, 1H), 1.80–1.28 (m, 6H), 0.89 (br s, 3H). MH+405.

Example 62

N-(3,4-Dichlorophenylacetyl)-N'-{(2R)-[(formylhydroxyamino)methyl]-heptanoyl}-hydrazine $^1$H NMR (400 MHz, CDCl$_3$): δ 8.30 (s, 1H), 7.91 (s, 1H), 7.20–7.10 (m, 3H), 3.45–3.10 (m, 2H), 3.25 (br s, 2H), 1.85 (m, 1H), 1.62 (m, 1H), 1.45 (m, 1H), 1.32 (m, 6H), 0.91 (br s, 3H). MH+405.

Example 63

N-(Ethoxycarbonyl)carbonyl]-N'-{(2R)-[(formylhydroxyamino)methyl]-heptanoyl}-hydrazine $^1$H NMR (400 MHz, CDCl$_3$): δ 9.96 (s, 1H), 9.27 (s, 1H), 7.77 (s, 1H), 4.37 (m, 2H), 3.90 (m, 1H), 3.51 (m, 1H), 2.96 (m, 1H), 1.71 (m, 1H), 1.41 (m, 1H), 1.40–1.32 (m, 9H), 0.91 (br s, 3H). MH+318.

Example 64

N-(2,4-Dichlorophenylacetyl)-N'-{(2R)-[(formylhydroxyamino)methyl]-heptanoyl}-hydrazine $^1$H NMR (400 MHz, CDCl$_3$): δ 8.70 (s, 1H), 7.80 (s, 1H), 7.50–7.20 (m, 3H), 3.82 (m, 2H), 3.55 (m, 2H), 2.85 (m, 1H), 1.85 (m, 1H), 1.61 (m, 1H), 1.45–1.22 (m, 6H), 0.85 (br s, 3H). MH+405.

Example 65

N-[(Benzofuran-2-yl)carbonyl]-N'-{(2R)-[(formylhydroxyamino)methyl]-heptanoyl}-hydrazine $^1$H NMR (400 MHz, CDCl$_3$): δ 9.87 (s, 1H), 8.68 (s, 1H), 7.78 (s, 1H), 7.54–7.06 (m, 5H), 4.15–3.30 (m, 2H), 2.95 (m, 1H), 1.85 (m, 1H), 1.62 (m, 1H), 1.27–1.18 (m, 6H), 0.84 (br s, 3H). MH+362.

Example 66

N-(2,3-Dichlorophenoxyacetyl)-N'-{(2R)-[(formylhydroxyamino)methyl]-heptanoyl}-hydrazine $^1$H NMR (400 MHz, CDCl$_3$): δ 9.17 (s, 1H), 7.88 (br s, 1H), 7.28–7.14 (m, 3H), 4.73 (m, 2H), 3.76 (m, 1H), 3.49 (m, 1H), 2.90 (m, 1H), 1.74 (m, 1H), 1.41–1.28 (m, 7H), 0.90 (br s, 3H). MH+421.

Example 67

N-(3,4-Dimethoxyphenylacetyl)-N'-{(2R)-[(formylhydroxyamino)methyl]-heptanoyl}-hydrazine $^1$H NMR (400 MHz, CDCl$_3$): δ 8.92 (s, 1H), 7.58 (s, 1H), 6.83 (m, 3H), 3.87 (s, 3H), 3.85 (s, 3H), 3.74–3.44 (m, 4H), 1.65 (m, 1H), 1.36 (m, 1H), 1.29–1.23 (m, 6H), 0.88 (t, J=6.5 Hz, 3H). MH+396.

Example 68

N-[(1H-Indol-2-yl)carbonyl]-N'-{(2R)-[(formylhydroxyamino)methyl]-heptanoyl}-hydrazine $^1$H NMR (400 MHz, CDCl$_3$): δ 9.51 (s, 1H), 8.50 (s, 1H), 7.81 (s, 1H), 7.50–6.80 (m, 5H), 4.20–3.45 (m, 2H), 2.95 (m, 1H), 1.82 (m, 1H), 1.75–1.20 (m, 7H), 1.00 (br s, 3H). MH+396.

Example 69

N-[(2-Methyl-pyridin-3-yl)carbonyl]-N'-{(2R)-[(formylhydroxyamino)methyl]-heptanoyl}-hydrazine $^1$H NMR (400 MHz, CDCl$_3$): δ 8.50 (s, 1H), 7.80 (s, 1H), 7.70–7.00 (m, 3H), 3.84 (m, 1H), 3.50 (m, 1H), 2.58 (s, 1H), 1.73 (m, 1H), 1.44 (m, 1H), 1.43–1.27 (m, 6H), 0.89 (br s, 3H). MH+337.

Example 70

N-[(5-Methoxy-benzofuran-2-yl)carbonyl]-N'-{(2R)-[(formylhydroxyamino)methyl]-heptanoyl}-hydrazine $^1$H NMR (400 MHz, CDCl$_3$): δ 9.50 (s, 1H), 8.50 (s, 1H), 7.85 (s, 1H), 7.50–6.80 (m, 4H), 3.90 (m, 1H), 3.80 (s, 3H), 3.55 (m, 1H), 3.00 (m, 1H), 1.85 (m, 1H), 1.60–1.25 (m, 7H), 0.95 (br s, 3H). MH+392.

Example 71

N-[(2,3-Dihydro-benzo[1,4]dioxin-(2S)-yl)carbonyl]-N'-{(2R)-[(formylhydroxyamino)methyl]-heptanoyl}-hydrazine $^1$H NMR (400 MHz, CD$_3$OD) δ 8.50 (s, 1H), 7.80 (s, 1H), 7.30 (m, 4H), 4.55–3.20 (m, 5H), 2.85 (m, 1H), 1.85 (m, 1H), 1.65–1.24 (m, 7H), 0.93 (t, J=6.2 Hz, 3H). MH+380.

Example 72

N-[(Quinolin-2-yl)carbonyl]-N'-{(2R)-[(formylhydroxyamino)methyl]-heptanoyl}-hydrazine ¹H NMR (400 MHz, CD₃OD): δ 8.51–7.72 (m, 6H), 3.88 (m, 1H), 3.61 (m, 1H), 2.99 (m, 1H), 1.69 (m, 1H), 1.58–1.26 (m, 7H), 0.97 (t, J=6.7 Hz, 3H). MH+373.

Example 73

N-[(1,2,3,4-Tetrahydro-quinolin-6-yl)carbonyl]-N'-{(2R)-[(formylhydroxyamino)methyl]-heptanoyl}-hydrazine ¹H NMR (400 MHz, CD₃OD): δ 8.36 (s, 1H), 7.48 (br s, 2H), 6.45 (d, J=9.04 Hz, 1H), 3.96–3.32 (m, 4H), 2.91 (m, 1H), 2.77 (t, J=6.12 Hz, 2H), 1.98 (m, 2H), 1.65 (m, 1H), 1.49 (m, 1H), 1.36 (m, 6H), 0.94 (br s, 3H). MH+377.

Example 74

N-[(Tetrahydro-furan-(2S)-yl)carbonyl]-N'-{(2R)-[(formylhydroxyamino)methyl]-heptanoyl}-hydrazine ¹H NMR (400 MHz, CD₃OD): δ 8.32 (s, 1H), 4.44 (m, 1H), 4.03 (m, 1H), 3.88 (m, 3H), 3.50 (m, 1H), 2.85 (m, 1H), 2.35–1.93 (m, 4H), 1.49 (m, 1H), 1.40 (m, 1H), 1.35 (m, 6H), 0.92 (t, J=6.9 Hz, 3H). MH+316.

Example 75

N-[(Tetrahydro-furan-(2R)-yl)carbonyl]-N'-{(2R)-[(formylhydroxyamino)methyl]-heptanoyl}-hydrazine ¹H NMR (400 MHz, CD₃OD): δ 8.32 (s, 1H), 4.43 (m, 1H), 4.03 (m, 1H), 3.87 (m, 3H), 3.55 (m, 1H), 2.86 (m, 1H), 2.28–1.93 (m, 4H), 1.63 (m, 1H), 1.50 (m, 1H), 1.34 (m, 6H), 0.93 (br s, 3H). MH+316.

Example 76

N-[(3-Methyl-benzofuran-2-yl)carbonyl]-N'-{(2R)-[(formylhydroxyamino)methyl]-heptanoyl}-hydrazine ¹H NMR (400 MHz, CDCl₃): δ 8.36 (s, 1H), 7.54–7.20 (m, 4H), 4.04 (m, 1H), 3.48 (m, 1H), 2.97 (s, 3H), 2.59 (m, 1H), 1.66 (m, 1H), 1.28 (m, 1H), 1.27 (m, 6H), 0.83 (t, J=6.7 Hz, 3H). MH+376.

Example 77

N-[(Pyridin-2-yl)acetyl]-N'-{(2R)-[(formylhydroxyamino)methyl]-heptanoyl}-hydrazine ¹H NMR (400 MHz, CD₃OD): δ 8.48 (s, 1H), 7.90–7.33 (m, 4H), 4.00–3.50 (m, 4H), 2.87 (m, 1H), 1.62 (m, 1H), 1.46 (m, 1H), 1.33 (m, 6H), 0.90 (br s, 3H). MH+337.

Example 78

N-{3-[3-(4-Methoxybenzyl)-1H-benzoimidazol-2-yl]-propanoyl}-N'-{(2R)-[(formylhydroxyamino)methyl]-heptanoyl}-hydrazine ¹H NMR (400 MHz, CD₃OD): δ 8.31 (s, 1H), 7.61 (m, 1H), 7.42 (m, 1H), 7.25 (m, 2H), 7.10 (d, J=8.6 Hz, 2H), 6.88 (d, J=8.6 Hz, 2H), 5.46 (s, 2H), 3.77 (s, 3H), 3.90–3.50 (m, 2H), 3.23 (m, 2H), 2.85 (m, 2H), 2.69 (m, 1H), 1.65 (m, 1H), 1.61 (m, 1H), 1.33 (m, 6H), 0.92 (m, 3H). MH+510.

Example 79

N-[(Pyrimidin-2-yl)carbonyl]-N'-{(2R)-[(formylhydroxyamino)methyl]-heptanoyl}-hydrazine ¹H NMR (400 MHz, CD₃OD): δ 9.26 (s, 1H), 8.84 (s, 1H), 8.72 (s, 1H), 7.95 (s, 1H), 3.85–3.40 (m, 2H), 2.86 (m, 1H), 1.67 (m, 1H), 1.47 (m, 1H), 1.37 (m, 6H), 0.94 (t, J=6.8 Hz, 3H). MH+324.

Example 80

N-[(2-Methyl-5,6,7,8-tetrahydro-[1,8]naphthyridin-3-yl)carbonyl]-N'-{(2R)-[(formylhydroxyamino)methyl]-heptanoyl}-hydrazine ¹H NMR (400 MHz, CD₃OD): δ 7.92 (s, 1H), 7.44 (s, 1H), 3.90–3.60 (m, 2H), 3.43 (m, 2H), 2.94 (m, 1H), 2.75 (m, 2H), 2.47 (s, 3H), 1.98 (m, 2H), 1.66 (m, 1H), 1.45 (m, 1H), 1.37 (m, 6H), 0.94 (br s, 3H). MH+392.

Example 81

N-[(Isoquinolin-3-yl)carbonyl]-N'-{(2R)-[(formylhydroxyamino)methyl]-heptanoyl}-hydrazine ¹H NMR (400 MHz, CD₃OD): δ 9.17 (s, 1H), 8.48 (s, 1H), 8.03–7.73 (m, 5H), 4.03–3.99 (m, 1H), 3.59 (m, 1H), 2.70 (m, 1H), 1.71 (m, 1H), 1.43 (m, 1H), 1.26 (m, 6H), 0.86 (t, J=6.7 Hz, 3H). MH+373.

Example 82

N-[(5,6,7,8-Tetrahydro-[1,8]naphthyridin-2-yl)carbonyl]-N'-{(2R)-[(formylhydroxyamino)methyl]-heptanoyl}-hydrazine ¹H NMR (400 MHz, CD₃OD): δ 7.93 (br s, 1H), 7.31 (d, J=7.2 Hz, 1H), 7.21 (d, J=7.31 Hz, 1H), 3.82 (m, 1H), 3.55 (m, 1H), 3.43 (br s, 2H), 2.94 (m, 1H), 2.80 (br s, 2H), 1.92 (m, 2H), 1.65 (m, 1H), 1.60–1.09 (m, 7H), 0.94 (br s, 3H). MH+378.

Example 83

N-(Phenylacetyl)-N'-{2-[(formylhydroxyamino)methyl]-heptanoyl}-hydrazine

¹H NMR (400 MHz, CDCl₃): δ 8.86 (s, 1H), 7.60 (s, 1H), 7.33 (m, 5H), 3.90–3.42 (m, 4H), 2.83 (m, 1H), 1.67 (m, 1H), 1.32–1.20 (m, 5H), 0.89 (t, J=6.7 Hz, 3H). MH+322.

Example 84

N-[(3,4-Dihydro-2H-benzo[b][1,4]dioxepin-7-yl)carbonyl]-N'-{(2R)-[(formylhydroxyamino)methyl]-heptanoyl}-hydrazine ¹H NMR (400 MHz, CDCl₃): δ 8.45 (d, J=9.2 Hz, 1H), 7.82 (s, 1H), 7.45–7.28 (m, 2H), 4.30–3.40 (m, 6H), 2.96 (m, 1H), 2.22 (m, 2H), 1.70 (m, 1H), 1.55 (m, 1H), 1.35–1.23 (m, 6H), 0.88 (t, J=6.7 Hz, 3H). MH+394.

Example 85

N-[(1-Methyl-2,5-dioxo-imidazolidin-4-yl)acetyl]-N'-{(2R)-[(formylhydroxyamino)methyl]-heptanoyl}-hydrazine ¹H NMR (400 MHz, CD₃OD): δ 7.90 (s, 1H), 4.39 (m, 1H), 3.84–3.50 (m, 2H), 2.97 (s, 3H), 2.85 (m, 1H), 2.67 (m, 1H), 1.62 (m, 1H), 1.49 (m, 1H), 1.34 (m, 6H), 0.93 (br s, 3H). MH+372.

Example 86

N-(Phenylacetyl)-N'-{2-[(formylhydroxyamino)methyl]-3-phenyl-propanoyl}-hydrazine $^1$H NMR (400 MHz, CDCl$_3$): δ 9.80 (br s, 1H), 8.10 (s, 1H), 7.22 (m, 10H), 3.96–3.43 (m, 4H), 3.15 (m, 1H), 3.02 (m, 1H), 2.70 (m, 1H). MH+356.

Example 87

N-(Phenylacetyl)-N'-{2-[(formylhydroxyamino)methyl]-3-(3,4-dichloro)phenyl-propanoyl}-hydrazine $^1$H NMR (400 MHz, CDCl$_3$): δ 8.36 (br s, 1H), 7.60 (s, 1H), 7.37–7.00 (m, 8H), 4.17–3.51 (m, 4H), 3.05 (m, 1H), 2.95 (m, 1H), 2.65 (m, 1H). MH+424.

Example 88

N-[(4-Imidazol-1-yl)benzoyl]-N'-{(2R)-[(formylhydroxyamino)methyl]-heptanoyl}-hydrazine $^1$H NMR (400 MHz, CD$_3$OD): δ 8.37–7.71 (m, 7H), 7.21 (s, 1H), 3.87 (m, 1H), 3.71–3.57 (m, 1H), 2.95 (m, 1H), 1.67 (m, 1H), 1.54 (m, 1H), 1.37 (m, 6H), 0.95 (t, J=6.7 Hz, 3H). MH+388.

Example 89

N-{[1-Methyl-5-oxo-2S-(pyridin-3-yl)-pyrrolidin-(3S)-yl]carbonyl}-N'-{(2R)-[(formylhydroxyamino)methyl]-heptanoyl}-hydrazine $^1$H NMR (400 MHz, CD$_3$OD): δ 8.57 (m, 1H), 7.90 (s, 1H), 7.84 (m, 1H), 7.55 (m, 1H), 3.79 (m, 1H), 3.53 (m, 1H), 3.08 (m, 1H), 2.92–2.69 (m, 3H), 2.68 (s, 3H), 1.62 (m, 1H), 1.47 (m, 1H), 1.35 (m, 6H), 0.93 (br s, 3H). MH+420.

Example 90

N-[(1,2-Dihydro-cinnolin-4-yl)carbonyl]-N'-{(2R)-[(formylhydroxyamino)methyl]-heptanoyl}-hydrazine $^1$H NMR (400 MHz, CD$_3$OD): δ 7.91 (s, 1H), 7.22 (m, 2H), 6.98 (m, 1H), 6.81 (d, J=7.8 Hz, 1H), 6.64 (m, 1H), 4.36 (br s, 1H), 3.79 (m, 1H), 3.53 (m, 1H), 2.87 (m, 1H), 1.63 (m, 1H), 1.48 (m, 1H), 1.34 (m, 6H), 0.92 (br s, 3H). MH+376.

Example 91

N-[4-(4-Acetylpiperazin-1-yl)phenoxyacetyl]-N'-{(2R)-[(formylhydroxyamino)methyl]-heptanoyl}-hydrazine $^1$H NMR (400 MHz, CD$_3$OD): δ 7.92 (s, 1H), 4.60 (br s, 2H), 3.90–3.50 (m, 6H), 3.07 (m, 4H), 3.04 (m, 1H), 2.16 (s, 3H), 1.62 (m, 1H), 1.51 (m, 1H), 1.35 (m, 6H), 0.93 (br s, 3H). MH+478.

Example 92

N-Phenylacetyl-N'-{(2R)-[(formylhydroxyamino)methyl]-heptanoyl}-hydrazine $^1$H NMR (400 MHz, CD$_3$OD): δ 8.30 (s, 1H), 7.90 (s, 1H), 7.32 (br s, 5H), 3.84–3.47 (m, 4H), 2.84 (m, 1H), 1.62 (m, 1H), 1.44 (m, 1H), 1.32 (m, 6H), 0.90 (br s, 3H). MH+336.

Example 93

N-{[1-Benzyl-5-oxo-pyrrolidin-(2S)-yl]-carbonyl}-N'-{(2R)-[(formylhydroxyamino)methyl]-heptanoyl}-hydrazine $^1$H NMR (400 MHz, CD$_3$OD): δ 9.20 (s, 1H), 7.63 (s, br s, 1H), 7.13 (m, 5H), 4.92 (m, 1H), 3.94–3.31 (m, 4H), 2.82 (m, 1H), 2.60–1.90 (m, 4H), 1.49 (m, 1H), 1.23 (m, 1H), 1.11 (m, 6H), 0.85 (t, J=6.7 Hz, 3H). MH+419.

Example 94

N-{[1-Benzyl-5-oxo-pyrrolidin-(2R)-yl]-carbonyl}-N'-{(2R)-[(formylhydroxyamino)methyl]-heptanoyl}-hydrazine $^1$H NMR (400 MHz, CD$_3$OD): δ 9.45 (br s, 1H), 7.82 (s, 1H), 7.30 (m, 5H), 5.06 (m, 1H), 4.10–3.50 (m, 4H), 2.95 (m, 1H), 2.85–2.10 (m, 4H), 1.67 (m, 1H), 1.41–1.26 (m, 7H), 0.87 (t, J=6.7 Hz, 3H). MH+419.

Example 95

N-[(5S)-Benzyl-3,6-dioxo-piperazin-(2S)-yl)acetyl]-N'-{(2R)-[(formylhydroxyamino)methyl]-heptanoyl}-hydrazine $^1$H NMR (400 MHz, CD$_3$OD): δ 7.90 (s, 1H), 7.38–7.23 (m, 5H), 4.34–4.21 (m, 2H), 3.82 (m, 1H), 3.49 (m, 1H), 3.31 (m, 1H), 3.06 (m, 1H), 2.85 (m, 1H), 1.57 (m, 1H), 1.46 (m, 1H), 1.34 (m, 6H), 0.92 (t, J=6.7 Hz, 3H). MH+462.

Example 96

N-[(Quinolin-4-yl)carbonyl]-N'-{(2R)-[(formylhydroxyamino)methyl]-heptanoyl}-hydrazine $^1$H NMR (400 MHz, CDCl$_3$): δ 9.11 (br s, 1H), 8.30–7.40 (m, 6H), 3.90 (m, 1H), 3.51 (m, 1H), 3.12 (m, 1H), 1.69 (m, 1H), 1.41 (m, 1H), 1.30 (m, 6H), 0.86 (t, J=6.7 Hz, 3H). MH+373.

Example 97

N-[(Quinolin-8-yl)carbonyl]-N'-{(2R)-[(formylhydroxyamino)methyl]-heptanoyl}-hydrazine $^1$H NMR (400 MHz, CD$_3$OD): δ 9.03 (m, 1H), 8.66 (t, J=6.3 Hz, 1H), 8.46 (m, 1H), 8.05 (d, J=8.1 Hz, 1H), 7.84 (s, 1H), 7.67 (m, 2H), 3.84–3.30 (m, 2H), 1.66 (m, 1H), 1.43–1.18 (m, 7H), 0.82 (t, J=6.7 Hz, 3H). MH+373.

Example 98

N-[(1,2,3,4-Tetrahydroquinolin-8-yl)carbonyl]-N'-{(2R)-[(formylhydroxyamino)methyl]-heptanoyl}-hydrazine $^1$H NMR (400 MHz, CD$_3$OD): δ 7.83 (s, 1H), 7.26 (d, J=8.0 Hz, 1H), 6.91 (m, 1H), 6.34 (m, 1H), 3.71 (m, 1H), 3.50 (m, 1H), 3.26 (t, J=5.6 Hz, 2H), 2.81 (m, 1H), 2.66 (t, J=6.2 Hz, 2H), 1.77 (m, 2H), 1.55 (m, 1H), 1.40 (m, 1H), 1.38 (m, 1H), 1.25 (m, 6H), 0.83 (t, J=6.7 Hz, 3H). MH+377.

Example 99

N-(N''-Acetyl-L-tyrosyl)-N'-{(2R)-[(formylhydroxyamino)methyl]-heptanoyl}-hydrazine $^1$H NMR (400 MHz, CD$_3$OD): δ 7.91 (s, 1H), 7.09 (d, J=8.4 Hz, 2H), 6.71 (d, J=8.4 Hz, 2H), 4.62 (m, 1H), 3.87

Example 100

N-[(1-Acetyl-1,2,3,4-tetrahydro-quinolin-6-yl)carbonyl]-N'-{(2R)-[(formylhydroxyamino)methyl]-heptanoyl}-hydrazine ¹H NMR (400 MHz, CD₃OD): δ 7.95 (s, 1H), 7.75 (m, 3H), 3.85 (m, 1H), 3.82 (t, J=6.4 Hz, 2H), 3.56 (m, 1H), 2.95 (m, 1H), 2.83 (t, J=6.5 Hz, 2H), 2.05 (s, 3H), 2.00 (m, 2H), 1.65 (m, 1H), 1.52 (m, 1H), 1.37 (m, 6H), 0.94 (t, J=6.7 Hz, 3H). MH+419.

Example 101

N-[(1H-Benzoimidazol-2-yl)carbonyl]-N'-{(2R)-[(formylhydroxyamino)methyl]-heptanoyl}-hydrazine ¹H NMR (400 MHz, CD₃OD): δ 7.95 (br s, 1H), 7.70 (br s, 2H), 7.32 (br s, 2H), 3.98–3.50 (m, 2H), 2.98 (m, 1H), 1.69 (m, 1H), 1.55 (m, 1H), 1.45 (m, 6H), 0.88 (t, J=6.7 Hz, 3H). MH+362.

Example 102

N-{[1-(2-Hydroxyacetyl)-1,2,3,4-tetrahydro-quinolin-6-yl]carbonyl}-N'-{(2R)-[(formylhydroxyamino)methyl]-heptanoyl}-hydrazine ¹H NMR (400 MHz, CD₃OD): δ 7.81 (s, 1H), 7.70–7.50 (m, 3H), 4.27 (s, 2H), 3.75 (m, 1H), 3.60 (m, 2H), 3.55 (m, 1H), 2.81 (m, 1H), 2.72 (m, 2H), 2.85 (m, 2H), 3.55 (m, 1H), 2.81 (m, 1H), 2.72 (m, 2H), 2.85 (m, 2H), 1.55 (m, 1H), 1.45 (m, 1H), 1.25 (m, 6H), 0.82 (t, J=6.7 Hz, 3H). MH+435.

Example 103

N-[(1H-Indol-5-yl)carbonyl]-N'-{(2R)-[(formylhydroxyamino)methyl]-heptanoyl}-hydrazine ¹H NMR (400 MHz, CD₃OD): δ 8.25 (br s, 1H), 7.95 (s, 1H), 7.68 (d, J=8.5 Hz, 1H), 7.46 (m, 1H), 7.35 (br s, 1H), 6.59 (br s, 1H), 3.95 (m, 1H), 3.59 (m, 1H), 2.96 (m, 1H), 1.66 (m, 1H), 1.54 (m, 1H), 1.36 (m, 6H), 0.95 (t, J=6.7 Hz, 3H). MH+361.

Example 104

N-{4-[Methyl-(4,6-dimethylpyrimidin-2-yl)-amino]benzoyl}-N'-{(2R)-[(formylhydroxyamino)methyl]-heptanoyl}-hydrazine)

¹H NMR (400 MHz, CD₃OD): δ 7.96 (s, 1H), 7.88 (m, 2H), 7.46 (m, 2H), 6.57 (s, 1H), 3.91 (m, 1H), 3.62 (m, 1H), 3.57 (s, 3H), 2.96 (m, 1H), 2.29 (s, 6H), 1.68 (m, 1H), 1.52 (m, 1H), 1.37 (m, 6H), 0.94 (t, J=6.7 Hz, 3H). MH+457.

Example 105

N-[(1-Benzo[1,3]dioxol-5-yl)carbonyl]-N'-{(2R)-[(formylhydroxyamino)methyl]-heptanoyl}-hydrazine ¹H NMR (400 MHz, CD₃OD): δ 7.94 (s, 1H), 7.49 (m, 1H), 7.36 (s, 1H), 6.92 (dd, J=8.2, 2.5 Hz, 1H), 6.06 (s, 2H), 3.92 (m, 1H), 3.58 (m, 1H), 2.93 (m, 1H), 1.63 (m, 1H), 1.49 (m, 1H), 1.38 (m, 6H), 0.94 (t, J=6.7 Hz, 3H). MH+366.

Example 106

N-{[4-(3,5-Dimethyl-pyrazol-1-yl)methyl]benzoyl}-N'-{(2R)-[(formylhydroxyamino)methyl]-heptanoyl}-hydrazine ¹H NMR (400 MHz, CD₃OD): δ 7.95 (s, 1H), 7.85 (d, J=8.2 Hz, 2H), 7.16 (d, J=8.2 Hz, 2H), 5.97 (s, 1H), 5.33 (s, 2H), 3.88 (m, 1H), 3.57 (m, 1H), 2.95 (m, 1H), 2.22 (s, 3H), 2.20 (s, 3H), 1.59 (m, 1H), 1.44 (m, 1H), 1.26 (m, 6H), 0.93 (t, J=6.7 Hz, 3H). MH+430.

Example 107

N-[4-(Morpholin-4-yl)-benzoyl]-N'-{(2R)-[(formylhydroxyamino)methyl]-heptanoyl}-hydrazine ¹H NMR (400 MHz, CD₃OD): δ 7.95 (s, 1H), 7.81 (d, J=6.6 Hz, 2H), 7.00 (d, J=6.6 Hz, 2H), 3.96 (m, 1H), 3.84 (m, 4H), 3.60 (m, 1H), 3.28 (m, 4H), 2.94 (m, 1H), 1.67 (m, 1H), 1.53 (m, 1H), 1.37 (m, 6H), 0.94 (t, J=6.7 Hz, 3H). MH+407.

Example 108

N-[4-Hydroxy-3-(morpholin-4-yl)methyl-benzoyl]-N'-{(2R)-[(formylhydroxyamino)methyl]-heptanoyl}-hydrazine ¹H NMR (400 MHz, CD₃OD): δ 7.95 (s, 1H), 7.85 (d, J=8.4 Hz, 2H), 6.85 (d, J=8.4 Hz, 2H), 3.85 (m, 2H), 3.80 (m, 1H), 3.74 (m, 4H), 3.55 (m, 1H), 2.93 (m, 1H), 2.68 (br s, 4H), 1.66 (m, 1H), 1.50 (m, 1H), 1.38 (m, 6H), 0.94 (t, J=6.7 Hz, 3H). MH+444.

Example 109

N-(3-Hydroxy-3-methyl-butanoyl)-N═-{(2R)-[(formylhydroxyamino)methyl]-heptanoyl}-hydrazine ¹H NMR (400 MHz, CD₃OD): δ 7.95 (s, 1H), 3.82 (m, 1H), 3.55 (m, 1H), 2.86 (m, 1H), 2.42 (d, J=5.7 Hz, 2H), 1.56 (m, 1H), 1.44 (m, 1H), 1.43–1.29 (m, 15H), 0.93 (t, J=6.7 Hz, 3H). MH+318.

Example 110

N-(4-Methylamino-benzoyl)-N'-{(2R)-[(formylhydroxyamino)methyl]-heptanoyl}-hydrazine ¹H NMR (400 MHz, CD₃OD): δ 7.95 (s, 1H), 7.73 (d, J=7.7 Hz, 2H), 6.60 (d, J=7.7 Hz, 2H), 3.96 (m, 1H), 3.58 (m, 1H), 2.93 (m, 1H), 2.83 (s, 3H), 1.52 (m, 1H), 1.38 (m, 1H), 1.26 (m, 6H), 0.94 (t, J=6.7 Hz, 3H). MH+351.

Example 111

N-[(1-Isopropyl-1H-benzotriazol-5-yl)carbonyl]-N'-{(2R)-[(formylhydroxyamino)methyl]-heptanoyl}-hydrazine ¹H NMR (400 MHz, CD₃OD): δ 8.75 (s, 1H), 8.09 (d, J=8.7 Hz, 1H), 7.96 (s, 1H), 7.93 (s, 1H), 5.26 (m, 1H), 3.86 (m, 1H), 3.65 (m, 1H), 2.96 (m, 1H), 1.75 (d, J=6.8 Hz, 6H), 1.70 (m, 1H), 1.56 (m, 1H), 1.28 (m, 6H), 0.95 (t, J=6.7 Hz, 3H). MH+405.

Example 112

N-[(1,2,3,4-Tetrahydro-isoquinolin-(3S)-yl)carbonyl]-N'-{(2R)-[(formylhydroxyamino)methyl]-heptanoyl}-hydrazine $^1$H NMR (400 MHz, CD$_3$OD): δ 7.90 (s, 1H), 7.20 (m, 4H), 4.30–3.40 (m, 5H), 3.10 (m, 1H), 2.90 (m, 1H), 2.72 (m, 1H), 1.65 (m, 1H), 1.50 (m, 1H), 1.36 (m, 6H), 0.94 (t, J=6.7 Hz, 3H). MH+377.

Example 113

N-[(5-Chloro-benzofuran-2-yl)carbonyl]-N'-{(2R)-[(formylhydroxyamino)methyl]-heptanoyl}-hydrazine $^1$H NMR (400 MHz, CD$_3$OD): δ 7.95 (s, 1H), 7.79 (s, 1H), 7.62 (d, J=8.8 Hz, 1H), 7.57 (d, J=5.1 Hz, 1H), 7.49 (d, J=8.8 Hz, 1H), 3.86 (m, 1H), 3.55 (m, 1H), 3.95 (m, 1H), 1.65 (m, 1H), 1.55 (m, 1H), 1.36 (m, 6H), 0.95 (t, J=6.8 Hz, 3H). MH+396.

Example 114

N-{[1-(Dimethylaminocarbonylmethyl)-3,4-dihydro-2H-quinolin-6-yl]carbonyl}-N'-{(2R)-[(formylhydroxyamino)methyl]-heptanoyl}-hydrazine $^1$H NMR (400 MHz, CD$_3$OD): δ 7.94 (br s, 1H), 7.55 (d, J=8.3 Hz, 1H), 7.51 (s, 1H), 6.38 (d, J=8.3 Hz, 1H), 4.28 (s, 2H), 3.95 (m, 1H), 3.63 (m, 1H), 3.41 (t, J=5.4 Hz, 2H), 3.13 (s, 3H), 2.98 (s, 3H), 2.97 (m, 1H), 2.83 (t, J=5.4 Hz, 2H), 1.99 (m, 4H), 1.65 (m, 1H), 1.50 (m, 1H), 1.36 (m, 6H), 0.94 (t, J=6.7 Hz, 3H). MH+462.

Example 115

N-[(2,2-Difluoro-benzo[1,3]dioxol-4-yl)carbonyl]-N'-{(2R)-[(formylhydroxyamino)methyl]-heptanoyl}-hydrazine $^1$H NMR (400 MHz, CD$_3$OD): δ 7.95 (s, 1H), 7.59 (m, 1H), 7.42 (m, 1H), 7.30 (m, 1H), 3.85 (m, 1H), 3.54 (m, 1H), 2.95 (m, 1H), 1.64 (m, 1H), 1.54 (m, 1H), 1.38 (m, 6H), 0.94 (t, J=6.7 Hz, 3H). MH+402.

Example 116

N-[(5-Amino-benzofuran-2-yl)carbonyl]-N'-{(2R)-[(formylhydroxyamino)methyl]-heptanoyl}-hydrazine $^1$H NMR (400 MHz, CD$_3$OD): δ 7.95 (s, 1H), 7.35 (m, 2H), 6.96 (m, 2H), 3.84 (m, 1H), 3.54 (m, 1H), 2.82 (m, 1H), 1.67 (m, 1H), 1.38 (m, 1H), 1.37 (m, 6H), 0.95 (t, J=6.7 Hz, 3H). MH+377.

Example 117

N-[(4-Oxo-1,2-dihydro-4H-pyrrolo[3,2,1-ij]quinolin-5-yl)carbonyl]-N'-{(2R)-[(formylhydroxyamino)methyl]-heptanoyl}-hydrazine $^1$H NMR (400 MHz, CD$_3$OD): δ 8.90 (br s, 1H), 7.95 (s, 1H), 7.66 (m, 1H), 7.58 (m, 1H), 7.34 (m, 1H), 4.52 (br s, 2H), 3.85 (m, 1H), 3.54 (m, 1H), 3.52 (m, 2H), 2.92 (m, 1H), 1.64 (m, 1H), 1.36–1.24 (m, &H), 0.94 (t, J=6.8 Hz, 3H). MH+415.

Example 118

N-[(7-Hydroxy-benzofuran-2-yl)carbonyl]-N'-{(2R)-[(formylhydroxyamino)methyl]-heptanoyl}-hydrazine $^1$H NMR (400 MHz, CD$_3$OD): δ 7.95 (s, 1H), 7.55 (m, 1H), 7.21–7.13 (m, 2H), 6.92 (m, 1H), 3.89 (m, 1H), 3.68 (m, 1H), 2.92 (m, 1H), 1.66 (m, 1H), 1.54 (m, 1H), 1.37 (m, 6H), 0.94 (t, J=6.8 Hz, 3H). MH+378.

Example 119

N-[(6-Methoxy-benzofuran-2-yl)acetyl]-N'-{(2R)-[(formylhydroxyamino)methyl]-heptanoyl}-hydrazine $^1$H NMR (400 MHz, CD$_3$OD): δ 7.91 (s, 1H), 7.63 (s, 1H), 7.53 (d, J=8.6 Hz, 1H), 7.05 (d, J=1.9 Hz, 1H), 6.88 (dt, J=8.6, 2.2 Hz, 1H), 3.84 (s, 3H), 3.76 (m, 1H), 3.64 (d, J=7.2 Hz, 2H), 3.53 (m, 1H), 2.86 (m, 1H), 1.65 (m, 1H), 1.48 (m, 1H), 1.26 (m, 1H), 0.92 (t, J=6.7 Hz, 3H). MH+406.

Example 120

N-[(5-Acetamidobenzofuran-2-yl)carbonyl]-N'-{(2R)-[(formylhydroxyamino)methyl]-heptanoyl}-hydrazine $^1$H NMR (400 MHz, CD$_3$OD): δ 8.36 (s, 1H), 8.04 (br s, 1H), 7.54 (m, 3H), 3.85 (m, 1H), 3.54 (m, 1H), 2.94 (m, 1H), 2.17 (s, 3H), 1.54 (m, 1H), 1.52 (m, 1H), 1.37 (m 6H), 0.95 (t, J=6.8 Hz, 3H). MH+419.

Example 121

N-[(2,3-Dihydro-benzo[1,4]dioxin-6-yl)carbonyl]-N'-{(2R)-[(formylhydroxyamino)methyl]-heptanoyl}-hydrazine $^1$H NMR (400 MHz, CD$_3$OD): δ 7.94 (s, 1H), 7.42 (m, 2H), 6.92 (m, 1H), 4.31 (m, 4H), 3.85 (m, 1H), 3.55 (m, 1H), 2.93 (m, 1H), 1.65 (m, 1H), 1.51 (m, 1H), 1.37 (m, 6H), 0.94 (t, J=6.7 Hz, 3H). MH+380.

Example 122

N-[(3-Amino-4,6-dimethyl-furo[2,3-b]pyridin-2-yl)carbonyl]-N'-{(2R)-[(formylhydroxyamino)methyl]-heptanoyl}-hydrazine $^1$H NMR (400 MHz, CD$_3$OD): δ 7.95 (s, 1H), 7.02 (s, 1H), 3.97 (m, 1H), 3.60 (m, 1H), 2.93 (m, 1H), 2.70 (s, 3H), 2.57 (s, 3H), 1.66 (m, 1H), 1.52 (m, 1H), 1.38 (m, 6H), 0.95 (t, J=6.7 Hz, 3H). MH+406.

Example 123

N-[(2-Methyl-5,6,7,8 tetrahydro-[1,6]naphthyridin-3-yl)carbonyl]-N'-{(2R)-[(formylhydroxyamino)methyl]-heptanoyl}-hydrazine $^1$H NMR (400 MHz, CD$_3$OD): δ 7.95 (s, 1H), 7.69 (br s, 1H), 3.71 (m, 1H), 3.45 (m, 1H), 3.05 (m, 2H), 2.90 (m, 2H), 2.68 (m, 2H), 2.50 (s, 3H), 1.65 (m, 1H), 1.48 (m, 1H), 1.36 (m, 6H), 0.95 (t, J=6.7 Hz, 3H). MH+392.

Example 124

N-[(6-Fluoro-4H-benzo[1,3]dioxin-8-yl)carbonyl]-N'-{(2R)-[(formylhydroxyamino)methyl]-heptanoyl}-hydrazine $^1$H NMR (400 MHz, CD$_3$OD): δ 7.95 (s, 1H), 7.55 (dd, J=9.2, 2.8 Hz, 1H), 7.07 (dd, J=7.8, 3.4 Hz, 1H), 5.40 (s, 2H), 4.97 (s, 2H), 3.86 (m, 1H), 3.65 (m, 1H), 2.95 (m, 1H), 1.67 (m, 1H), 1.51 (m, 1H), 1.26 (m, 6H), 0.94 (t, J=6.7 Hz, 3H). MH+398.

Example 125

N-[(7-Amino-1H-indol-2-yl)carbonyl]-N'-{(2R)-[(formylhydroxyamino)methyl]-heptanoyl}-hydrazine $^1$H NMR (400 MHz, CD$_3$OD): δ 7.96 (s, 1H), 7.12 (d, J=6.3 Hz, 1H), 7.03 (d, J=8.1 Hz, 1H), 6.89 (m, 1H), 6.60 (m, 1H), 3.90 (m, 1H), 3.55 (m, 1H), 2.95 (m, 1H), 1.67 (m, 1H), 1.51 (m, 1H), 1.26 (m, 6H), 0.94 (t, J=6.7 Hz, 3H). MH+376.

Example 126

N-[(1-Methyl-1,2,3,4-tetrahydro-quinolin-6-yl)carbonyl]-N'-{(2R)-[(formylhydroxyamino)methyl]-heptanoyl}-hydrazine $^1$H NMR (400 MHz, CD$_3$OD): δ 7.94 (s, 1H), 7.61 (d, J=8.7 Hz, 1H), 7.49 (s, 1H), 6.59 (d, J=8.7 Hz, 1H), 3.85 (m, 1H), 3.55 (m, 1H), 3.36 (m, 2H), 2.97 (s, 3H), 2.80 (t, J=6.3 Hz, 2H), 1.96 (m, 2H), 1.66 (m, 1H), 1.51 (m, 1H), 1.26 (m, 6H), 0.93 (t, J=6.7 Hz, 3H). MH+391.

Example 127

N'-[(6,7,9,10,12,13,15,16-Octahydro-5,8,11,14,17-pentaoxa-benzocyclopentadecen-2-yl)carbonyl]-N'-{(2R)-[(formylhydroxyamino)methyl]-heptanoyl}-hydrazine $^1$H NMR (400 MHz, CD$_3$OD): δ 7.95 (s, 1H), 7.50 (m, 1H), 7.49 (s, 1H), 7.01 (dd, J=8.4, 3.1 Hz, 1H), 4.18 (m, 4H), 3.89 (m, 4H), 3.86 (m, 1H), 3.73 (br s, 8H), 3.56 (m, 1H), 2.96 (m, 1H), 1.67 (m, 1H), 1.51 (m, 1H), 1.26 (m, 6H), 0.93 (t, J=6.7 Hz, 3H). MH+512.

Example 128

N-[(2-Benzo[1,3]dioxol-5-yl)acetyl]-N'-{(2R)-[(formylhydroxyamino)methyl]-heptanoyl}-hydrazine $^1$H NMR (400 MHz, CD$_3$OD): δ 7.95 (s, 1H), 6.85 (s, 1H), 6.77 (m, 2H), 5.93 (s, 2H), 3.84 (m, 1H), 3.56 (m, 1H), 3.49 (d, J=6.2 Hz, 2H), 2.86 (m, 1H), 1.60 (m, 1H), 1.48 (m, 1H), 1.34 (m, 6H), 0.92 (t, J=6.9 Hz, 3H). MH+380.

Example 129

N-Pentanoyl-N'-{2-[(formylhydroxyamino)methyl]-heptanoyl}-hydrazine $^1$H NMR (400 MHz, CDCl$_3$): δ 9.88 (m, 1H), 9.46 (s, 1H), 9.05 (d, J=3.5 Hz, 2H), 7.75 (s, 1H), 3.98–3.43 (m, 2H), 2.88 (m, 1H), 2.28 (m, 2H), 1.67 (m, 2H), 1.51–1.22 (m, 10H), 0.89 (m, 3H). MH+302.

Example 130

N-Benzoyl-N'-{2-[(formylhydroxyamino)methyl]-heptanoyl}-hydrazine $^1$H NMR (400 MHz, CDCl$_3$): δ 8.31 (s, 1H), 7.75 (m, 2H), 7.51–7.20 (m, 3H), 3.86–3.27 (m, 2H), 3.03 (s, 2H), 2.82–2.65 (m, 1H), 1.62 (m, 1H), 1.41–1.12 (m, 7H), 0.89 (m, 3H). MH+322.

Example 131

N-Trifluoroacetamido-N'-{2-[(formylhydroxyamino)methyl]-heptanoyl}-hydrazine $^1$H NMR (400 MHz, CDCl$_3$): δ 9.98 (s, 1H), 9.08 (s, 1H), 4.25–3.45 (m, 2H), 2.91 (m, 1H), 1.69 (m, 1H), 1.61–1.21 (m, 7H), 0.88 (m, 3H). MH+314.

Example 132

N-[(3-Hydroxy-naphthalen-2-yl)carbonyl]-N'-{2-[(formylhydroxyamino)methyl]-heptanoyl}-hydrazine $^1$H NMR (400 MHz, CDCl$_3$): δ 8.48 (s, 1H), 7.97 (s, 1H), 7.81 (m, 1H), 7.68 (m, 1H), 7.52 (m, 1H), 7.35–7.21 (m, 1H), 3.90–3.51 (m, 2H) 3.02 (m, 1H), 1.67 (m, 1H), 1.59–1.21 (m, 7H), 0.88 (m, 3H). MH+388.

Example 133

N-Phenylacetyl-N'-{2-[(formylhydroxyamino)methyl]-heptanoyl}-hydrazine $^1$H NMR (400 MHz, CDCl$_3$): δ 9.67 (s, 1H), 9.33 (s, 1H), 8.93 (s, 1H), 8.21 (s, 1H), 7.15 (m, 5H), 3.72–3.25 (m, 6H) 2.75–2.50 (m, 1H), 1.52 (m, 1H), 1.32–1.09 (m, 7H), 0.78 (m, 3H). MH+336.

Example 134

N-[(Furan-2-yl)carbonyl]-N'-{(2R)-[(formylhydroxyamino)methyl]-heptanoyl}-hydrazine $^1$H NMR (400 MHz, CDCl$_3$): δ 8.40 (s, 1H), 7.78 (s, 1H), 7.31 (s, 1H), 7.21–7.11 (m, 3H), 6.35 (m, 1H), 5.31 (s, 1H), 4.15–3.43 (m, 2H) 3.00–2.65 (m, 1H), 1.75 (m, 1H), 1.62–1.20 (m, 7H), 0.90 (m, 3H). MH+312.

Example 135

N-(4-Methoxybenzoyl)-N'-{(2R)-[(formylhydroxyamino)methyl]-heptanoyl}-hydrazine $^1$H NMR (400 MHz, CDCl$_3$): δ 7.75 (m, 1H), 6.89 (d, 1H), 6.72 (d, 1H), 4.05–3.40 (m, 5H) 3.00–2.58 (m, 1H), 1.82–1.11 (m, 8H), 0.88 (m, 3H). MH+352.

Example 136

N-[(1H-Indol-3-yl)acetyl]-N'-{(2R)-[(formylhydroxyamino)methyl]-heptanoyl}-hydrazine $^1$H NMR (400 MHz, CDCl$_3$): δ 8.28 (s, 1H), 7.48 (m, 1H), 7.36–6.94 (m, 4H), 3.89–3.19 (m, 4H) 2.71–2.42 (m, 1H), 2.02–1.04 (m, 8H), 0.76 (m, 3H). MH+375.

Example 137

N-(4-Dimethylaminobenzoyl)-N'-{(2R)-[(formylhydroxyamino)methyl]-heptanoyl}-hydrazine $^1$H NMR (400 MHz, CDCl$_3$): δ 8.40 (s, 1H), 7.71 (m, 2H), 6.61 (m, 2H), 4.05–3.38 (m, 2H) 3.02 (d, J=8 Hz, 6H), 2.93–2.55 (m, 1H), 1.68 (m, 1H), 1.52–1.21 (m, 7H), 0.89 (m, 3H). MH+365.

Example 138

N-(2-Hydroxybenzoyl)-N'-{(2R)-[(formylhydroxyamino)methyl]-heptanoyl}-hydrazine $^1$H NMR (400 MHz, CDCl$_3$): δ 8.37 (s, 1H), 7.82–7.57 (m, 2H), 7.41–6.81 (m, 2H), 6.65 (m, 1H), 3.95–3.35 (m, 2H) 3.00–2.57 (m, 1H), 1.75–1.05 (m, 8H), 0.89 (m, 3H). MH+338.

Example 139

N-[(Piperidin-4-yl)carbonyl]-N'-{(2R)-[(formylhydroxyamino)methyl]-heptanoyl}-hydrazine ¹H NMR (400 MHz, CDCl₃): δ 8.38 (s, 1H), 7.81 (s, 1H), 4.04–3.32 (m, 5H), 3.12–2.72 (m, 2H), 2.62–2.28 (m, 2H), 2.05–1.85 (m, 5H), 1.60 (m, 1H) 1.50–1.18 (m, 7H), 0.85 (m, 3H). MH+329.

Example 140

N-[(1,2,5,6-Tetrahydro-pyridin-3-yl)carbonyl]-N'-{(2R)-[(formylhydroxyamino)methyl]-heptanoyl}-hydrazine ¹H NMR (400 MHz, CDCl₃): δ 10.50 (s, 1H), 8.42 (s, 1H), 7.85 (m, 1H), 7.60–7.12 (m, 2H), 4.75 (m, 1H), 4.11 (m, 1H), 3.81–3.20 (m, 2H) 2.85–2.50 (m, 1H), 2.35–2.20 (m, 2H), 1.90 (m, 1H), 1.81–1.15 (m, 8H), 0.81 (m, 3H). MH+327.

Example 141

N-[(7-Methoxy-benzofuran-2-yl)carbonyl-N'-{(2R)-[(formylhydroxyamino)methyl]-heptanoyl}-hydrazine ¹H NMR (400 MHz, CD₃OD): δ 7.94 (s, 1H), 7.55 (m, 1H), 7.30 (m, 1H), 7.05 (m, 1H), 4.01 (s, 3H), 3.52–3.89 (m, 2H), 2.99 (M, 1H), 1.65 (m, 1H), 1.53 (m, 1H), 1.40 (m, 6H), 0.95 (m, 3H). MH+392.

Example 142

N-[(3-Chloro-4-methoxy-phenyl)acetyl]-N'-{(2R)-[(formylhydroxyamino)methyl]-heptanoyl}-hydrazine

MH+400.

Example 143

N-[(1H-Pyrrol-2-yl)carbonyl]-N'-{(2R)-[(formylhydroxyamino)methyl]-heptanoyl}-hydrazine

MH+311.

Example 144

N-[(Quinolin-7-yl)carbonyl]-N'-{(2R)-[(formylhydroxyamino)methyl]-heptanoyl}-hydrazine

MH+373.

Example 145

N-[(Pyridin-2-yl)carbonyl]-N'-{(2R)-[(formylhydroxyamino)methyl]-heptanoyl}-hydrazine

MH+323.

Example 146

N-(4-Chloro-3-methoxy-benzoyl)-N'-{(2R)-[(formylhydroxyamino)methyl]-heptanoyl}-hydrazine

MH+386.

Example 147

N-(3-Methoxybenzoyl)-N'-{(2R)-[(formylhydroxyamino)methyl]-heptanoyl}-hydrazine

MH+352.

Example 148

N-[(Quinolin-3-yl)carbonyl]-N'-{(2R)-[(formylhydroxyamino)methyl]-heptanoyl}-hydrazine

MH+373.

Example 149

N-[(5-Methyl-2-phenyl-oxazol-4-yl)carbonyl]-N'-{(2R)-[(formylhydroxyamino)methyl]-heptanoyl}-hydrazine

MH+403.

Example 150

N-[(Quinoxalin-2-yl)carbonyl]-N'-{(2R)-[(formylhydroxyamino)methyl]-heptanoyl}-hydrazine

MH+374.

Example 151

N-(Phenylacetyl)-N'-{2-[(formylhydroxyamino)methyl]-4-phenylbutanoyl}-hydrazine

MH+370.

Example 152

N-[(3-Methoxy-quinoxalin-2-yl)carbonyl]-N'-{(2R)-[(formylhydroxyamino)methyl]-heptanoyl}-hydrazine

MH+404.

Example 153

N-[(2,6-Dimethoxypyridin-3-yl)carbonyl]-N'-{(2R)-[(formylhydroxyamino)methyl]-heptanoyl}-hydrazine

MH+383.

Example 154

N-[(N''-Methylsulfonyl)-L-tyrosyl]-N'-{(2R)-[(formylhydroxyamino)methyl]-heptanoyl}-hydrazine

MH+459.

Example 155

N-{[5-Oxo-pyrrolidin-(2S)-yl]carbonyl)-N'-{(2R)-[(formylhydroxyamino)methyl]-heptanoyl}-hydrazine

MH+329.

Example 156

N-[4-(Pyrrol-1-yl)benzoyl]-N'-{(2R)-[(formylhydroxyamino)methyl]-heptanoyl}-hydrazine

MH+387.

Example 157

N-(4-Acetamidobenzoyl)-N'-{(2R)-
[(formylhydroxyamino)methyl]-heptanoyl}-
hydrazine

MH+379.

Example 158

N-[(3-Cyclopentyloxy-4-methoxy)benzoyl]-N'-{
(2R)-[(formylhydroxyamino)methyl]-heptanoyl}-
hydrazine

MH+436.

Example 159

N-(Phenylacetyl)-N'-{2-[(formylhydroxyamino)
methyl]-3-cyclopentyl-propanoyl}-hydrazine

MH+348.

Example 160

N-[(7-Methoxy-benzofuran-2-yl)carbonyl]-N'-{2-
[(formylhydroxyamino)methyl]-3-cyclopentyl-
propanoyl}-hydrazine

MH+404.

Example 161

N-[3-(Morpholin-4-yl)propanoyl]-N'-{(2R)-
[(formylhydroxyamino)methyl]-heptanoyl}-
hydrazine

MH+359.

Example 162

N-[(2,3-Dihydro-benzofuran-5-yl)carbonyl]-N'-{
(2R)-[(formylhydroxyamino)methyl]-heptanoyl}-
hydrazine

MH+364.

Example 163

N-[(4,6-Dimethoxy-pyrimidin-2-yl)benzoyl]-N'-{
(2R)-[(formylhydroxyamino)methyl]-heptanoyl}-
hydrazine

MH+460.

Example 164

N-[(2-Trifluoromethyl-5,6,7,8-tetrahydro-
naphthyridin-2-yl)carbonyl]-N'-{(2R)-
[(formylhydroxyamino)methyl]-heptanoyl}-
hydrazine

MH+446.

Example 165

N-[(9H-beta-Carbolin-3-yl)carbonyl]-N'-{(2R)-
[(formylhydroxyamino)methyl]-heptanoyl}-
hydrazine $^1$H NMR (400 MHz, CD$_3$OD): δ 8.20 (m, 1H), 8.59 (m, 1H), 8.05 (m, 1H), 7.80 (s, 1H), 7.46 (m, 2H), 7.16 (m, 1H), 7.75 (m, 1H), 3.43 (m, 1H), 2.89 (m, 1H), 1.56 (m, 1H), 1.43 (m, 1H), 1.30 (m, 6H), 0.83 (t, J=6.7 Hz, 3H). MH+412.

COMPOSITIONS ADMINISTRATION AND BIOLOGICAL ASSAYS

Compounds of Formula (1) and their pharmaceutically acceptable salts may be administered in a standard manner for antibiotics, for example orally, parenterally, sublingually, dermally, transdermally, rectally, via inhalation or via buccal administration.

Compositions of Formula (1) and their pharmaceutically acceptable salts which are active when given orally can be formulated as syrups, tablets, capsules, creams and lozenges. A syrup formulation will generally consist of a suspension or solution of the compound or salt in a liquid carrier for example, ethanol, peanut oil, olive oil, glycerine or water with a flavoring or coloring agent. Where the composition is in the form of a tablet, any pharmaceutical carrier routinely used for preparing solid formulations may be used. Examples of such carriers include magnesium stearate, terra alba, talc, gelatin, acacia, stearic acid, starch, lactose and sucrose. Where the composition is in the form of a capsule, any routine encapsulation is suitable, for example, using the aforementioned carriers in a hard gelatin capsule shell. Where the composition is in the form of a soft gelatin shell capsule, any pharmaceutical carrier routinely used for preparing dispersions or suspensions may be considered, for example, aqueous gums, celluloses, silicates or oils, and incorporated in a soft gelatin capsule shell.

Typical parenteral compositions consist of a solution or suspension of a compound or salt in a sterile aqueous or non-aqueous carrier optionally containing a parenterally acceptable oil, for example, polyethylene glycol, polyvinylpyrrolidone, lecithin, arachis oil or sesame oil.

Typical compositions for inhalation are in the form of a solution, suspension or emulsion that may be administered as a dry powder or in the form of an aerosol using a conventional propellant such as dichlorodifluoromethane or trichlorofluoromethane.

A typical suppository formulation comprises a compound of Formula (1) or a pharmaceutically acceptable salt thereof which is active when administered in this way, with a binding and/or lubricating agent, for example, polymeric glycols, gelatins, cocoa-butter or other low melting vegetable waxes or fats or their synthetic analogs.

Typical dermal and transdermal formulations comprise a conventional aqueous or non-aqueous vehicle, for example, a cream, ointment, lotion or paste or are in the form of a medicated plaster, patch or membrane.

Preferably the composition is in unit dosage form, for example a tablet, capsule or metered aerosol dose, so that the patient may administer a single dose.

Each dosage unit for oral administration contains suitably from 0.1 mg to 500 mg/Kg, and preferably from 1 mg to 100 mg/Kg, and each dosage unit for parenteral administration contains suitably from 0.1 mg to 100 mg/Kg, of a compound of Formula (1) or a pharmaceutically acceptable salt thereof calculated as the free acid. Each dosage unit for intranasal administration contains suitably 1–400 mg and preferably 10 to 200 mg per person. A topical formulation contains suitably 0.01 to 5.0% of a compound of Formula (1).

The daily dosage regimen for oral administration is suitably about 0.01 mg/Kg to 40 mg/Kg of a compound of Formula (1) or a pharmaceutically acceptable salt thereof calculated as the free acid. The daily dosage regimen for parenteral administration is suitably about 0.001 mg/Kg to 40 mg/Kg of a compound of Formula (1) or a pharmaceutically acceptable salt thereof calculated as the free acid. The daily dosage regimen for intranasal administration and oral inhalation is suitably about 10 to about 500 mg/person. The active ingredient may be administered from 1 to 6 times a day, sufficient to exhibit the desired activity.

No unacceptable toxicological effects are expected when compounds of the present invention are administered in accordance with the present invention.

The biological activity of the compounds of Formula (1) are demonstrated by the following test:

Biological Assay

*S. aureus* or *E. coli* PDF activity is measured at 25° C., using a continuous enzyme-linked assay developed by Lazennec & Meinnel ("Formate dehydrogenase-coupled spectrophotometric assay of peptide deformylase", Anal. Biochem. 1997, 244, pp. 180–182), with minor modifications. The reaction mixture is contained in 50 uL with 50 mM potassium phosphate buffer (pH 7.6), 15 mM NAD, 0.25 U formate dehydrogenase. The substrate peptide, f-Met-Ala-Ser, is included at the $K_M$ concentration. The reaction is triggered with the addition of 10 nM Def1 enzyme, and absorbance is monitored for 20 min at 340 nm.

Antimicrobial Activity Assay

Whole-cell antimicrobial activity was determined by broth microdilution using the National Committee for Clinical Laboratory Standards (NCCLS) recommended procedure, Document M7-A4, "Methods for Dilution Susceptibility Tests for Bacteria that Grow Aerobically" (incorporated by reference herein). The compound was tested in serial two-fold dilutions ranging from 0.06 to 64 mcg/ml. A panel of 12 strains were evaluated in the assay. This panel consisted of the following laboratory strains: *Staphylococcus aureus* Oxford, *Staphylococcus aureus* WCUH29, *Enterococcus faecalis* 1, *Enterococcus faecalis* 7, *Haemophilus influenzae* Q1, *Haemophilus influenzae* NEMC 1, *Moraxella catarrhalis* 1502, *Streptococcus pneumoniae* 1629, *Streptococcus pneumoniae* N1387, *Streptococcus pneumoniae* N1387, *E. coli* 7623 (AcrABEFD+) and *E. coli* 120 (AcrAB−). The minimum inhibitory concentration (MIC) was determined as the lowest concentration of compound that inhibited visible growth. A mirror reader was used to assist in determining the MIC endpoint.

What is claimed is:

1. A compound according to Formula (1):

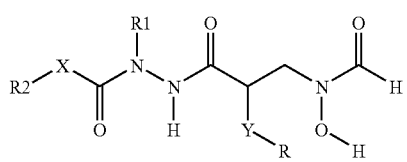

(1)

X = O, NR3 or a bond;
Y = O, CH2 or a bond wherein:

R represents:
$C_{2-6}$ alkyl (optionally substituted by alkoxy, halogen, or $C_{1-3}$ alkylsulfanyl), $C_{2-6}$ alkenyl (optionally substituted by alkoxy, halogen, or $C_{1-3}$ alkylsulfanyl), $C_{2-6}$ alkynyl (optionally substituted by alkoxy, halogen, or $C_{1-3}$ alkylsulfanyl), $(CH_2)_n$—$C_{3-6}$ carbocycle (optionally substituted by alkoxy, halogen, or $C_{1-3}$ alkylsulfanyl), $(CH_2)_n$—R4 {where R4 is phenyl, furan, benzofuran, thiophene, benzothiophene, tetrahydrofuran, tetrahydropyran, dioxane, 1,4-benzodioxane or benzo[1,3]dioxole; R4 is optionally substituted by one or more Cl, Br, I, $C_{1-3}$ alkyl (optionally substituted by one to three F) or $C_{1-2}$ alkoxy (optionally substituted by one to three F)};

R1 represents:
hydrogen, $C_{1-6}$ alkyl (optionally substituted by hydroxy, halogen, amino, guanidino, phenyl, pyridyl, pyrrolyl, indolyl, imidazolyl, furanyl, benzofuranyl, piperidinyl, morpholinyl, quinolinyl, piperazinyl or dimethylaminophenyl) or $(CH_2)_n$—$C_{3-7}$ carbocycle;

R2 represents:
hydrogen (provided that X is not O), $C_{1-3}$ substituted alkyl, $C_{2-3}$ substituted alkenyl, $C_{2-3}$ substituted alkynyl, $(CH_2)_n$—$C_{3-6}$ substituted carbocycle, aryl, heteroaryl, heterocyclic, carboxy (provided that X is not NR3 or O) or aminocarbonyl (provided that X is not NR3 or O);

R3 represents:
hydrogen, $C_{1-3}$ substituted alkyl, phenyl, or may be taken together with R2 and the nitrogen atom to which they are attached to form an optionally substituted heterocyclic ring which is optionally fused to an aryl, a heteroaryl, or a second heterocyclic ring;

X represents O, NR3 or a covalent bond;
Y represents O, $CH_2$ or a covalent bond;
n=0–2;
or a salt, solvate, or physiologically functional derivative thereof.

2. A compound as claimed in claim 1, with the following absolute configuration:

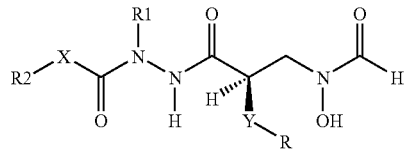

X = O, NR3 or a bond;
Y = O, CH2 or a bond or a salt, solvate or physiologically functional derivative thereof.

3. A compound as claimed in claim 2, wherein R1=H; or a salt, solvate or physiologically functional derivative thereof.

4. A compound as claimed in claim 1, wherein X=O; or a salt, solvate, or physiologically functional derivative thereof.

5. A compound according to claim 4 selected from the group consisting of:

N-Butyl-N-(t-butoxycarbonyl)-N'-{(2R)-[(formylhydroxyamino)methyl]-heptanoyl}-hydrazine;

N-Butyl-N-phenoxycarbonyl-N'-{(2R)-[(formylhydroxyamino)methyl]-heptanoyl}-hydrazine;

N-Isobutyl-N-(t-butoxycarbonyl)-N'-{(2R)-[(formylhydroxyamino)methyl]-heptanoyl}-hydrazine;

N-Isobutyl-N-phenoxycarbonyl-N'-{(2R)-[(formylhydroxyamino)methyl]-heptanoyl}-hydrazine;

N-Phenethyl-N-(t-butoxycarbonyl)-N'-{2-[(formylhydroxyamino)methyl]-heptanoyl}-hydrazine;

N-Cyclohexylmethyl-N-(t-butoxycarbonyl)-N'-{2-[(formylhydroxyamino)methyl]-heptanoyl}-hydrazine;

N-Benzyl-N-(t-butoxycarbonyl)-N'-{2-[(formylhydroxyamino)methyl]-heptanoyl}-hydrazine;

N-(3-pyridin-3-yl-propyl)-N-(t-butoxycarbonyl)-N'-{2-[(formylhydroxyamino)methyl]-heptanoyl}-hydrazine;
N-(2-Morpholin-4-yl-ethyl)-N-(t-butoxycarbonyl)-N'-{2-[(formylhydroxyamino)methyl]-heptanoyl}-hydrazine;
N-(4-Hydroxy-butyl)-N-(t-butoxycarbonyl)-N'-{2-[(formylhydroxyamino)methyl]-heptanoyl}-hydrazine;
N-(4-Amino-butyl)-N-(t-butoxycarbonyl)-N'-{2-[(formylhydroxyamino)methyl]-heptanoyl}-hydrazine;
N-(Tetrahydro-pyran-4-yl)-N-(t-butoxycarbonyl)-N'-{2-[(formylhydroxyamino)methyl]-heptanoyl}-hydrazine;
N-Methyl-N-(t-butoxycarbonyl)-N'-{2-[(formylhydroxyamino)methyl]-heptanoyl}-hydrazine;
N-(3-Aminopropyl)-N-(t-butoxycarbonyl)-N'-{2-[(formylhydroxyamino)methyl]-heptanoyl}-hydrazine;
N-(t-Butoxycarbonyl)-N'-{(2R)-[(formylhydroxyamino)methyl]-heptanoyl}-hydrazine;
N-(3-Hydroxypropyl)-N-(t-butoxycarbonyl)-N'-{2-[(formylhydroxyamino)methyl]-heptanoyl}-hydrazine;
N-Butyl-N-(t-butoxycarbonyl)-N'-{(2S)-[(formylhydroxyamino)methyl]-heptanoyl}-hydrazine;
N-Butyl-N-(phenoxycarbonyl)-N'-{(2S)-[(formylhydroxyamino)methyl]-heptanoyl}-hydrazine;
N-[2-(4-Dimethylaminophenyl)ethyl]-N-(t-butoxycarbonyl)-N'-{2-[(formylhydroxy amino)methyl]-heptanoyl}-hydrazine;
N-(t-Butoxycarbonyl)-N'-{2-[(formylhydroxyamino)methyl]-heptanoyl}-hydrazine;
N-Pentyl-N-(t-butoxycarbonyl)-N'-{2-[(formylhydroxyamino)methyl]-heptanoyl}-hydrazine;
N-[2-(1H-Indol-3-yl)-ethyl]-N-(t-butoxycarbonyl)-N'-{2-[(formylhydroxyamino)methyl]-heptanoyl}-hydrazine;
N-Isopentyl-N-(t-butoxycarbonyl)-N'-{2-[(formylhydroxyamino)methyl]-heptanoyl}-hydrazine;
N-Cyclohexyl-N-(t-butoxycarbonyl)-N'-{2-[(formylhydroxyamino)methyl]-heptanoyl}-hydrazine;
N-(1-Ethyl-propyl)-N-(t-butoxycarbonyl)-N'-{2-[(formylhydroxyamino)methyl]-heptanoyl}-hydrazine;
N-Isopropyl-N-(t-butoxycarbonyl)-N'-{2-[(formylhydroxyamino)methyl]-heptanoyl}-hydrazine;
N-Propyl-N-(t-butoxycarbonyl)-N'-{2-[(formylhydroxyamino)methyl]-heptanoyl}-hydrazine;
N-Ethyl-N-(t-butoxycarbonyl)-N'-{2-[(formylhydroxyamino)methyl]-heptanoyl}-hydrazine;
N-Methoxycarbonyl-N'-{2-[(formylhydroxyamino)methyl]-heptanoyl}-hydrazine;
N-{[1-(3,5-Dimethoxyphenyl)-1-methyl-ethoxy]carbonyl}-N'-{2-[(formylhydroxyamino)methyl]-heptanoyl}-hydrazine.

6. A compound as claimed in claim 1, wherein X=NR3; or a salt, solvate, or physiologically functional derivative thereof.

7. A compound according to claim 6 selected from the group consisting of:
N-Butyl-N-[(4-methylpiperazin-1-yl)carbonyl]-N'-{(2R)-[(formylhydroxyamino)methyl]-heptanoyl}-hydrazine;
N-Butyl-N-diphenylaminocarbonyl-N'-{(2R)-[(formylhydroxyamino)methyl]-heptanoyl}-hydrazine;
N-Butyl-N-(t-butylamino)carbonyl-N'-{2-[(formylhydroxyamino)methyl]-heptanoyl}-hydrazine;
N-Butyl-N-phenylaminocarbonyl-N'-{2-[(formylhydroxyamino)methyl]-heptanoyl}-hydrazine;
N-Butyl-N-[(3,5-dimethyl-4,5-dihydro-isoxazol-4-yl)aminocarbonyl]-N'-{2-[(formylhydroxyamino)methyl]-heptanoyl}-hydrazine;
N-Butyl-N-[(1-morpholin-4-yl)carbonyl]-N'-{2-[(formylhydroxyamino)methyl]-heptanoyl}-hydrazine;
N-Phenylaminocarbonyl-N'-{2-[(formylhydroxyamino)methyl]-4-phenyl-butanoyl}-hydrazine;
N-Phenylaminocarbonyl-N'-{2-[(formylhydroxyamino)methyl]-hexanoyl}-hydrazine;
N-Phenylaminocarbonyl-N'-{2-[(formylhydroxyamino)methyl]-3-phenyl-propanoyl}-hydrazine;
N-Phenylaminocarbonyl-N'-{2-[(formylhydroxyamino)methyl]-3-(3,4-dichlorophenyl)-propanoyl}-hydrazine;
N-Phenylaminocarbonyl-N'-{2-[(formylhydroxyamino)methyl]-heptanoyl}-hydrazine;
N-(3,4-Dichlorophenylaminocarbonyl)-N'-{2-[(formylhydroxy amino)methyl]-heptanoyl}-hydrazine;
N-Phenylaminocarbonyl-N'-{(2R)-[(formylhydroxyamino)methyl]-heptanoyl}-hydrazine;
N-(3,4-Dichlorophenylaminocarbonyl)-N'-{(2R)-[(formylhydroxyamino)methyl]-heptanoyl}-hydrazine;
N-[(1-Morpholin-4-yl)carbonyl]-N'-{(2R)-[(formylhydroxyamino)methyl]-heptanoyl}-hydrazine;
N-[(2-Methoxyphenyl)aminocarbonyl]-N'-{(2R)-[(formylhydroxyamino)methyl]-heptanoyl}-hydrazine;
N-[(2,4-Dichlorophenyl)aminocarbonyl]-N'-{(2R)-[(formylhydroxyamino)methyl]-heptanoyl}-hydrazine;
N-[(2,6-Dichlorophenyl)aminocarbonyl]-N'-{(2R)-[(formylhydroxyamino)methyl]-heptanoyl}-hydrazine;
N-[(4-Methyl-piperazin-1-yl)carbonyl]-N'-{(2R)-[(formylhydroxyamino)methyl]-heptanoyl}-hydrazine;
N-[(4-Chloro-3-trifluoromethylphenyl)aminocarbonyl]-N'-{(2R)-[(formylhydroxyamino)methyl]-heptanoyl}-hydrazine;
N-[(Methyl-phenyl-amino)carbonyl]-N'-{(2R)-[(formylhydroxyamino)methyl]-heptanoyl}-hydrazine.

8. A compound as claimed in claim 1, wherein X is a covalent bond; or a salt, solvate, or physiologically functional derivative thereof.

9. A compound according to claim 8 selected from the group consisting of:
N-[(Phenylaminocarbonyl)-carbonyl]-N'-{(2R)-[(formylhydroxyamino)methyl]-heptanoyl}-hydrazine;
N-Butyl-N-{[1-(t-butoxycarbonyl)-piperidin-4-yl]carbonyl}-N'-{2-[(formylhydroxyamino)methyl]-heptanoyl}-hydrazine;
N-Butyl-N-{[(1-t-butoxycarbonyl)-pyrrolidin-(2S)-yl]carbonyl}-N'-{2-[(formylhydroxyamino)methyl]-heptanoyl}-hydrazine;
N-Butyl-N-{[(1-t-butylaminocarbonyl)piperidin-4-yl]carbonyl}]-N'-{2-[(formylhydroxyamino)methyl]-heptanoyl}-hydrazine;
N-Butyl-N-{[(1-t-butylcarbonyl)piperidin-4-yl]carbonyl}]-N'-{2-[(formylhydroxyamino)methyl]-heptanoyl}-hydrazine;
N-Butyl-N-[(1,2,3,4-tetrahydro-quinoxalin-2-yl)carbonyl]-N'-{2-[(formylhydroxyamino)methyl]-heptanoyl}-hydrazine;
N-(p-Methoxyphenylacetyl)-N'-{(2R)-[(formylhydroxyamino)methyl]-heptanoyl}-hydrazine;
N-Phenoxyacetyl-N'-{(2R)-[(formylhydroxyamino)methyl]-heptanoyl}-hydrazine;
N-[(p-Methoxy-phenoxy)acetyl]-N'-{(2R)-[(formylhydroxyamino)methyl]-heptanoyl}-hydrazine;
N-(2,6-Dichlorophenyl-acetyl)-N'-{(2R)-[(formylhydroxyamino)methyl]-heptanoyl}-hydrazine;

N-(3,4-Dichlorophenylacetyl)-N'-{(2R)-[(formylhydroxyamino)methyl]-heptanoyl}-hydrazine;
N-(Ethoxycarbonyl)carbonyl)-N'-{(2R)-[(formylhydroxyamino)methyl]-heptanoyl}-hydrazine;
N-(2,4-Dichlorophenylacetyl)-N'-{(2R)-[(formylhydroxyamino)methyl]-heptanoyl}-hydrazine;
N-[(Benzofuran-2-yl)carbonyl]-N'-{(2R)-[(formylhydroxyamino)methyl]-heptanoyl}-hydrazine;
N-(2,3-Dichlorophenoxyacetyl)-N'-{(2R)-[(formylhydroxyamino)methyl]-heptanoyl}-hydrazine;
N-(3,4-Dimethoxyphenylacetyl)-N'-{(2R)-[(formylhydroxyamino)methyl]-heptanoyl}-hydrazine;
N-[(1H-Indol-2-yl)carbonyl]-N'-{(2R)-[(formylhydroxyamino)methyl]-heptanoyl}-hydrazine;
N-[(2-Methyl-pyridin-3-yl)carbonyl]-N'-{(2R)-[(formylhydroxyamino)methyl]-heptanoyl}-hydrazine;
N-[(5-Methoxy-benzofuran-2-yl)carbonyl]-N'-{(2R)-[(formylhydroxyamino)methyl]-heptanoyl}-hydrazine;
N-[(2,3-Dihydro-benzo[1,4]dioxin-(2S)-yl)carbonyl]-N'-{(2R)-[(formylhydroxyamino)methyl]-heptanoyl}-hydrazine;
N-[(Quinolin-2-yl)carbonyl]-N'-{(2R)-[(formylhydroxyamino)methyl]-heptanoyl}-hydrazine;
N-[(1,2,3,4-Tetrahydro-quinolin-6-yl)carbonyl]-N'-{(2R)-[(formylhydroxyamino)methyl]-heptanoyl}-hydrazine;
N-[(Tetrahydro-furan-(2S)-yl)carbonyl]-N'-{(2R)-[(formylhydroxyamino)methyl]-heptanoyl}-hydrazine;
N-[(Tetrahydro-furan-(2R)-yl)carbonyl]-N'-{(2R)-[(formylhydroxyamino)methyl]-heptanoyl}-hydrazine;
N-[(3-Methyl-benzofuran-2-yl)carbonyl]-N'-{(2R)-[(formylhydroxyamino)methyl]-heptanoyl}-hydrazine;
N-[(Pyridin-2-yl)acetyl]-N'-{(2R)-[(formylhydroxyamino)methyl]-heptanoyl}-hydrazine;
N-{3-[3-(4-Methoxybenzyl)-1H-benzoimidazol-2-yl]-propanoyl}-N'-{(2R)-[(formylhydroxyamino)methyl]-heptanoyl}-hydrazine;
N-[(Pyrimidin-2-yl)carbonyl]-N'-{(2R)-[(formylhydroxyamino)methyl]-heptanoyl}-hydrazine;
N-[(2-Methyl-5,6,7,8-tetrahydro-[1,8]naphthyridin-3-yl)carbonyl]-N'-{(2R)-[(formylhydroxyamino)methyl]-heptanoyl}-hydrazine;
N-[(Isoquinolin-3-yl)carbonyl]-N'-{(2R)-[(formylhydroxyamino)methyl]-heptanoyl}-hydrazine;
N-[(5,6,7,8-Tetrahydro-[1,8]naphthyridin-2-yl)carbonyl]-N'-{(2R)-[(formylhydroxyamino)methyl]-heptanoyl}-hydrazine;
N-(Phenylacetyl)-N'-{2-[(formylhydroxyamino)methyl]-heptanoyl}-hydrazine;
N-[(3,4-Dihydro-2H-benzo[b][1,4]dioxepin-7-yl)carbonyl]-N'-{(2R)-[(formylhydroxyamino)methyl]-heptanoyl}-hydrazine;
N-[(1-Methyl-2,5-dioxo-imidazolidin-4-yl)acetyl]-N'-{(2R)-[(formylhydroxyamino)methyl]-heptanoyl}-hydrazine;
N-(Phenylacetyl)-N'-{2-[(formylhydroxyamino)methyl]-3-phenyl-propanoyl}-hydrazine;
N-(Phenylacetyl)-N'-{2-[(formylhydroxyamino)methyl]-3-(3,4-dichloro)phenyl-propanoyl}-hydrazine;
N-[(4-Imidazol-1-yl)benzoyl]-N'-{(2R)-[(formylhydroxyamino)methyl]-heptanoyl}-hydrazine;
N-{[1-Methyl-5-oxo-2-S-(pyridin-3-yl)-pyrrolidin-(3S)-yl]carbonyl}-N'-{(2R)-[(formylhydroxyamino)methyl]-heptanoyl}-hydrazine;
N-[(1,2-Dihydro-cinnolin-4-yl)carbonyl]-N'-{(2R)-[(formylhydroxyamino)methyl]-heptanoyl}-hydrazine;
N-[4-(4-Acetylpiperazin-1-yl)phenoxyacetyl]-N'-{(2R)-[(formylhydroxyamino)methyl]-heptanoyl}-hydrazine;
N-Phenylacetyl-N'-{(2R)-[(formylhydroxyamino)methyl]-heptanoyl}-hydrazine;
N-{[1-Benzyl-5-oxo-pyrrolidin-(2S)-yl]-carbonyl}-N'-{(2R)-[(formylhydroxyamino)methyl]-heptanoyl}-hydrazine;
N-{[1-Benzyl-5-oxo-pyrrolidin-(2R)-yl]-carbonyl}-N'-{(2R)-[(formylhydroxyamino)methyl]-heptanoyl}-hydrazine;
N-[(5S)-Benzyl-3,6-dioxo-piperazin-(2S)-yl)acetyl]-N'-{(2R)-[(formylhydroxyamino)methyl]-heptanoyl}-hydrazine;
N-[(Quinolin-4-yl)carbonyl]-N'-{(2R)-[(formylhydroxyamino)methyl]-heptanoyl}-hydrazine;
N-[(Quinolin-8-yl)carbonyl]-N'-{(2R)-[(formylhydroxyamino)methyl]-heptanoyl}-hydrazine;
N-[(1,2,3,4-Tetrahydroquinolin-8-yl)carbonyl]-N'-{(2R)-[(formylhydroxyamino)methyl]-heptanoyl}-hydrazine;
N-(N"-Acetyl-L-tyrosyl)-N'-{(2R)-[(formylhydroxyamino)methyl]-heptanoyl}-hydrazine;
N-[(1-Acetyl-1,2,3,4-tetrahydro-quinolin-6-yl)carbonyl]-N'-{(2R)-[(formylhydroxyamino)methyl]-heptanoyl}-hydrazine;
N-[(1H-Benzoimidazol-2-yl)carbonyl]-N'-{(2R)-[(formylhydroxyamino)methyl]-heptanoyl}-hydrazine;
N-([1-(2-Hydroxyacetyl)-1,2,3,4-tetrahydro-quinolin-6-yl]carbonyl}-N'-{(2R)-[(formylhydroxyamino)methyl]-heptanoyl}-hydrazine;
N-[(1H-Indol-5-yl)carbonyl]-N'-{(2R)-[(formylhydroxyamino)methyl]-heptanoyl}-hydrazine;
N-{4-[Methyl-(4,6-dimethylpyrimidin-2-yl)-amino]benzoyl}-N'-{(2R)-[(formylhydroxyamino)methyl]-heptanoyl}-hydrazine);
N-[(1-Benzo[1,3]dioxol-5-yl)carbonyl]-N'-{(2R)-[(formylhydroxyamino)methyl]-heptanoyl}-hydrazine;
N-{[4-(3,5-Dimethyl-pyrazol-1-yl)methyl]benzoyl}-N'-{(2R)-[(formylhydroxyamino)methyl]-heptanoyl}-hydrazine;
N-[4-(Morpholin-4-yl)-benzoyl]-N'-{(2R)-[(formylhydroxyamino)methyl]-heptanoyl}-hydrazine;
N-[4-Hydroxy-3-(morpholin-4-yl)methyl-benzoyl]-N'-{(2R)-[(formylhydroxyamino)methyl]-heptanoyl}-hydrazine;
N-(3-Hydroxy-3-methyl-butanoyl)-N'-{(2R)-[(formylhydroxyamino)methyl]-heptanoyl}-hydrazine;
N-(4-Methylamino-benzoyl)-N'-{(2R)-[(formylhydroxyamino)methyl]-heptanoyl}-hydrazine;
N-[(1-Isopropyl-1H-benzotriazol-5-yl)carbonyl]-N'-{(2R)-[(formylhydroxyamino)methyl]-heptanoyl}-hydrazine;
N-[(1,2,3,4-Tetrahydro-isoquinolin-(3S)-yl)carbonyl]-N'-{(2R)-[(formylhydroxyamino)methyl]-heptanoyl}-hydrazine;
N-[(5-Chloro-benzofuran-2-yl)carbonyl]-N'-{(2R)-[(formylhydroxyamino)methyl]-heptanoyl}-hydrazine;
N-{[1-(Dimethylaminocarbonylmethyl)-3,4-dihydro-2H-quinolin-6-yl]carbonyl}-N'-{(2R)-[(formylhydroxyamino)methyl]-heptanoyl}-hydrazine;
N-[(2,2-Difluoro-benzo[1,3]dioxol-4-yl)carbonyl]-N'-{(2R)-[(formylhydroxyamino)methyl]-heptanoyl}-hydrazine;

N-[(5-Amino-benzofuran-2-yl)carbonyl]-N'-{(2R)-[(formylhydroxyamino)methyl]-heptanoyl}-hydrazine;

N-[(4-Oxo-1,2-dihydro-4H-pyrrolo[3,2,1-ij]quinolin-5-yl)carbonyl]-N'-{(2R)-[(formylhydroxyamino)methyl]-heptanoyl}-hydrazine;

N-[(7-Hydroxy-benzofuran-2-yl)carbonyl]-N'-{(2R)-[(formylhydroxyamino)methyl]-heptanoyl}-hydrazine;

N-[(6-Methoxy-benzofuran-2-yl)acetyl]-N'-{(2R)-[(formylhydroxyamino)methyl]-heptanoyl}-hydrazine;

N-[(5-Acetamidobenzofuran-2-yl)carbonyl]-N'-{(2R)-[(formylhydroxyamino)methyl]-heptanoyl}-hydrazine;

N-[(2,3-Dihydro-benzo[1,4]dioxin-6-yl)carbonyl]-N'-{(2R)-[(formylhydroxyamino)methyl]-heptanoyl}-hydrazine;

N-[(3-Amino-4,6-dimethyl-furo[2,3-b]pyridin-2-yl)carbonyl]-N'-{(2R)-[(formylhydroxyamino)methyl]-heptanoyl}-hydrazine;

N-[(2-Methyl-5,6,7,8-tetrahydro-[1,6]naphthyridin-3-yl)carbonyl]-N'-{(2R)-[(formylhydroxyamino)methyl]-heptanoyl}-hydrazine;

N-[(6-Fluoro-4H-benzo[1,3]dioxin-8-yl)carbonyl]-N'-{(2R)-[(formylhydroxyamino)methyl]-heptanoyl}-hydrazine;

N-[(7-Amino-1H-indol-2-yl)carbonyl)]N'-{(2R)-[(formylhydroxyamino)methyl]-heptanoyl}-hydrazine;

N-[(1-Methyl-1,2,3,4-tetrahydro-quinolin-6-yl)carbonyl]-N'-{(2R)-[(formylhydroxyamino)methyl]-heptanoyl}-hydrazine;

N'-[(6,7,9,10,12,13,15,16-Octahydro-5,8,11,14,17-pentaoxa-benzocyclopentadecen-2-yl)carbonyl]-N'-{(2R)-[(formylhydroxyamino)methyl]-heptanoyl}-hydrazine;

N-[(2-Benzo[1,3]dioxol-5-yl)acetyl]-N'-{(2R)-[(formylhydroxyamino)methyl]-heptanoyl}-hydrazine;

N-Pentanoyl-N'-{2-[(formylhydroxyamino)methyl]-heptanoyl}-hydrazine;

N-Benzoyl-N'-{2-[(formylhydroxyamino)methyl]-heptanoyl}-hydrazine;

N-Trifluoroacetamido-N'-{2-[(formylhydroxyamino)methyl]-heptanoyl}-hydrazine;

N-[(3-Hydroxy-naphthalen-2-yl)carbonyl]-N'-{2-[(formylhydroxyamino)methyl]-heptanoyl}-hydrazine;

N-Phenylacetyl-N'-{2-[(formylhydroxyamino)methyl]-heptanoyl}-hydrazine;

N-[(Furan-2-yl)carbonyl]-N'-{(2R)-[(formylhydroxyamino)methyl]-heptanoyl}-hydrazine;

N-(4-Methoxybenzoyl)-N'-{(2R)-[(formylhydroxyamino)methyl]-heptanoyl}-hydrazine;

N-[(1H-Indol-3-yl)acetyl]-N'-{(2R)-[(formylhydroxyamino)methyl]-heptanoyl}-hydrazine;

N-(4-Dimethylaminobenzoyl)-N'-{(2R)-[(formylhydroxyamino)methyl]-heptanoyl}-hydrazine;

N-(2-Hydroxybenzoyl)-N'-{(2R)-[(formylhydroxyamino)methyl]-heptanoyl}-hydrazine;

N-[(Piperidin-4-yl)carbonyl]-N'-{(2R)-[(formylhydroxyamino)methyl]-heptanoyl}-hydrazine;

N-[(1,2,5,6-Tetrahydro-pyridin-3-yl)carbonyl]-N'-{(2R)-[(formylhydroxyamino)methyl]-heptanoyl}-hydrazine;

N-[(7-Methoxy-benzofuran-2-yl)carbonyl-N'-{(2R)-[(formylhydroxyamino)methyl]-heptanoyl}-hydrazine;

N-[(3-Chloro-4-methoxy-phenyl)acetyl]-N'-{(2R)-[(formylhydroxyamino)methyl]-heptanoyl}-hydrazine;

N-[(1H-Pyrrol-2-yl)carbonyl]-N'-{(2R)-[(formylhydroxyamino)methyl]-heptanoyl}-hydrazine;

N-[(Quinolin-7-yl)carbonyl]-N'-{(2R)-[(formylhydroxyamino)methyl]-heptanoyl}-hydrazine;

N-[(Pyridin-2-yl)carbonyl]-N'-{(2R)-[(formylhydroxyamino)methyl]-heptanoyl}-hydrazine;

N-(4-Chloro-3-methoxy-benzoyl)-N'-{(2R)-[(formylhydroxyamino)methyl]-heptanoyl}-hydrazine;

N-(3-Methoxybenzoyl)-N'-{(2R)-[(formylhydroxyamino)methyl]-heptanoyl}-hydrazine;

N-[(Quinolin-3-yl)carbonyl]-N'-{(2R)-[(formylhydroxyamino)methyl]-heptanoyl}-hydrazine;

N-[(5-Methyl-2-phenyl-oxazol4-yl)carbonyl]-N'-{(2R)-[(formylhydroxyamino)methyl]-heptanoyl}-hydrazine;

N-[(Quinoxalin-2-yl)carbonyl]-N'-{(2R)-[(formylhydroxyamino)methyl]-heptanoyl}-hydrazine;

N-(Phenylacetyl)-N'-{2-[(formylhydroxyamino)methyl]-4-phenylbutanoyl}-hydrazine;

N-[(3-Methoxy-quinoxalin-2-yl)carbonyl]-N'-{(2R)-[(formylhydroxyamino)methyl]-heptanoyl}-hydrazine;

N-[(2,6-Dimethoxypyridin-3-yl)carbonyl]-N'-{(2R)-[(formylhydroxyamino)methyl]-heptanoyl}-hydrazine;

N-[(N"-Methylsulfonyl)-L-tyrosyl]-N'-{(2R)-[(formylhydroxyamino)methyl]-heptanoyl}-hydrazine;

N-{[5-Oxo-pyrrolidin-(2S)-yl]carbonyl}-N'-{(2R)-[(formylhydroxyamino)methyl]-heptanoyl}-hydrazine;

N-[(4-(Pyrrol-1-yl)benzoyl]-N'-{(2R)-[(formylhydroxyamino)methyl]-heptanoyl}-hydrazine;

N-(4-Acetamidobenzoyl)-N'-{(2R)-[(formylhydroxyamino)methyl]-heptanoyl}-hydrazine;

N-[(3-Cyclopentyloxy-4-methoxy)benzoyl]-N'-{(2R)-[(formylhydroxyamino)methyl]-heptanoyl}-hydrazine;

N-(Phenylacetyl)-N'-{2-[(formylhydroxyamino)methyl]-3-cyclopentyl-propanoyl}-hydrazine;

N-[(7-Methoxy-benzofuran-2-yl)carbonyl]-N'-{2-[(formylhydroxyamino)methyl]-3-cyclopentyl-propanoyl}-hydrazine;

N-[3-(Morpholin-4-yl)propanoyl]-N'-{(2R)-[(formylhydroxyamino)methyl]-heptanoyl}-hydrazine;

N-[(2,3-Dihydro-benzofuran-5-yl)carbonyl]-N'-{(2R)-[(formylhydroxyamino)methyl]-heptanoyl}-hydrazine;

N-[(4,6-Dimethoxy-pyrimidin-2-yl)benzoyl]-N'-{(2R)-[(formylhydroxyamino)methyl]-heptanoyl}-hydrazine;

N-[(2-Trifluoromethyl-5,6,7,8-tetrahydro-naphthyridin-2-yl)carbonyl]-N'-{(2R)-[(formylhydroxyamino)methyl]-heptanoyl}-hydrazine;

N-[(9H-beta-Carbolin-3-yl)carbonyl]-N'-{(2R)-[(formylhydroxyamino)methyl]-heptanoyl}-hydrazine.

10. A method of treating a bacterial infection by administering to a subject in need of treatment a compound according to claim 1.

* * * * *